United States Patent
Naka et al.

(10) Patent No.: US 10,174,111 B2
(45) Date of Patent: Jan. 8, 2019

(54) THERAPEUTIC DRUG FOR MALIGNANT TUMORS

(71) Applicant: National University Corporation Kochi University, Kochi-shi, Kochi (JP)

(72) Inventors: Tetsuji Naka, Osaka (JP); Satoshi Serada, Osaka (JP); Minoru Fujimoto, Osaka (JP); Masayoshi Toyoura, Kyoto (JP); Yuji Shoya, Kyoto (JP)

(73) Assignee: National University Corporation Kochi University, Kochi (JP)

( * ) Notice: Subject to any disclaimer, the term of this patent is extended or adjusted under 35 U.S.C. 154(b) by 0 days.

(21) Appl. No.: 15/108,242

(22) PCT Filed: Dec. 25, 2014

(86) PCT No.: PCT/JP2014/006456
§ 371 (c)(1),
(2) Date: Jun. 24, 2016

(87) PCT Pub. No.: WO2015/098113
PCT Pub. Date: Jul. 2, 2015

(65) Prior Publication Data
US 2017/0051056 A1 Feb. 23, 2017

(30) Foreign Application Priority Data
Dec. 27, 2013 (JP) ................. 2013-272084

(51) Int. Cl.
C07K 16/28 (2006.01)
A61K 31/713 (2006.01)
G01N 33/574 (2006.01)
C12N 15/113 (2010.01)
C07K 16/30 (2006.01)
G01N 33/92 (2006.01)
A61K 39/00 (2006.01)

(52) U.S. Cl.
CPC ............ *C07K 16/28* (2013.01); *A61K 31/713* (2013.01); *C07K 16/303* (2013.01); *C07K 16/3023* (2013.01); *C07K 16/3046* (2013.01); *C07K 16/3069* (2013.01); *C12N 15/1138* (2013.01); *G01N 33/57449* (2013.01); *G01N 33/57492* (2013.01); *G01N 33/92* (2013.01); *A61K 2039/505* (2013.01); *C07K 2317/33* (2013.01); *C07K 2317/34* (2013.01); *C07K 2317/565* (2013.01); *C07K 2317/622* (2013.01); *C07K 2317/92* (2013.01); *C12N 2310/14* (2013.01); *G01N 2333/705* (2013.01)

(58) Field of Classification Search
CPC .................. C07K 16/28; C07K 2317/565
USPC .................................................... 424/133.1
See application file for complete search history.

(56) References Cited

U.S. PATENT DOCUMENTS 7,919,091 B2   4/2011   Bihain et al.

FOREIGN PATENT DOCUMENTS

| WO | 00/78962 A1 | 12/2000 |
| WO | 2012/140627 A1 | 10/2012 |
| WO | 2013/190555 A1 | 12/2013 |

OTHER PUBLICATIONS

Mesli et al. (Eur. J. Biochem. 271, 3103-3114 (2004)).*
Papatheodorou et al. (Infection and Immunity 80 (4): 1418-1423 (Apr. 2012)).*
Hiramatsu et al., "Abstract 4382: Anti-human LSR monoclonal antibody inhibits tumor growth of ovarian cancer directly," *Proceedings of the AACR 106th Annual Meeting* 75(15):4382, 2015, 4 pages.
Leth-Larsen et al., "Functional Heterogeneity within the CD44 High Human Breast Cancer Stem Cell-Like Compartment Reveals a Gene Signature Predictive of Distant Metastasis," *Molecular Medicine* 18(7):1109-1121, 2012.
"Lipolysis Stimulated Lipoprotein Receptor Antibody," URL:https://www.novusbio.com/products/lipolysis-stimuated-lipoprotein-receptor-antibody_h00051599-b01p, download date Aug. 15, 2017, 3 pages.
Garcia et al., "Prognostic Value of LISCH7 mRNA in Plasma and Tumor of Colon Cancer Patients," *Clin Cancer Res* 13(21):6351-6358, 2007.
Herbsleb et al., "Increased cell motility and invasion upon knockdown of lipolysis stimulated lipoprotein receptor (LSR) in SW780 bladder cancer cells," *BMC Medical Genomics*, 2008, 17 pages.
Narvekar et al., "Liver-Specific Loss of Lipolysis-Stimulated Lipoprotein Receptor Triggers Systemic Hyperlipidemia in Mice," *Diabetes* 58:1040-1049, 2009.

* cited by examiner

*Primary Examiner* — Lynn A Bristol
(74) *Attorney, Agent, or Firm* — Seed IP Law Group LLP

(57) ABSTRACT

According to the present disclosure there are provided compositions and methods for treating malignant tumors, including an anti-LSR (lipolysis stimulated lipoprotein receptor) antibody that comprises the presently disclosed antibody heavy and light chain complementarity determining region (CDR) sequences, or an antigen-binding fragment thereof, or a functional equivalent thereof. Further provided for treating an LSR-positive malignancy is an LSR antagonist or an LSR inhibitor such as a nucleic acid. Therapeutic administration of the anti-LSR antibody to a subject having an LSR-positive malignant tumor is also described.

2 Claims, 55 Drawing Sheets
Specification includes a Sequence Listing.

Fig. 9

- SEQ ID No: 1
AVTLDESGGGLQTPGGALSLVCKASGFTFRDYQMNWVRQAPGKGLEWVAGINGBSSWTDY
GAAVKGRATISRDNGQSTVRLQLNNLRAEDTATYYCARGSSHDAWGHGTEVYVSTGGGSG
GGGSGGGGSDVALTQPASVSANPGETYKITCSGGSYYGSYYGWYQQKSPGSAPVTMIYN
NNRPSNIPSRFSGSLSGSTNTLTITGVQADDEAVYYCGSIDSNAGVPGAGTTLTV

- SEQ ID No: 2
AVTLDESGGGLQTPGGALSLVCKASGFTFRDYQMNWVRQAPGKGLEWVAGINGRSTWTDY
GAAVKGRATISRDNGQSTVRLQLNNLRAEDTATYFCARGSSHDAWGHGTEVYVSTGGGSG
GGGSGCGGSDVALTQPASVSANPGFTVKITCSGGSSYYGTYYFYOWYQQKAPGSAPVTLIY
DNTNRPSNIPSRFSGSTSGSTSTLTITGVQVDDEAVYFCGSHDSSYSGBFGAGTTLTV

- SEQ ID No: 3
AVTLDESGGGLQTPGGGBGSLVCRGGQSTVRLQLNNLRAEDTGTYYCARGSMDGWGHGTEVYVSTGKGRGSG
GSAVQGRATISRDNGQSTVRLQLNNLRAEDTGTTYCARGSMDGWGHGTEVYVSTGKGGRSG
GGSGCGGSDVALTQPSSVSANPGETVSSYVYYSWFQQKSSGSSAPVTVYFW
NDKRPSNIPSRFSGSLSGSTNTLTITGPRAHDEAVYCGAYEDSSAGFGAGTTLTV

- SEQ ID No: 4
AVTLHESGGGLQMHGGALSLAVCRASGHDFS5YEMQWRQAPGKGLEWVAGSGAGSGTRYG
SAVQKGRATSRIDNGQSTVRLQLNSLRAEDTGHYFCARSSSNIDAWGHSTEVYVSTGKGRSGH
GRSGGGSDVALTQPASVSAAHLGGTVKITCSGHGHYAESYYYYSWYYQQKSPGSTPVTVFYWV
DKRPSNIPSRENGGRLSGSTNTLTITGVQYREDEAVFCGSYEDSRSAGFGAGTTLTV

- SEQ ID No: 5
AVTLDESGGGLQTPGGALSLVCKLASGFTDESSYEMQWVRQAPGRGLEWVTCIRSGSGSSTRYG
SAVQKGRATISRDNGQSTVRLQLNMLRAEDTGTTYCARGSTRAWGHGTEVYVSTGGGGSGG
GGSGCGGSDVALTQPASVSANPGETVKITCSGGSSYAGSYYGYGRYQQKSPGSAPVTVFYN
DQRPSDIFSRFKFGSTSGSTATLTITGVQVEDEAVYICGTVEDSKGVEGAGTTLTV

- SEQ ID No: 6
AVTLDESGGGLQTPGGALSLVCEASGDPSSHEMQWVBQASPGKGLEWVAGISGAGSSTRYG
SAVQGRATISRENGQSTVRLQLNLKAEDTGTTYCARGSLBAWGHGTEVYVSTGKGGRSGG
GSSGCGGSDVALTQPASVSAKSGSTATLTITGVQAEDEAVYFCGSYDSSAGLFGAGTTLTV
NQRPSDIFSGSKSGSTATLTITGVQAEDEAVYFCGSYDSSAGLFGAGTTLTV

Fig. 15 Immunohistochemical staining for LSRs (Ovarian Cancer)

Examination of antitumor effect of anti-LSR antibody on ovarian clear cell adenocarcinoma (RMG-I xenograft model)

Fig.32

Greater omentum metastasis

Lymph node metastasis

X 100

X 400

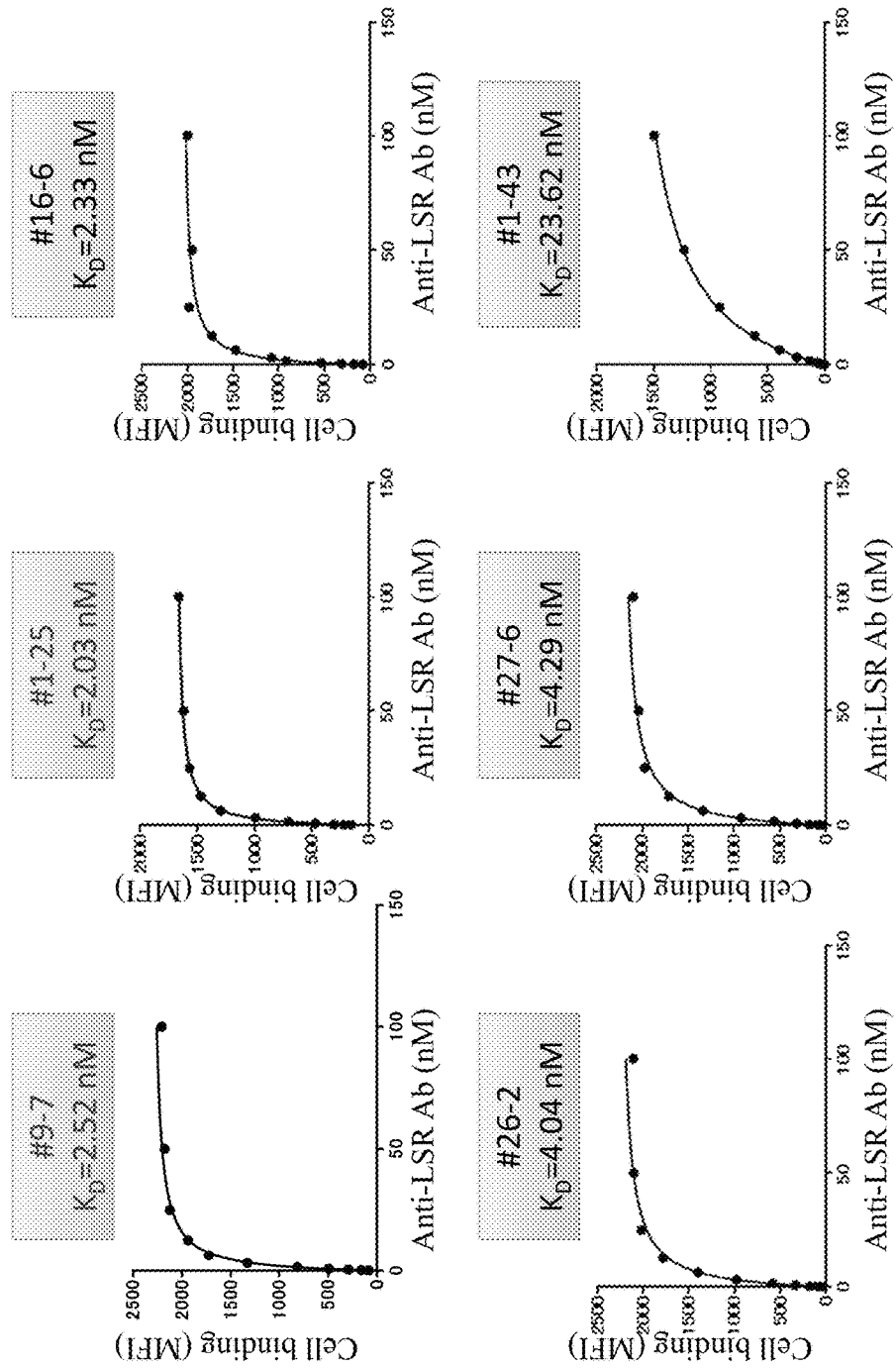

Fig.39

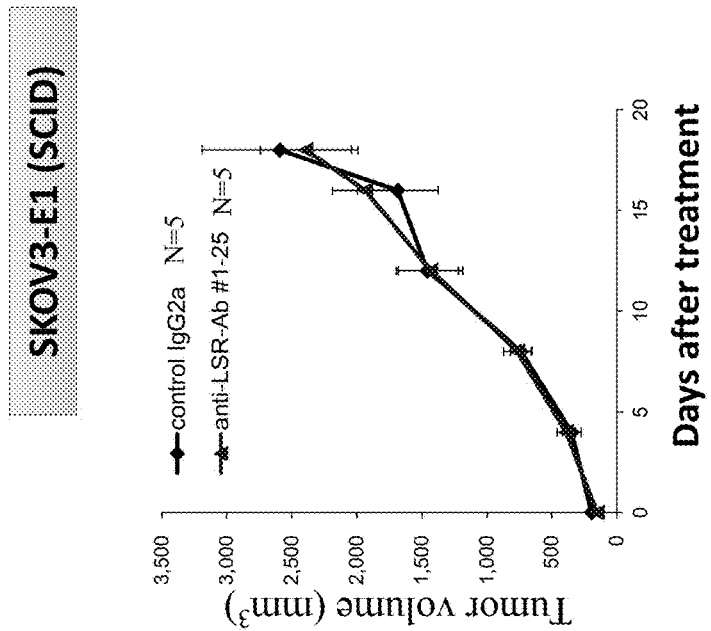
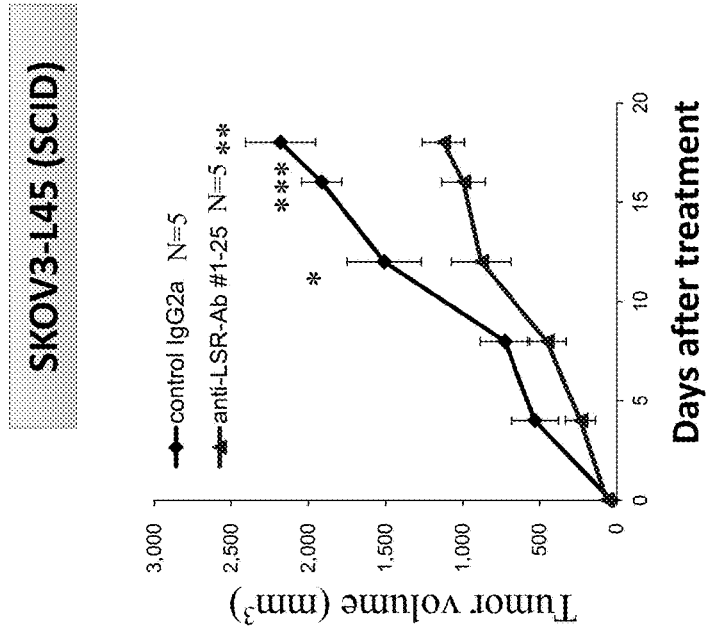
Fig.47

Fig.52

- To C57BL/6J(8w), 1mg/body of
  ① Mouse IgG2a (Sigma M7769)
  ② Anti-LSR antibody #1-25
  was intraperitoneally administered, and the following items were assessed on Day7

|   | cont IgG | LSR |
|---|---|---|
| ♂ | 4 | 3 |
| ♀ | 3 | 4 |

○ Extracted organs:
Brain, heart, kidney, liver, lung and spleen

○ Blood collection item:
WBC, RBC, Hb, Plt
T-Bil, ALT, ALP, Amy, BUN, Cr, Ca, P, TP,
Alb, Na, K, Glob, Glu Automated blood cell counter : VetScan HMII
Veterinary biochemical blood analyzer :
VetScan VS2

Fig.53

| | Control IgG (n=3) | Anti-LSR Ab (n=3) | normal | p value |
|---|---|---|---|---|
| WBC(10⁹/l) | 2.60 (1.32-3.27) | 2.07 (1.36-2.69) | 2.3±1.16 | 0.512 |
| Ly(%) | 91.8 (91.1-92.8) | 91.8 (81.1-97.0) | 87.5±3.35 | 0.064 |
| Mo(%) | 2.2 (1.9-2.6) | 2.4 (1.6-3.5) | 2.6±1.19 | 0.749 |
| Gr(%) | 6.0 (5.3-6.8) | 5.8 (1.1-15.4) | 9.2±2.68 | 0.105 |
| RBC(10¹²/l) | 9.21 (8.66-9.56) | 9.58 (8.49-10.48) | 9.86±0.327 | 0.897 |
| Hb | 14.6 (12.5-15.0) | 14.8 (12.5-16.3) | 15.0±0.48 | 0.734 |
| Hct | 44.74 (42.60-46.80) | 45.54 (40.51-49.00) | 44.1±1.58 | 0.889 |
| Plt(10⁹/l) | 487 (475-511) | 433 (253-544) | 1158±104 | 0.893 |

Student's t-test

Fig.54

| | Control IgG (n=3) | Anti-LSR Ab (n=4) | normal | p value |
|---|---|---|---|---|
| WBC(10⁹/l) | 2.61 (1.73-3.16) | 2.44 (1.80-3.31) | 1.5±0.7 | 0.763 |
| Ly(%) | 92.8 (91.8-94.5) | 84.7 (81.1-89.0) | 86.4±3.44 | 0.019 |
| Mo(%) | 3.3 (2.0-4.4) | 2.9 (2.0-4.0) | 2.5±0.79 | 0.668 |
| Gr(%) | 4.0 (3.6-4.7) | 12.4 (8.7-16.2) | 11.1±4.49 | 0.016 |
| RBC(10¹²/l) | 9.53 (9.37-9.62) | 10.02 (9.64-10.48) | 9.53±0.24 | 0.093 |
| Hb | 15.1 (15.0-15.1) | 15.7 (15.1-16.3) | 14.8±0.5 | 0.131 |
| Hct | 45.58 (44.50-46.24) | 47.24 (45.78-49.00) | 42.7±1.24 | 0.137 |
| Plt(10⁹/l) | 375 (247-482) | 280 (204-337) | 942±85.9 | 0.226 |

Student's t-test

Fig.55

| | Control IgG (n=3) | Anti-LSR Ab (n=3) | p value |
|---|---|---|---|
| Alb (g/dl) | 3.4 (3.0-4.1) | 3.7 (3.7-3.8) | 0.427 |
| ALP (U/l) | 149 (142-155) | 139 (126-151) | 0.303 |
| ALT (U/l) | 29 (26-33) | 26 (21-30) | 0.427 |
| Amy (U/l) | 995 (879-1098) | 961 (915-1041) | 0.675 |
| T-Bil (mg/dl) | 0.3 (0.3-0.4) | 0.4 (0.3-0.4) | 0.519 |
| BUN (mg/dl) | 20 (19-22) | 22 (19-26) | 0.435 |
| Ca (mg/dl) | 10.4 (9.8-11.4) | 10.2 (9.7-10.7) | 0.744 |
| P (mg/dl) | 9.2 (8-11.1) | 10.3 (8.7-11.7) | 0.447 |
| Cr (mg/dl) | (<0.2-0.8) | (<0.2-0.4) | |
| Glu (mg/dl) | 197 (190-207) | 232 (187-306) | 0.401 |
| Na (mmol/l) | 158 (153-169) | 146 (144-148) | 0.081 |
| K (mmol/l) | 5.5 (5.2-6.0) | 5.3 (5.1-6.8) | 0.627 |
| TP (g/dl) | 5.4 (5.0-6.1) | 5.3 (5.2-5.4) | 0.717 |
| Glob (g/dl) | 2.0 (1.9-2.0) | 1.5 (1.5-1.6) | 0.001 |

Fig.56

| | Control IgG (n=3) | Anti LSR Ab (n=4) | p value |
|---|---|---|---|
| Alb (g/dl) | 4.0 (3.8-4.2) | 4.0 (3.9-4.1) | 0.832 |
| ALP (U/l) | 168 (158-178) | 152 (137-172) | 0.197 |
| ALT (U/l) | 23 (15-28) | 18 (14-22) | 0.243 |
| Amy (U/l) | 922 (865-1000) | 834 (654-1012) | 0.391 |
| T-Bil (mg/dl) | 0.3 (0.3-0.4) | 0.4 (0.3-0.4) | 0.721 |
| BUN (mg/dl) | 21 (18-25) | 15 (12-16) | 0.023 |
| Ca (mg/dl) | 9.6 (9.2-9.9) | 9.5 (9.3-9.7) | 0.562 |
| P (mg/dl) | 9.3 (8.7-10.1) | 9.5 (9.1-10.2) | 0.635 |
| Cr (mg/dl) | (<0.2-0.3) | (<0.2) | |
| Glu (mg/dl) | 158 (142-172) | 187 (155-222) | 0.175 |
| Na (mmol/l) | 150 (149-151) | 144 (141-146) | 0.007 |
| K (mmol/l) | 5.0 (4.5-5.6) | 5.4 (4.6-6.5) | 0.491 |
| TP (g/dl) | 5.4 (5.2-5.5) | 5.2 (5.1-5.3) | 0.117 |
| Glob (g/dl) | 1.4 (1.4-1.5) | 1.3 (1.1-1.3) | 0.038 |

THERAPEUTIC DRUG FOR MALIGNANT TUMORS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690188_402USPC_SEQUENCE_LISTING.txt. The text file is 32.9 KB, was created on Mar. 7, 2018, and is being submitted electronically via EFS-Web.

TECHNICAL FIELD

The present invention relates to a therapeutic drug, diagnostic drug or the like for malignant tumor.

BACKGROUND ART

LSR (lipolysis stimulated lipoprotein receptor) is known as a molecule associated with metabolism of low-density lipoprotein (LDL). Several LSR related research results have been reported. For example, Non Patent Literature 1 describes that LSR expression is reduced in a liver of obese and type 2 diabetes mouse models. Further, Non Patent Literature 2 describes that LSRs are expressed in bladder cancer. Non Patent Literature 3 describes that LSRs are expressed in colon cancer cells. Non Patent Literature 4 describes that LSRs are expressed in breast cancer cells. Patent Literature 1 describes that LSRs are expressed in ovarian cancer cells or the like.

CITATION LIST

Patent Literature

[PTL 1] WO 2012/140627

Non Patent Literature

[NPL 1] "Liver-specific loss of lipolysis-stimulated lipoprotein receptor triggers systemic hyperlipidemia in mice." Narvekar et al., Diabetes. 2009 May; 58(5): 1040-9
[NPL 2] "Increased cell motility and invasion upon knockdown of lipolysis stimulated lipoprotein receptor (LSR) in SW780 bladder cancer cells." Herbsleb et al., BMC Med Genomics. 2008 Jul. 22; 1:31.
[NPL 3] "Prognostic value of LISCH7 mRNA in plasma and tumor of colon cancer patients." Garcia et al., Clin Cancer Res. 2007 Nov. 1; 13(21): 6351-8.
[NPL 4] "Functional heterogeneity within the CD44 high human breast cancer cell-like stem compartment reveals a gene signature predictive of distant metastasis." Leth-Larsen et al., Mol Med. 2012 Sep. 25; 18: 1109-21.

SUMMARY OF INVENTION

Solution to Problem

The disease mechanism of malignant tumor is complex, with many parts unclear. Thus, many medical needs remain unfulfilled in the field. The inventors have discovered that growth of malignant tumor cells is suppressed when the malignant tumor cells are contacted with an anti-LSR antibody as a number of researches are conducted on malignant tumor. Furthermore, when an LSR siRNA was transfected into malignant tumor cells, growth of malignant tumor cells was also suppressed in this case. In addition, when an anti-LSR antibody was actually administered to a malignant tumor model mouse, a notable decrease in tumor volume was observed. In view of the above, it was elucidated that an LSR suppressant such as an anti-LSR antibody is effective in treating malignant tumor. In this regard, the present invention provides a novel therapeutic agent for malignant tumor targeting LSRs and the like.

Further, the inventors elucidated, as described in the Examples disclosed below, the presence of many LSR negative patients while there are LSR positive patients among malignant tumor patients. In view of the above, it was elucidated that diagnosis of the presence or absence of LSR positive state in a malignant tumor patient prior to therapy is importantin the treatment of malignant tumor targeting LSRs.

The Examples of the above-described Patent Literature 1 suggest that an LSR mRNA was detected in a few types of cancer. The claims have an actual recitation of an anti-LSR antibody inducing apoptosis of cancer cells. However, Patent Literature 1 does not have any pharmacological data from an actual successful cancer therapy. In addition, Patent Literature 1 does not describe that the presence or absence of an LSR positive condition in a malignant tumor patient is diagnosed prior to therapy. For this reason, an anti-LSR antibody could not be considered effective for treating malignant tumor only from the results of Patent Literature 1.

In one aspect, the present invention provides a therapeutic or prophylactic drug for malignant tumor, comprising a suppressant of an LSR (lipolysis stimulated lipoprotein receptor).

In one embodiment, the suppressantin the present invention can comprise an anti-LSR (lipolysis stimulated lipoprotein receptor) antibody, an antigen binding fragment or a functional equivalent thereof, or a nucleic acid.

In another embodiment, the suppressantin the present invention can comprise an anti-LSR (lipolysis stimulated lipoprotein receptor) antibody or an antigen binding fragment or a functional equivalent thereof.

Instill another embodiment, the suppressantin the present invention can be an RNAi molecule directed to an LSR or a polynucleotide encoding the RNAi molecule.

In still another embodiment, the malignant tumor in the present invention can be LSR positive malignant tumor.

In still another embodiment, the present invention can be for administration to a patient determined to have an episode of LSR positive malignant tumor.

In still another embodiment, the present invention can be for administration to a patient among malignant tumor patients whose malignant tumor has been determined to be LSR positive malignant tumor.

In still another embodiment, the anti-LSR antibody in the present invention can be an anti-LSR antibody that specifically binds to an epitope of an LSR. More specifically, the antibody may have positions 116-134 and/or 216-230 of SEQ ID NO: 7 as the epitope.

In still another embodiment, the anti-LSR antibody in the present invention can be an antibody having an ability to inhibit exacerbation due to a VLDL.

In still another embodiment, the anti-LSR antibody in the present invention may be one or more antibodies selected from the group consisting of: (a) an antibody with heavy chain CDRs 1, 2, and 3 and light chain CDRs 1, 2, and 3 comprising amino acid sequences set forth in positions 31-35, 50-66, 99-104, 153-165, 182-188 and 221-230 of SEQ ID NO: 1, respectively; (b) an antibody with heavy chain CDRs 1, 2, and 3 and light chain CDRs 1, 2, and 3 comprising amino acid sequences set forth in positions 31-35, 50-66, 99-103, 152-165, 182-188 and 221-230 of SEQ ID NO: 2, respectively; (c) an antibody with heavy chain CDRs 1, 2, and 3 and light chain CDRs 1, 2, and 3 comprising amino acid sequences set forth in positions 31-35, 50-66, 99-104, 153-165, 182-188 and 221-229 of SEQ ID NO: 3, respectively; (d) an antibody with heavy chain CDRs 1, 2, and 3 and light chain CDRs 1, 2, and 3 comprising amino acid sequences set forth in positions 31-35, 50-66, 99-104, 153-165, 182-188 and 221-229 of SEQ ID NO: 4, respectively; (e) an antibody with heavy chain CDRs 1, 2, and 3 and light chain CDRs 1, 2, and 3 comprising amino acid sequences set forth in positions 31-35, 50-66, 99-104, 153-165, 182-188 and 221-229 of SEQ ID NO: 5, respectively; and (f) an antibody with heavy chain CDRs 1, 2, and 3 and light chain CDRs 1, 2, and 3 comprising amino acid sequences set forth in positions 31-35, 50-66, 99-104, 153-165, 182-188 and 221-229 of SEQ ID NO: 6, respectively, or a mutant of the antibody, which is free of a mutation in the CDRs but comprises one or several substitutions, additions, or deletions in a framework of the antibody in the mutant.

In still another embodiment, the anti-LSR antibody in the present invention can be a monoclonal antibody.

In still another embodiment, an antibody class of the anti-LSR antibody in the present invention may be IgG.

In still another embodiment, the anti-LSR antibody in the present invention may be an antigen binding fragment.

In another aspect, the present invention provides an agent for suppressing cell division of a malignant tumor cell, comprising an anti-LSR antibody.

In another aspect, the present invention provides a companion diagnostic drug for malignant tumor therapy targeting an LSR, comprising an LSR detection agent.

In one embodiment, the LSR detection agent in the present invention can comprise an anti-LSR antibody. In another aspect, the present invention provides a companion diagnostic method for malignant tumor therapy targeting an LSR, comprising inspecting whether a malignant tumor sample of a malignant tumor patient is LSR positive. In another aspect, the present invention provides an antibody or antibodies selected from the group consisting of: (a) an antibody with heavy chain CDRs 1, 2, and 3 and light chain CDRs 1, 2, and 3 comprising amino acid sequences set forth in positions 31-35, 50-66, 99-104, 153-165, 182-188 and 221-230 of SEQ ID NO: 1, respectively; (b) an antibody with heavy chain CDRs 1, 2, and 3 and light chain CDRs 1, 2, and 3 comprising amino acid sequences set forth in positions 31-35, 50-66, 99-103, 152-165, 182-188 and 221-230 of SEQ ID NO: 2, respectively; (c) an antibody with heavy chain CDRs 1, 2, and 3 and light chain CDRs 1, 2, and 3 comprising amino acid sequences set forth in positions 31-35, 50-66, 99-104, 153-165, 182-188 and 221-229 of SEQ ID NO: 3, respectively; (d) an antibody with heavy chain CDRs 1, 2, and 3 and light chain CDRs 1, 2, and 3 comprising amino acid sequences set forth in positions 31-35, 50-66, 99-104, 153-165, 182-188 and 221-229 of SEQ ID NO: 4, respectively; (e) an antibody with heavy chain CDRs 1, 2, and 3 and light chain CDRs 1, 2, and 3 comprising amino acid sequences set forth in positions 31-35, 50-66, 99-104, 153-165, 182-188 and 221-229 of SEQ ID NO: 5, respectively; and (f) an antibody with heavy chain CDRs 1, 2, and 3 and light chain CDRs 1, 2, and 3 comprising amino acid sequences set forth in positions 31-35, 50-66, 99-104, 153-165, 182-188 and 221-229 of SEQ ID NO: 6, respectively, or a mutant of the antibody, which is free of a mutation in the CDRs but comprises one or several substitutions, additions, or deletions in a framework of the antibody in the mutant. These antibodies may be an antibody selected from a monoclonal antibody, polyclonal antibody, chimeric antibody, humanized antibody, human antibody, multifunctional antibody, bispecific or oligospecific antibody, single chain antibody, scFV, diabody, sc (Fv)$_2$ (single chain (Fv)$_2$), and scFv-Fc.

In another aspect, the present invention provides a composition for preventing or treating malignant tumor, comprising an LSR binding agent. In one embodiment, the malignant tumor in the present invention can be LSR positive malignant tumor.

In another embodiment, the present invention can further comprise a cell-killing agent.

In another embodiment, the LSR binding agent in the present invention may be an antibody, a fragment or a functional equivalent thereof, or a nucleic acid. In a specific embodiment, the LSR binding agent in the present invention may be an antibody or a fragment or a functional equivalent thereof, further bound to a cell killing agent. In a specific embodiment, the malignant tumor in the present invention may comprise ovarian cancer. The ovarian cancer in the present invention may be recurrent ovarian cancer. Alternatively, the malignant tumor may be metastasized ovarian cancer. The malignant tumor can comprise ovarian cancer, pancreatic cancer, lung cancer, gastric cancer, or colon cancer. Alternatively, the malignant tumor may be early-stage ovarian cancer. In another embodiment, ovarian cancer can be ovarian serous adenocarcinoma or ovarian clear cell adenocarcinoma. In a specific embodiment, the LSR binding agent in the present invention may be characterized by having an antibody or a fragment or a functional equivalent thereof, the antibody being one or more antibodies selected from the group consisting of: (a) an antibody with heavy chain CDRs 1, 2, and 3 and light chain CDRs 1, 2, and 3 comprising amino acid sequences set forth in positions 31-35, 50-66, 99-104, 153-165, 182-188 and 221-230 of SEQ ID NO: 1, respectively; (b) an antibody with heavy chain CDRs 1, 2, and 3 and light chain CDRs 1, 2, and 3 comprising amino acid sequences set forth in positions 31-35, 50-66, 99-103, 152-165, 182-188 and 221-230 of SEQ ID NO: 2, respectively; (c) an antibody with heavy chain CDRs 1, 2, and 3 and light chain CDRs 1, 2, and 3 comprising amino acid sequences set forth in positions 31-35, 50-66, 99-104, 153-165, 182-188 and 221-229 of SEQ ID NO: 3, respectively; (d) an antibody with heavy chain CDRs 1, 2, and 3 and light chain CDRs 1, 2, and 3 comprising amino acid sequences set forth in positions 31-35, 50-66, 99-104, 153-165, 182-188 and 221-229 of SEQ ID NO: 4, respectively; (e) an antibody with heavy chain CDRs 1, 2, and 3 and light chain CDRs 1, 2, and 3 comprising amino acid sequences set forth in positions 31-35, 50-66, 99-104, 153-165, 182-188 and 221-229 of SEQ ID NO: 5, respectively; and (f) an antibody with heavy chain CDRs 1, 2, and 3 and light chain CDRs 1, 2, and 3 comprising amino acid sequences set forth in positions 31-35, 50-66, 99-104, 153-165, 182-188 and 221-229 of SEQ ID NO: 6, respectively, or a mutant of the antibody, which is free of a mutation in the CDRs but comprises one or several substitutions, additions, or deletions in a framework of the antibody in the mutant.

In still another embodiment, the anti-LSR antibody is an antibody selected from a monoclonal antibody, polyclonal antibody, chimeric antibody, humanized antibody, human antibody, multifunctional antibody, bispecific or oligospecific antibody, single chain antibody, scFV, diabody, sc (Fv)₂ (single chain (Fv)₂), and scFv-Fc.

That is, according to another aspect of the present invention, a therapeutic drug for malignant tumor comprising an anti-LSR antibody is provided.

Further, according to another aspect of the present invention, a therapeutic drug for malignant tumor, comprising an LSR antagonist is provided.

Further, according to another aspect of the present invention, an agent for suppressing cell division of a malignant tumor cell, comprising an anti-LSR antibody is provided.

Further, according to another aspect of the present invention, a companion diagnostic drug for malignant tumor therapy targeting an LSR, comprising an anti-LSR antibody is provided. One embodiment is characterized in that the malignant tumor is determined to be LSR positive by the companion diagnostic method of present invention, and the LSR binding agent is administered thereafter.

Further, according to another aspect of the present invention, a companion diagnostic method for malignant tumor therapy targeting an LSR, comprising inspecting whether a malignant tumor sample of a malignant tumor patient is LSR positive, is provided.

In a specific embodiment, the malignant tumor may be LSR positive malignant tumor. Further, in one embodiment of the present invention, the above-described therapeutic drug may be a therapeutic drug for administration to a patient determined to have an episode of LSR positive malignant tumor. Further, in one embodiment of the present invention, the above-described therapeutic drug may be a therapeutic drug for administration to a patient among tumor patients whose malignant tumor has been determined to be LSR positive malignant tumor. Further, in one embodiment of the present invention, the anti-LSR antibody may be an anti-LSR antibody that specifically binds to an epitope of an LSR. Further, in one embodiment of the present invention, the anti-LSR antibody may be one or more antibodies selected from the group consisting of: (a) an antibody with heavy chain CDRs 1, 2, and 3 and light chain CDRs 1, 2, and 3 comprising amino acid sequences set forth in positions 31-35, 50-66, 99-104, 153-165, 182-188 and 221-230 of SEQ ID NO: 1, respectively; (b) an antibody with heavy chain CDRs 1, 2, and 3 and light chain CDRs 1, 2, and 3 comprising amino acid sequences set forth in positions 31-35, 50-66, 99-103, 152-165, 182-188 and 221-230 of SEQ ID NO: 2, respectively; (c) an antibody with heavy chain CDRs 1, 2, and 3 and light chain CDRs 1, 2, and 3 comprising amino acid sequences set forth in positions 31-35, 50-66, 99-104, 153-165, 182-188 and 221-229 of SEQ ID NO: 3, respectively; (d) an antibody with heavy chain CDRs 1, 2, and 3 and light chain CDRs 1, 2, and 3 comprising amino acid sequences set forth in positions 31-35, 50-66, 99-104, 153-165, 182-188 and 221-229 of SEQ ID NO: 4, respectively; (e) an antibody with heavy chain CDRs 1, 2, and 3 and light chain CDRs 1, 2, and 3 comprising amino acid sequences set forth in positions 31-35, 50-66, 99-104, 153-165, 182-188 and 221-229 of SEQ ID NO: 5, respectively; and (f) an antibody with heavy chain CDRs 1, 2, and 3 and light chain CDRs 1, 2, and 3 comprising amino acid sequences set forth in positions 31-35, 50-66, 99-104, 153-165, 182-188 and 221-229 of SEQ ID NO: 6, respectively, or a mutant of the antibody, which is free of a mutation in the CDRs but comprises one or several substitutions, additions, or deletions in a framework of the antibody in the mutant. These antibodies may be an antibody selected from a monoclonal antibody, polyclonal antibody, chimeric antibody, humanized antibody, human antibody, multifunctional antibody, bispecific or oligospecific antibody, single chain antibody, scFV, diabody, sc(Fv)₂ (single chain (Fv)₂), and scFv-Fc. The antibodies used are not limited, but an antibody having positions 116-134 and/or 216-230 of SEQ ID NO: 7 as an epitope can be advantageously used. This is because an advantageous effect as well as safety and stability thereof are demonstrated herein.

Further, in a specific embodiment of the present invention, the above-described anti-LSR antibody may be a monoclonal antibody. Further, in one embodiment of the present invention, an antibody class of the above-described anti-LSR antibody may be IgG. Further, in one embodiment of the present invention, the above-described anti-LSR antibody may be the antigen binding fragment. Further, in one embodiment of the present invention, the above-described LSR antagonist may be an RNAi molecule directed to an LSR or a polynucleotide encoding the RNAi molecule.

In another aspect of the present invention, the present invention provides a poor prognosis marker for malignant tumor therapy, comprising an LSR (lipolysis stimulated lipoprotein receptor) binding agent. It is understood that a binding agent in any form of the present invention explained herein can be used as the binding agent used in this aspect. For example, the binding agent may be an antibody, a fragment or a functional equivalent thereof, or a nucleic acid, which may be labeled.

In another aspect of the present invention, the present invention provides a method of using an expression level of an LSR (lipolysis stimulated lipoprotein receptor) as an indicator for poor prognosis of malignant tumor therapy. It is understood that a binding agent in any form of the present invention explained herein can be used as the binding agent used in this aspect. For example, the binding agent may be an antibody, a fragment or a functional equivalent thereof, or a nucleic acid, which may be labeled.

In another aspect of the present invention, the present invention provides a diagnostic agent for poor prognosis of malignant tumor therapy, comprising an LSR (lipolysis stimulated lipoprotein receptor) binding agent. It is understood that a binding agent in any form of the present invention explained herein can be used as the binding agent used in this aspect. For example, the binding agent may be an antibody, a fragment or a functional equivalent thereof, or a nucleic acid, which may be labeled.

In still another aspect, the present invention provides a therapeutic method, prophylactic method, use and the like using a pharmaceutical composition, therapeutic agent or prophylactic agent of the present invention.

It is understood that one or more of the aforementioned features can be further combined for use.

Those skilled in the art who have read and understood the following Detailed Description as needed would recognize further embodiments and advantages of the present invention.

Advantageous Effects of Invention

According to the present invention, a novel therapeutic drug, diagnostic drug or the like for malignant tumor is obtained.

Figure 2:
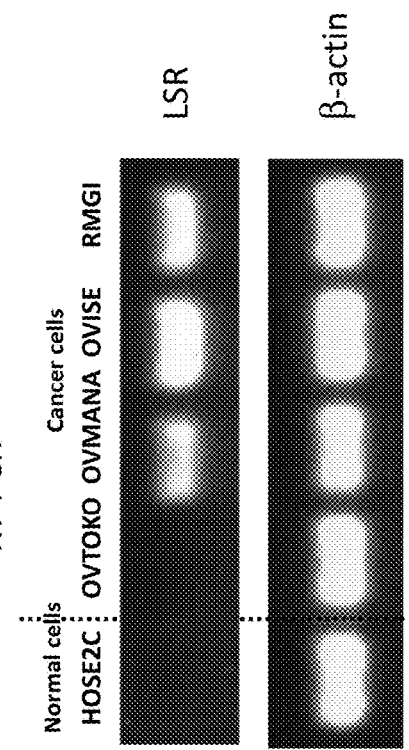

FIG. 2 is a diagram showing results of RT-PCR performed on nucleic acids obtained from ovarian clear cell adenocarcinoma cell strains. One on the left show normal cells (HOSE2C on the left side). Four on the right show cancer cells (from the left: OVTOKO, OVMANA, OVISE, and RMG-1). The top row shows LSRs and the bottom row shows the background β actin.

Figure 3:
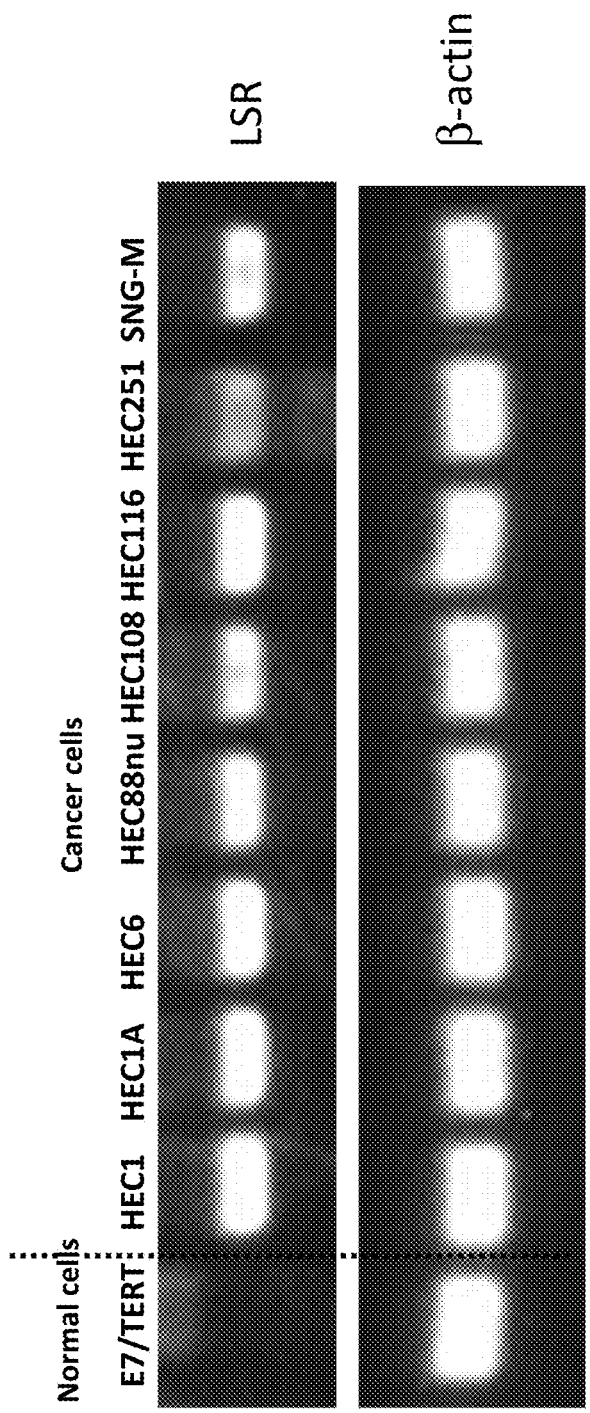

FIG. 3 is a diagram showing results of RT-PCR performed on nucleic acids obtained from endometrial cancer cell strains. The left end shows normal cells (E6/E7/TERT), and the others are cancer cells (from the left: HEC1, HEC1A, HEC6, HEC88nu, HEC108, HEC116, HEC251, and SMG-M). The top row shows LSRs and the bottom row shows the background β actin.

Figure 4:
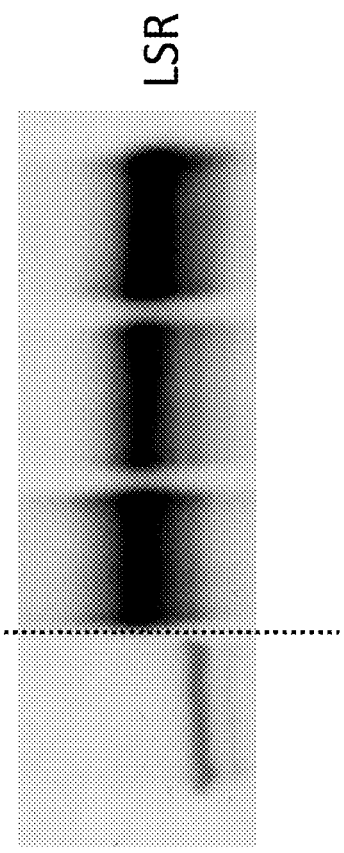

FIG. 4 is a diagram showing results of Western blot performed on proteins obtained from ovarian serous adenocarcinoma cell strains. One on the left show normal cells (HOSE2C on the left side). Three on the right show cancer cells (from the left: OVCAR3, OVSAHO, and JHOS4).

Figure 5:
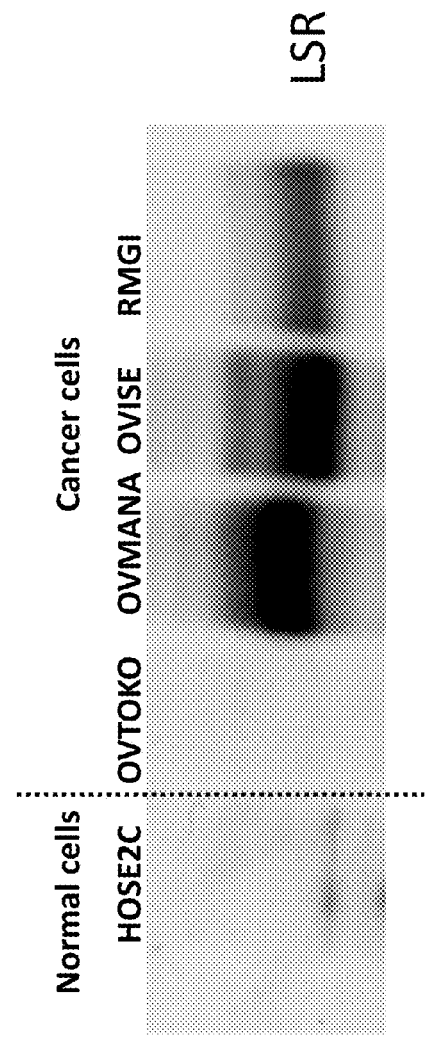

FIG. 5 is a diagram showing results of Western blot performed on proteins obtained from ovarian clear cell adenocarcinoma cell strains. One on the left show normal cells (HOSE2C on the left side). Four on the right show cancer cells (from the left: OVTOKO, OVMANA, OVISE, and RMG-1).

Figure 6:
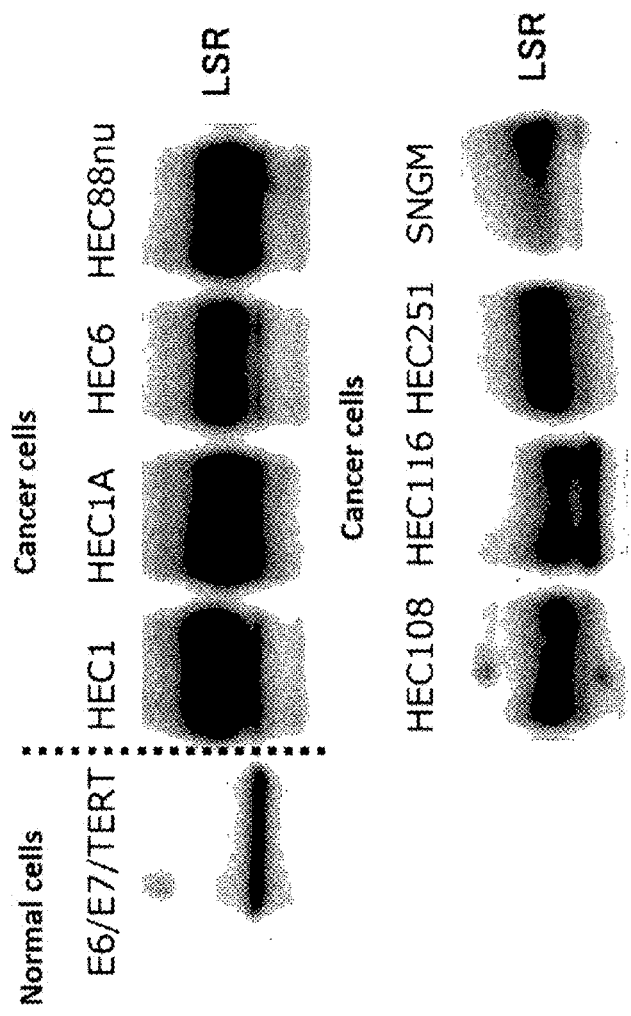

FIG. 6 is a diagram showing results of Western blot performed on proteins obtained from endometrial cancer cell strains. The top left end shows normal cells (E6/E7/TERT), and others are cancer cells. The top row shows, from the left, HEC1, HEC1A, HEC6, and HEC88nu. The bottom row shows from the left, HEC108, HEC116, HEC251, and SMG-M. All of them represent LSRs.

Figure 7:
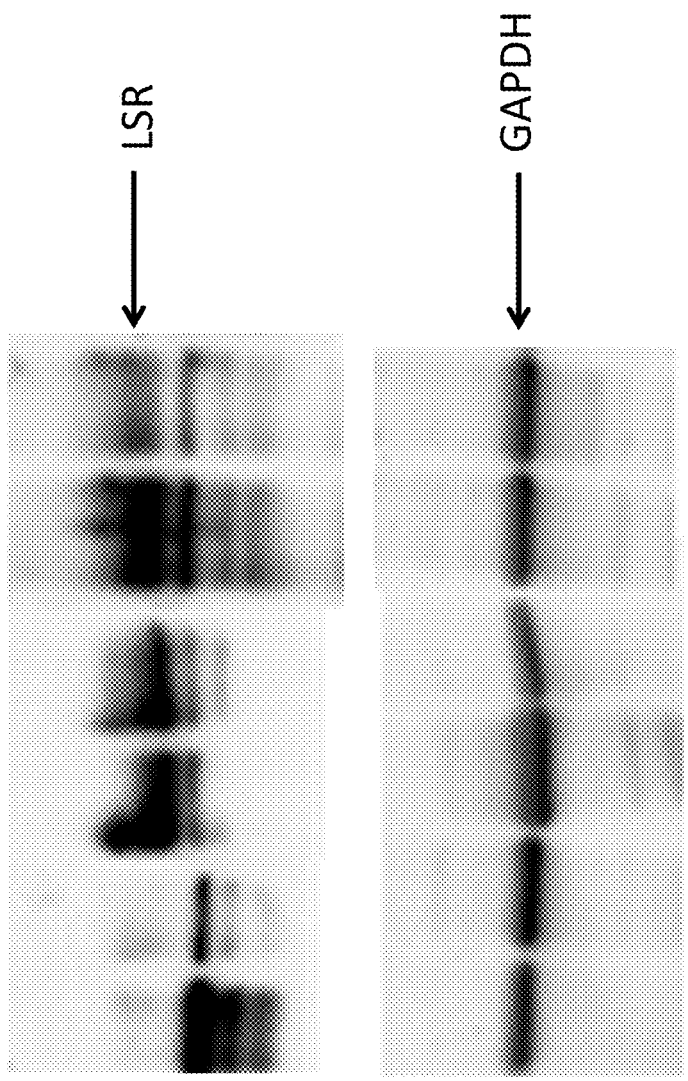

FIG. 7 is a diagram showing results of Western blot performed on proteins obtained from tissue on which surgery has been performed for ovarian serous adenocarcinoma and tissue on which surgery has been performed for ovarian clear cell adenocarcinoma. The Figure shows, from the left, two samples from normal (healthy individual's) ovaries (No. 1 and No. 2=represented by (1) and (2)), two samples from clear cell adenocarcinoma patients (No. 1 and No. 2=represented by (3) and (4)), and two samples from serous adenocarcinoma patients (No. 1 and No. 2=represented by (5) and (6)).

Figure 8:
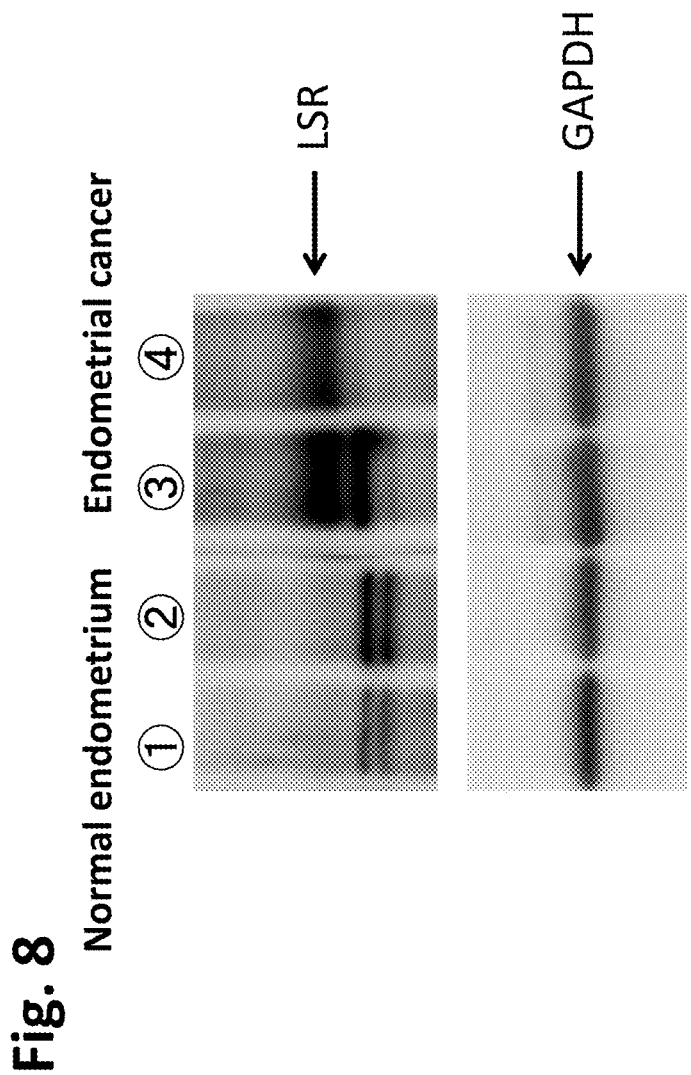

FIG. 8 is a diagram showing results of Western Blot performed on proteins obtained from tissue on which surgery has been performed for endometrial cancer. The Figure shows, from the left, two samples from normal (healthy individual's) ovaries (No. 1 and No. 2=represented by (1) and (2)), and two samples from endometrial cancer patients (No. 1 and No. 2=represented by (3) and (4)).

FIG. 9 is a diagram showing the amino acid sequence of the anti-LSR antibody described in the Examples.

Figure 10:
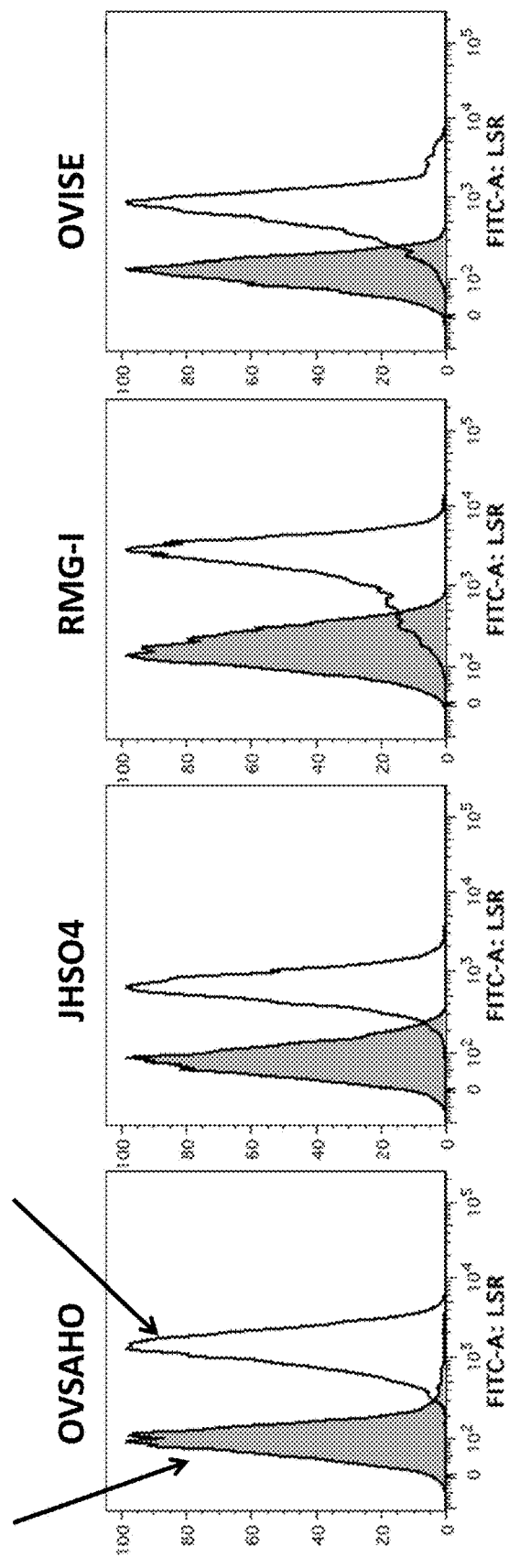

FIG. 10 is a diagram showing results of assessing reactivity of #9-7 antibody to, from the left, OVSAHO, JHSO4, RMG-I, and OVISE. The vertical axis indicates intensity and the horizontal axis indicates cell frequency.

Figure 11:
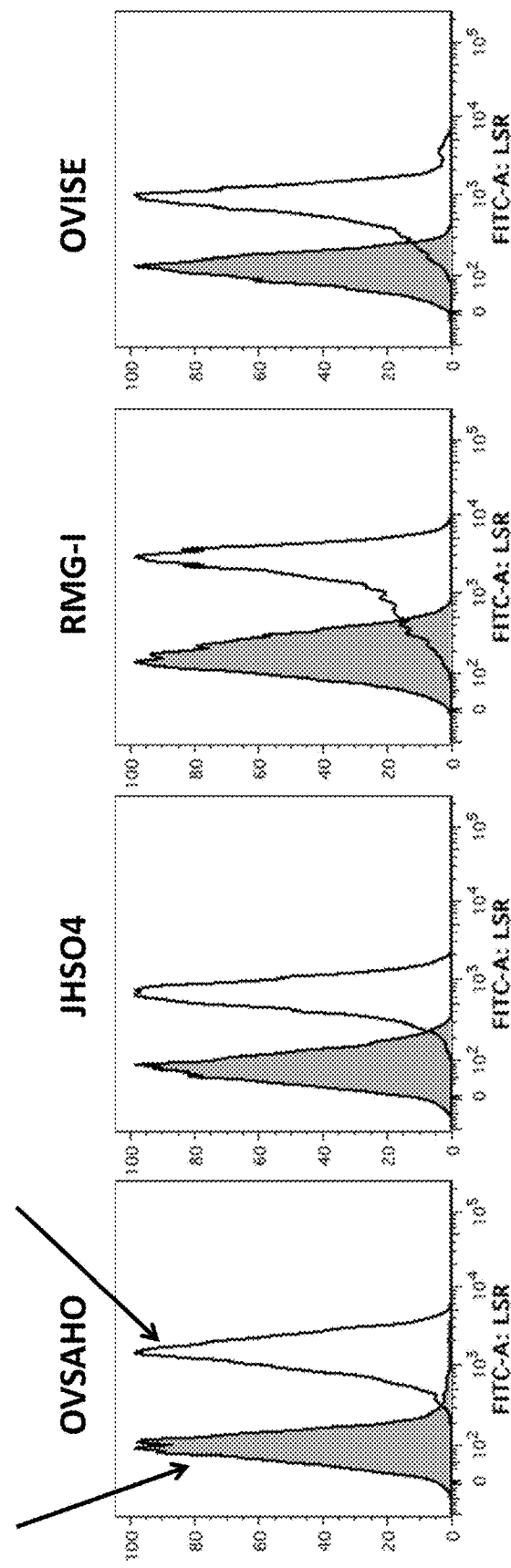

FIG. 11 is a diagram showing results of assessing reactivity of #16-6 antibody to, from the left, OVSAHO, JHSO4, RMG-I, and OVISE. The vertical axis indicates intensity and the horizontal axis indicates cell frequency.

Figure 12:
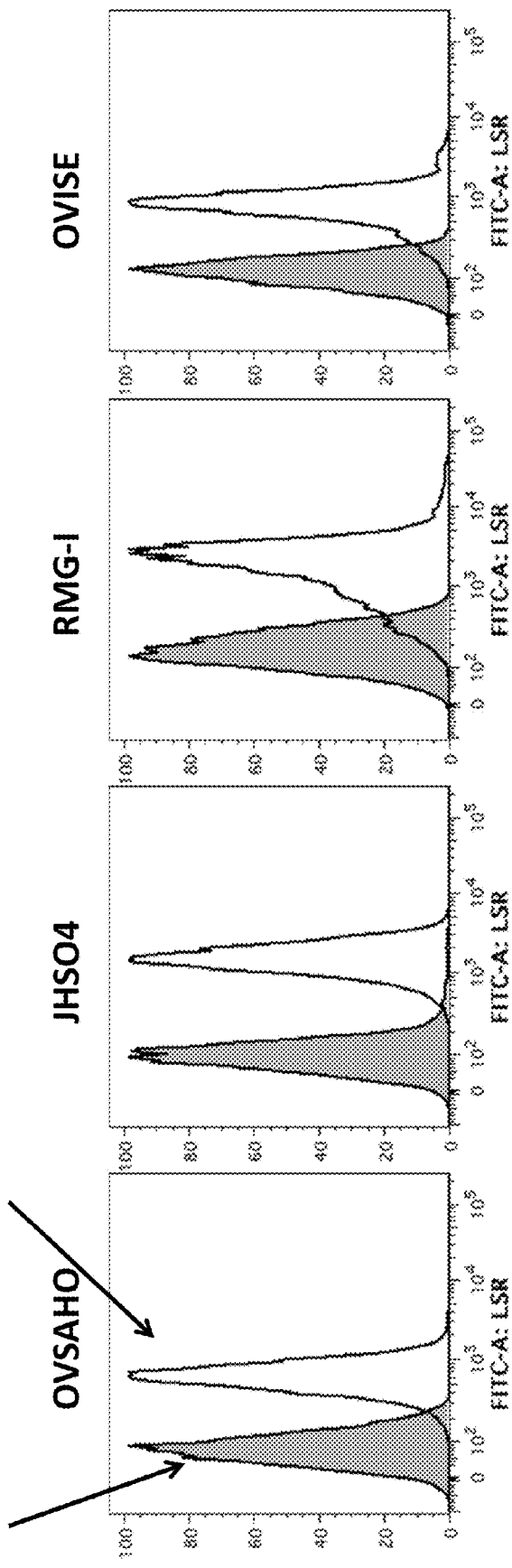

FIG. 12 is a diagram showing results of assessing reactivity of #26-2 antibody to, from the left, OVSAHO, JHSO4, RMG-I, and OVISE. The vertical axis indicates intensity and the horizontal axis indicates cell frequency.

Figure 13:
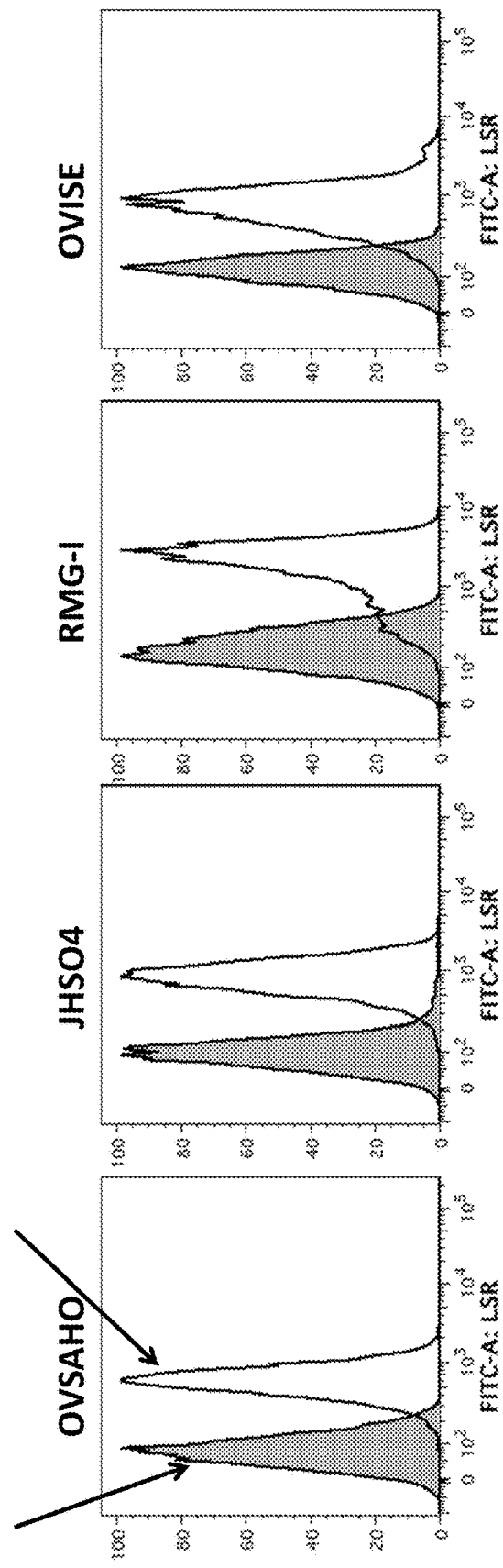

FIG. 13 is a diagram showing results of assessing reactivity of #27-6 antibody to, from the left, OVSAHO, JHSO4, RMG-I, and OVISE. The vertical axis indicates intensity and the horizontal axis indicates cell frequency.

Figure 14:
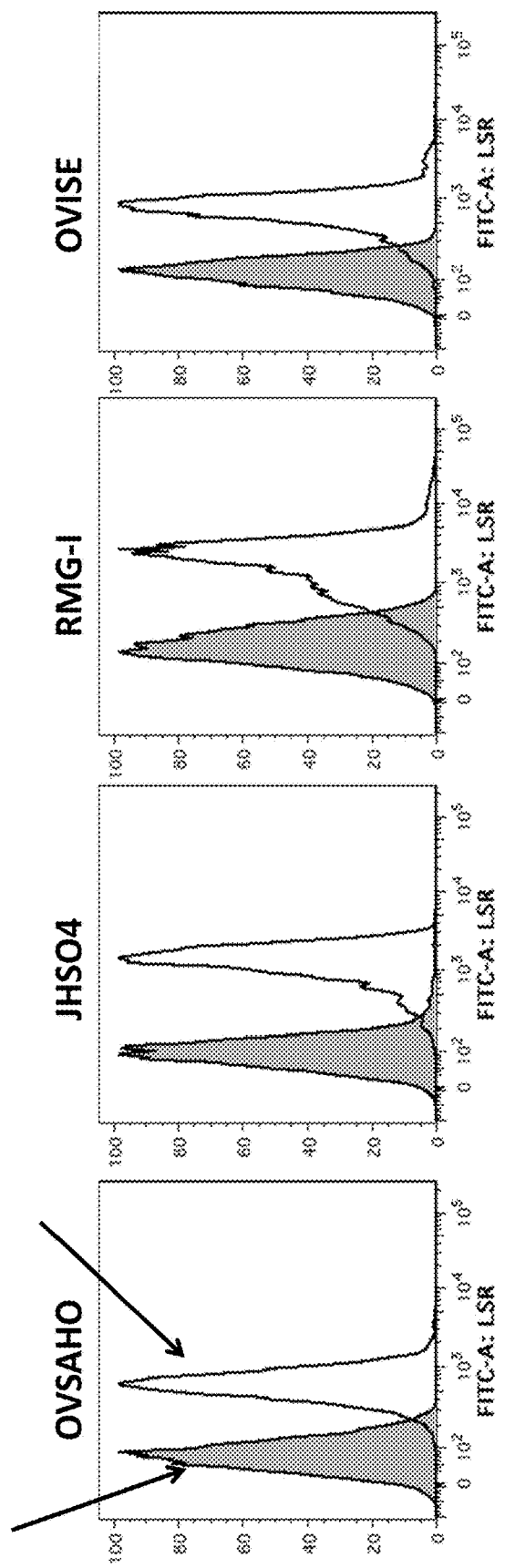

FIG. 14 is a diagram showing results of assessing reactivity of #1-25 antibody to, from the left, OVSAHO, JHSO4, RMG-I, and OVISE. The vertical axis indicates intensity and the horizontal axis indicates cell frequency.

Figure 15:
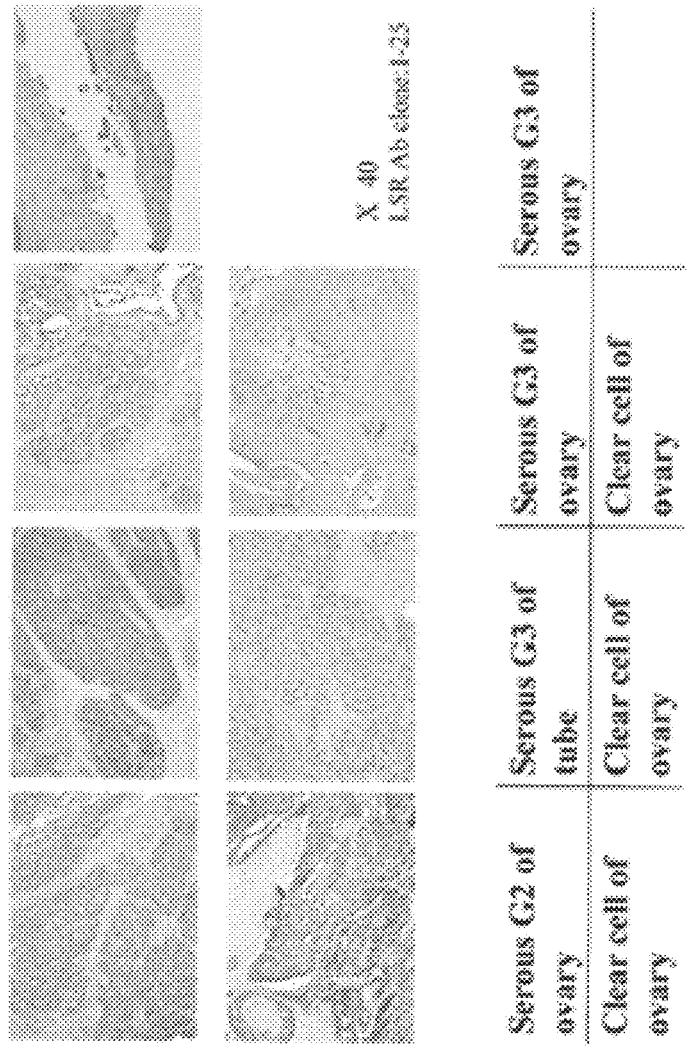

FIG. 15 is a diagram showing a result of analyzing ovarian serous adenocarcinoma tissue for expression of LSRs by an immunohistochemical staining method using monoclonal the antibody #1-25. The top row shows serous G2 of ovary, serous G3 of tube, serous G3 of ovary and serous G3 of ovary. All pictures in the bottom row show a clear cell of ovary.

Figure 16:
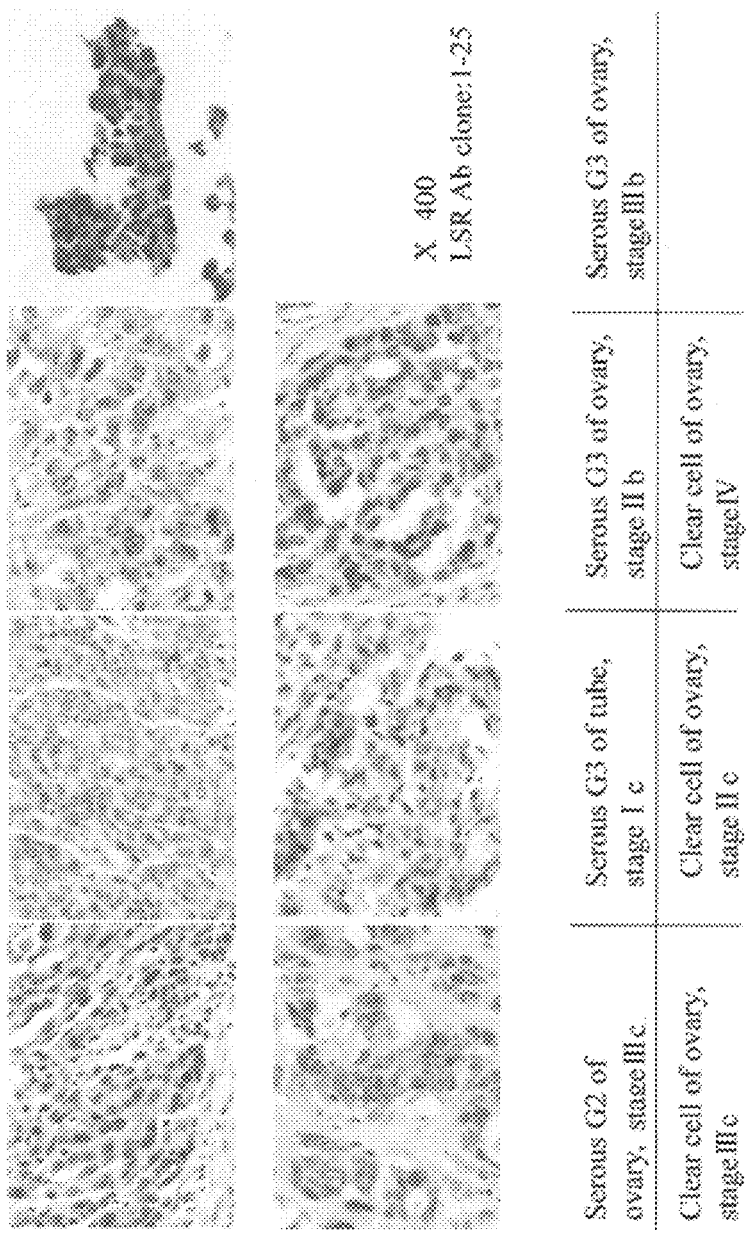

FIG. 16 is a diagram showing a result of analyzing ovarian serous adenocarcinoma tissue for expression of LSRs by an immunohistochemical staining method using monoclonal antibodies #1-25. The top row shows stage IIIc of serous G2 of ovary, stage Ic of serous G3 of tube, stage IIb of serous G3 of ovary, and stage IIIb of serous G3 of ovary. The bottom row shows, from the left, stage IIIc of clear cell of ovary, stage IIc of clear cell of ovary, and stage IV of clear cell of ovary.

Figure 17:
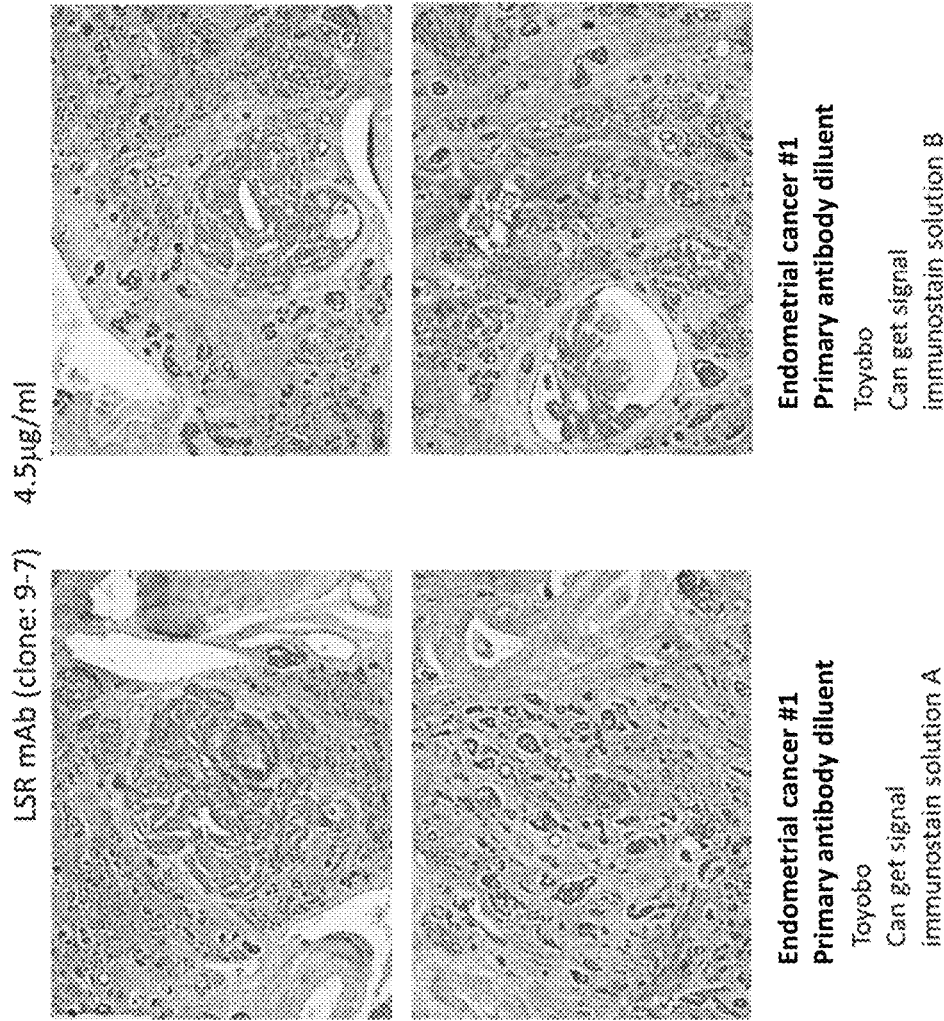

FIG. 17 is a diagram showing a result of analyzing endometrial cancer tissue for expression of LSRs by an immunohistochemical staining method using monoclonal antibodies #9-7 (4.5 µg/ml). The left side is endometrial cancer #1 applied with Toyobo Can get signal immunostain solution A as the primary antibody diluent, and the right is endometrial cancer #1 applied with Toyobo Can get signal immunostain solution B as the primary antibody diluent.

Figure 18:
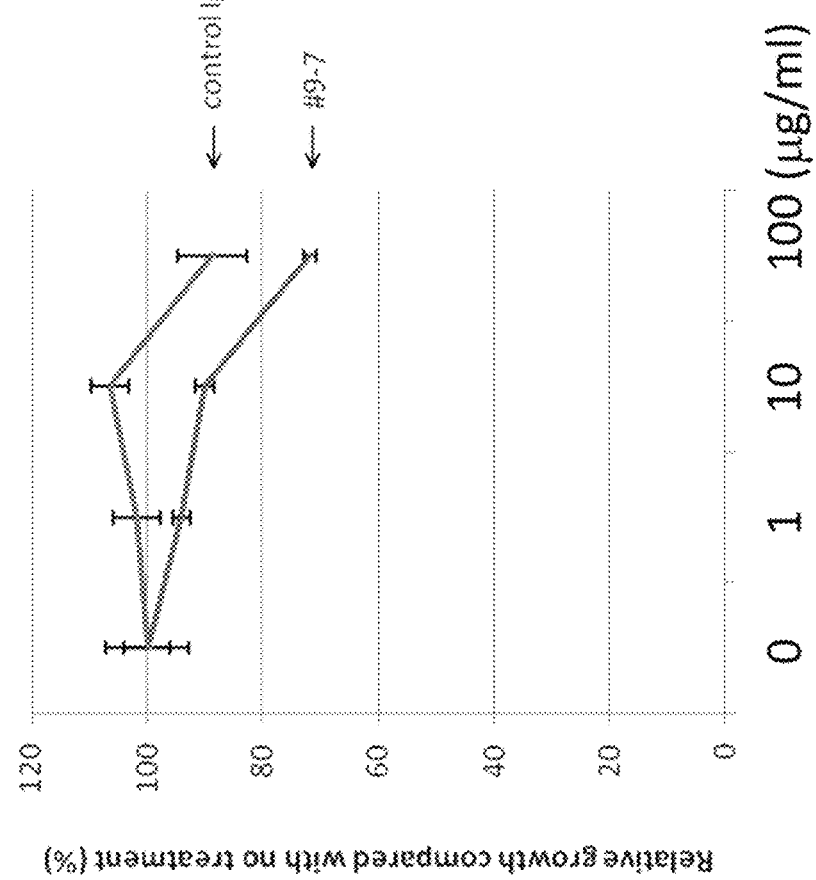

FIG. 18 is a diagram showing results of assessing #9-7 antibody for the effect of suppressing growth of RMG-I. The vertical axis indicates relative growth compared with no treatment. The horizontal axis is the dosage of IgG.

Figure 19:
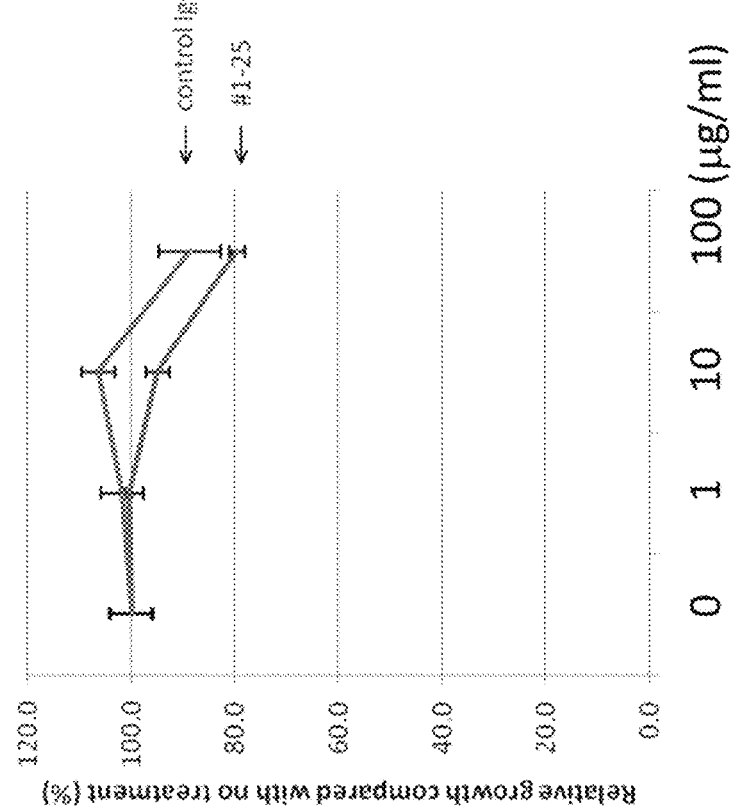

FIG. 19 is a diagram showing results of assessing #1-25 antibody for the effect of suppressing growth of RMG-I. The vertical axis indicates relative growth compared with no treatment. The horizontal axis is the dosage of IgG.

Figure 20:
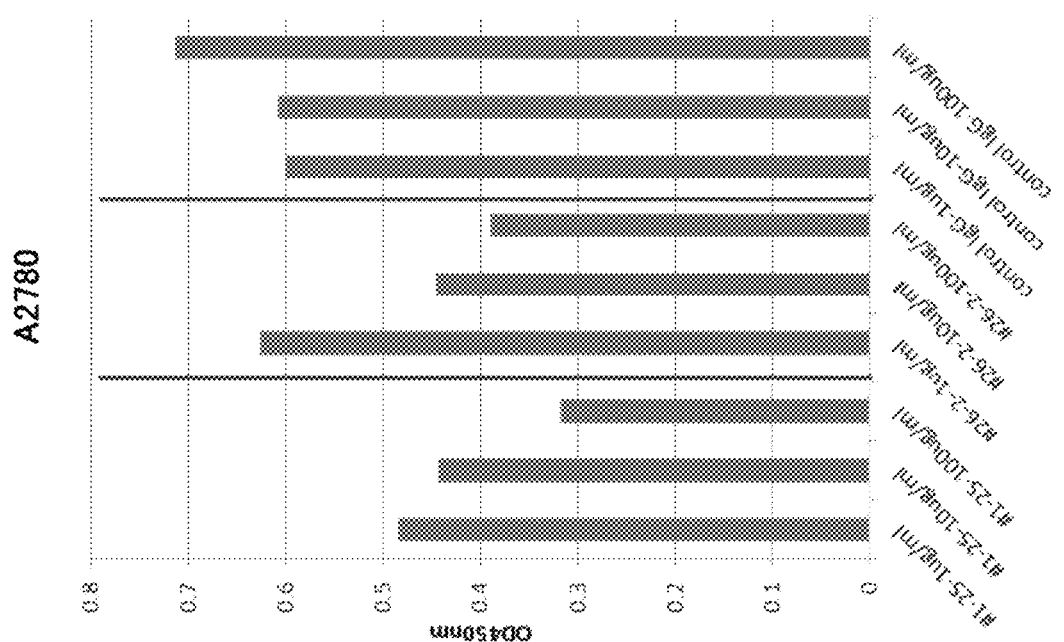

FIG. 20 is a diagram showing results of assessing #1-25 antibody (the left three; from the left, 1 µg/ml, 10 µg/ml, and 100 µg/ml, respectively) and #26-2 antibody (middle three; from the left, 1 µg/ml, 10 µg/ml, and 100 µg/ml, respectively) for the effect of suppressing growth of A2780. The control IgG is shown on the right (right three; from the left, 1 µg/ml, 10 µg/ml, and 100 µg/ml, respectively). Each antibody has an effect, but #1-25 exhibited a stronger effect than #26-2.

Figure 21:
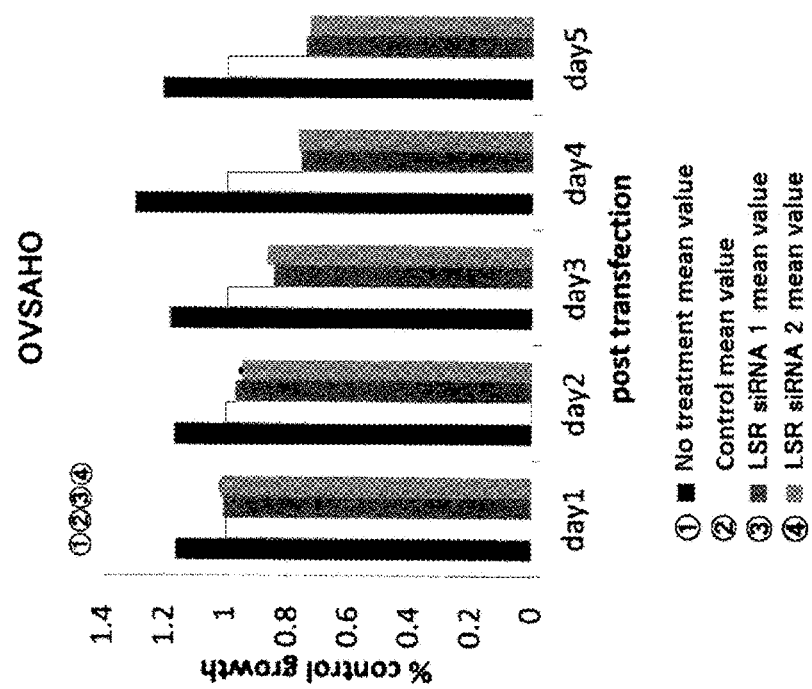

FIG. 21 is a diagram showing results of assessing the LSR siRNA described in the Examples for the effect of suppressing growth of OVSAHO. From the left, day 1, day 2, day 3, day 4, and day 5 are shown. 4 bars for each day indicate, from the left, mean amount with no treatment, mean value of control, mean value of LSR siRNA 1, and mean value of LSR siRNA2.

Figure 22:
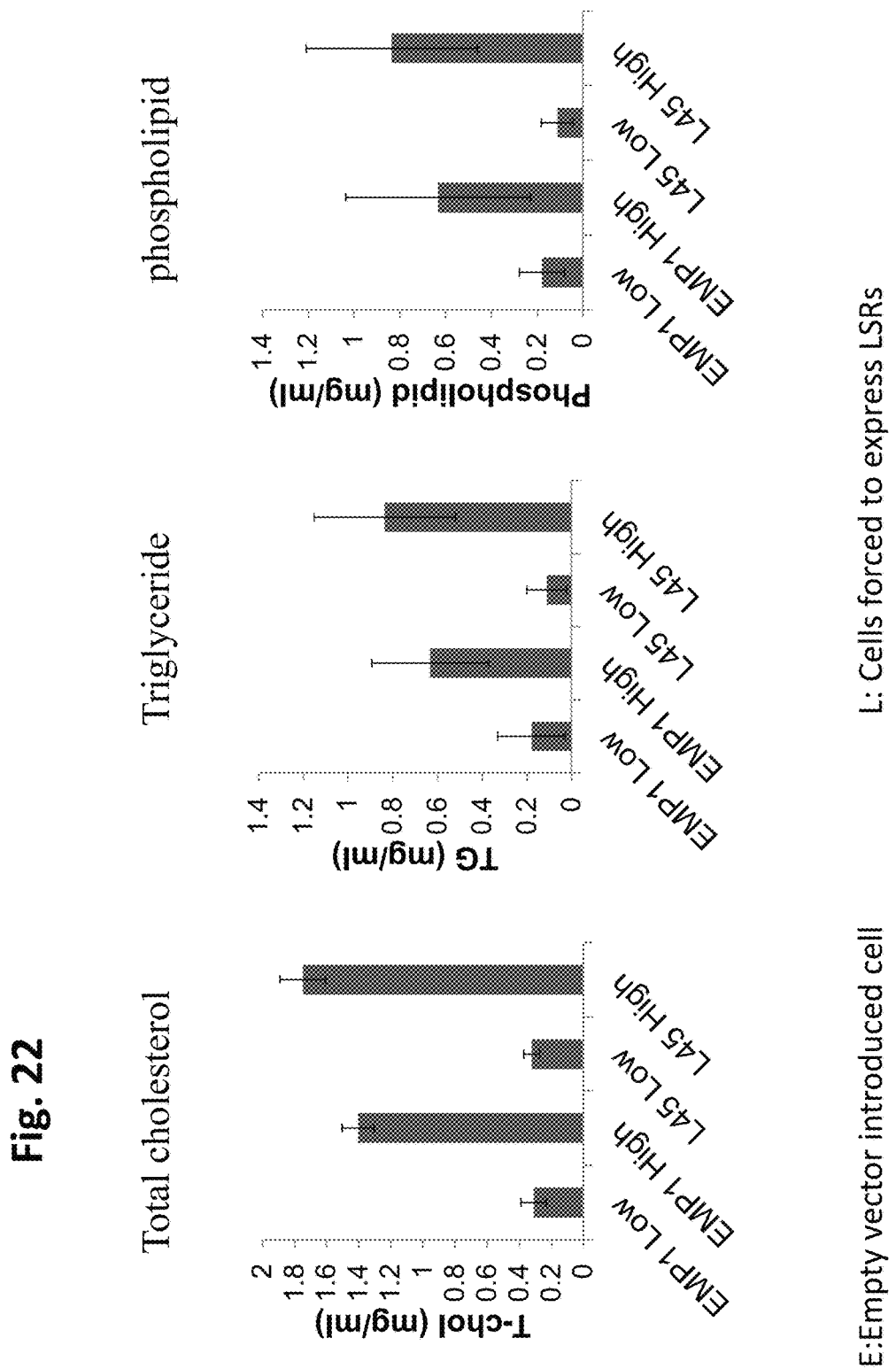

FIG. 22 is a diagram of a result showing that lipid (cholesterol) incorporation is elevated in the cells stably expressing LSRs described in the Examples. The left shows the effects on total cholesterol, the middle graph shows the effects on triglyceride, and the right shows the effects on phospholipid. The vertical axis indicates each incorporation (mg/ml). The horizontal axis indicates each of EMP1 low density, EMP1 high density, L45 low density, and L45 high density. EMP indicates empty vector introduced cells and L indicates cells forced to express LSRs.

Figure 23:
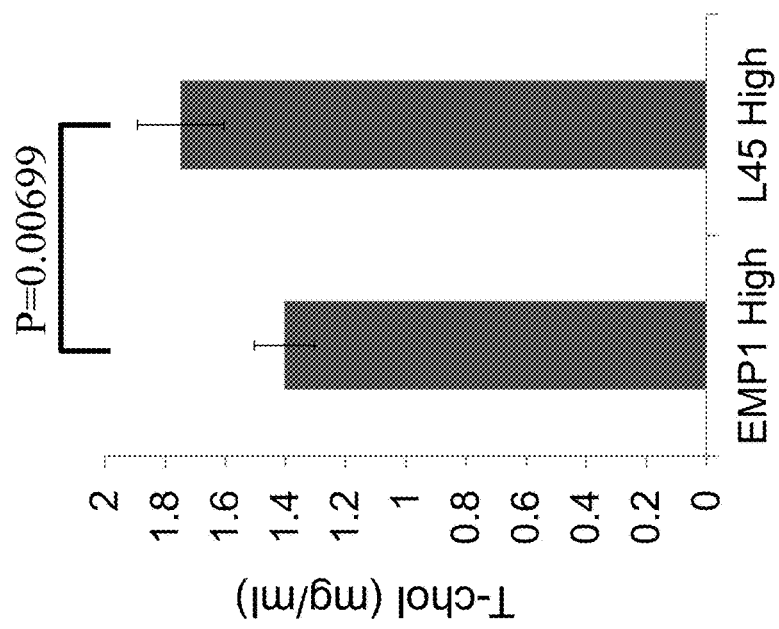

FIG. 23 is a diagram of a result showing that lipid (cholesterol) incorporation is elevated in high density culture in the cells stably expressing LSRs described in the Examples. The vertical axis indicates total cholesterol incorporation (mg/ml). EMP1 indicates empty vector introduced cells and L45 indicates cells forced to express LSRs.

Figure 24:
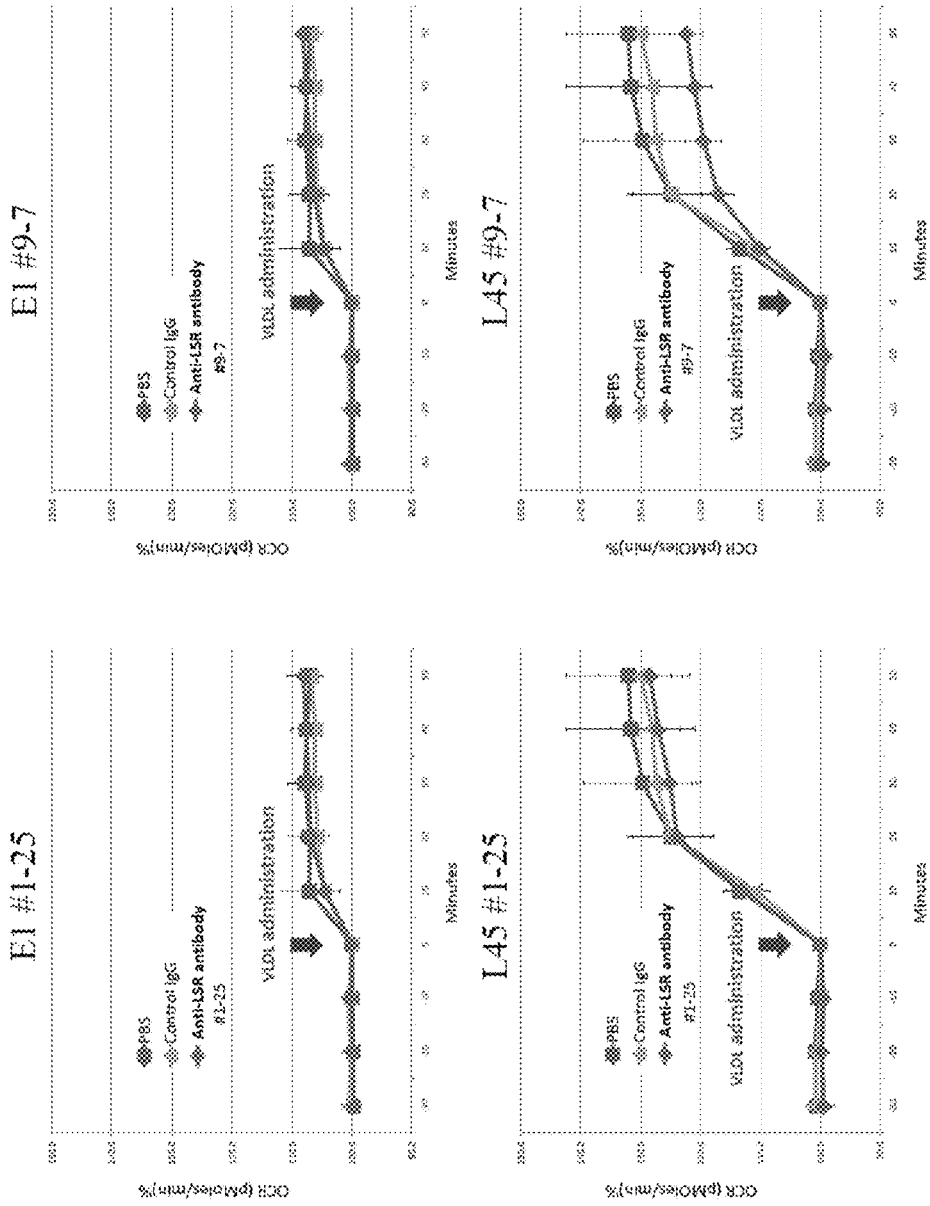

FIG. 24 is a diagram of a result showing that LSR expression described in the Examples elevates VLDL metabolism, but elevation in metabolism due to VLDL is inhibited by LSR antibody administration. Significantinhibition of elevation in metabolism due to VLDL is exhibited for #9-7. Slight inhibition is also observed for the #1-25 antibody. In each graph, the vertical axis is OCR (pMoles/min) % and the horizontal axis indicates the elapsed time (minutes). Squares indicate PBS (background control), triangles indicate the control IgG, and rhombuses indicate anti-LSR antibodies. The top panel is for empty vector (E1) and the bottom is for cells forced to express LSRs (L45).

Figure 25:
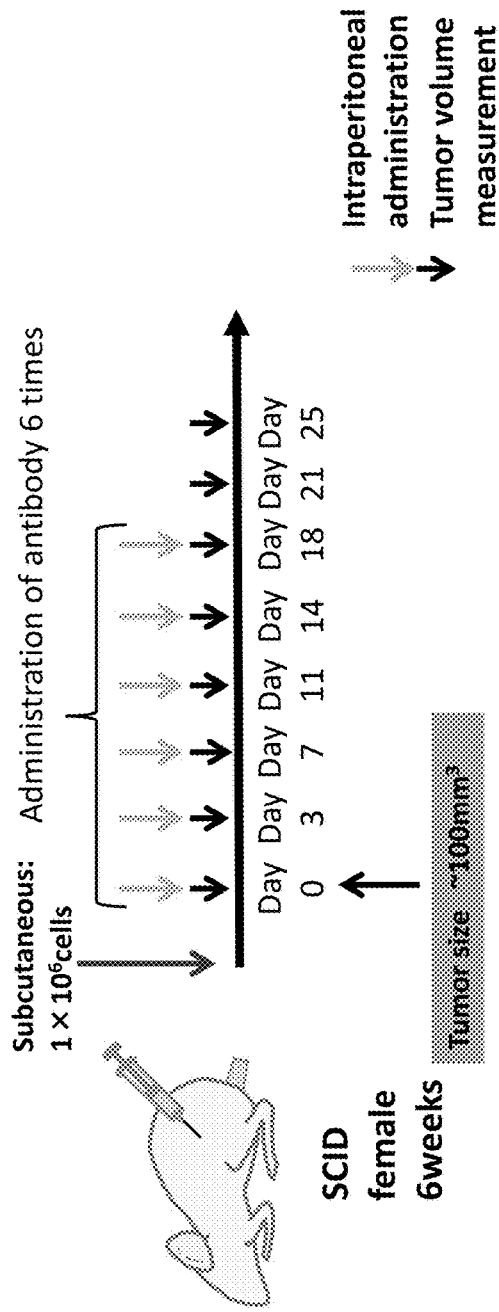

FIG. 25 is a diagram showing the condition when the anti-LSR antibody described in the Examples was administered to a malignant tumor model mouse.

Figure 26:
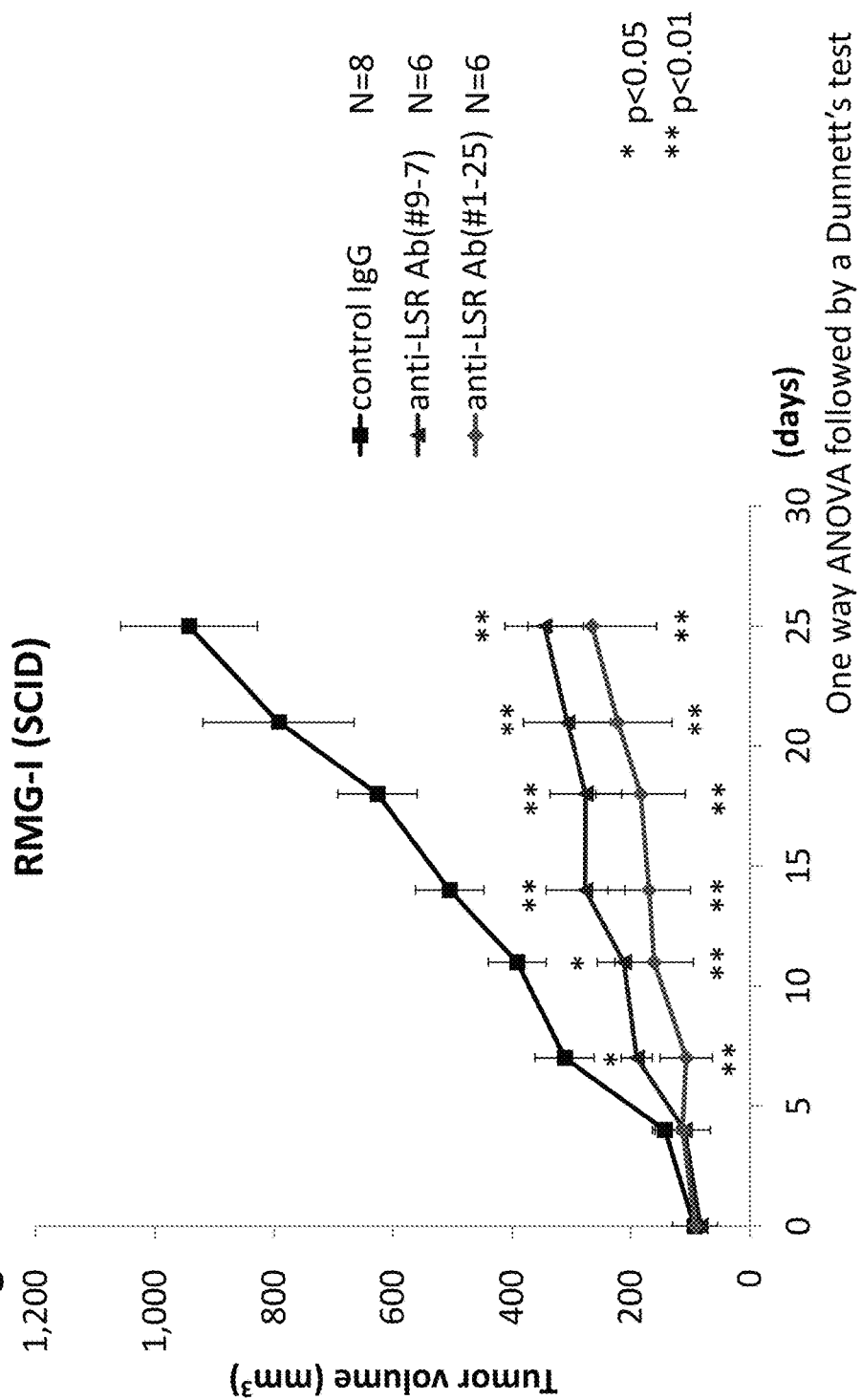

FIG. 26 is a diagram showing results of assessing the anti-LSR antibody described in the Examples for the anti-tumor effect after administration of #9-7 or #1-25 to a malignant tumor model mouse. The vertical axis indicates tumor volume (mm$^3$). The horizontal axis indicates the number of elapsed days. Squares indicate the control IgG, triangles indicate anti-LSR antibody (#9-7), and rhombuses indicate anti-LSR antibody (#1-25).

Figure 27:
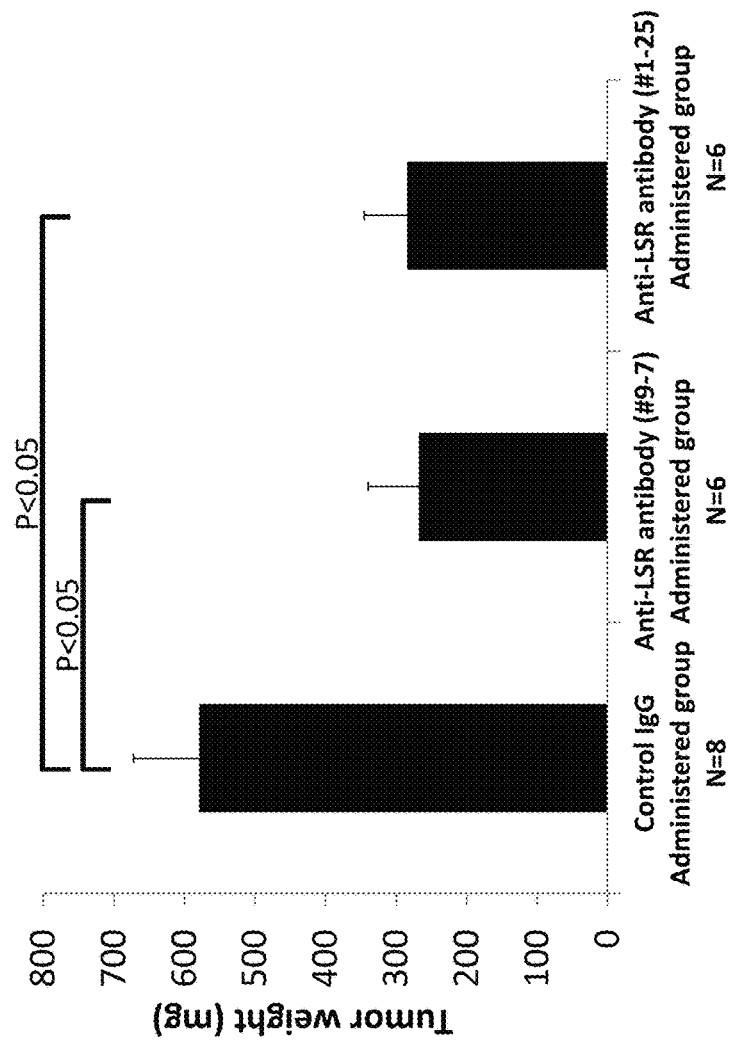

FIG. 27 is a diagram showing results of assessing the anti-LSR antibody described in the Examples for the anti-tumor effect after administration of #9-7 or #1-25 to a malignant tumor model mouse. The vertical axis indicates tumor weight (mg). From the left, control IgG administered group (n=8), anti-LSR antibody (#9-7) administered group (n=6), and anti-LSR antibody (#1-25) administered group (n=6) are shown.

Figure 28:
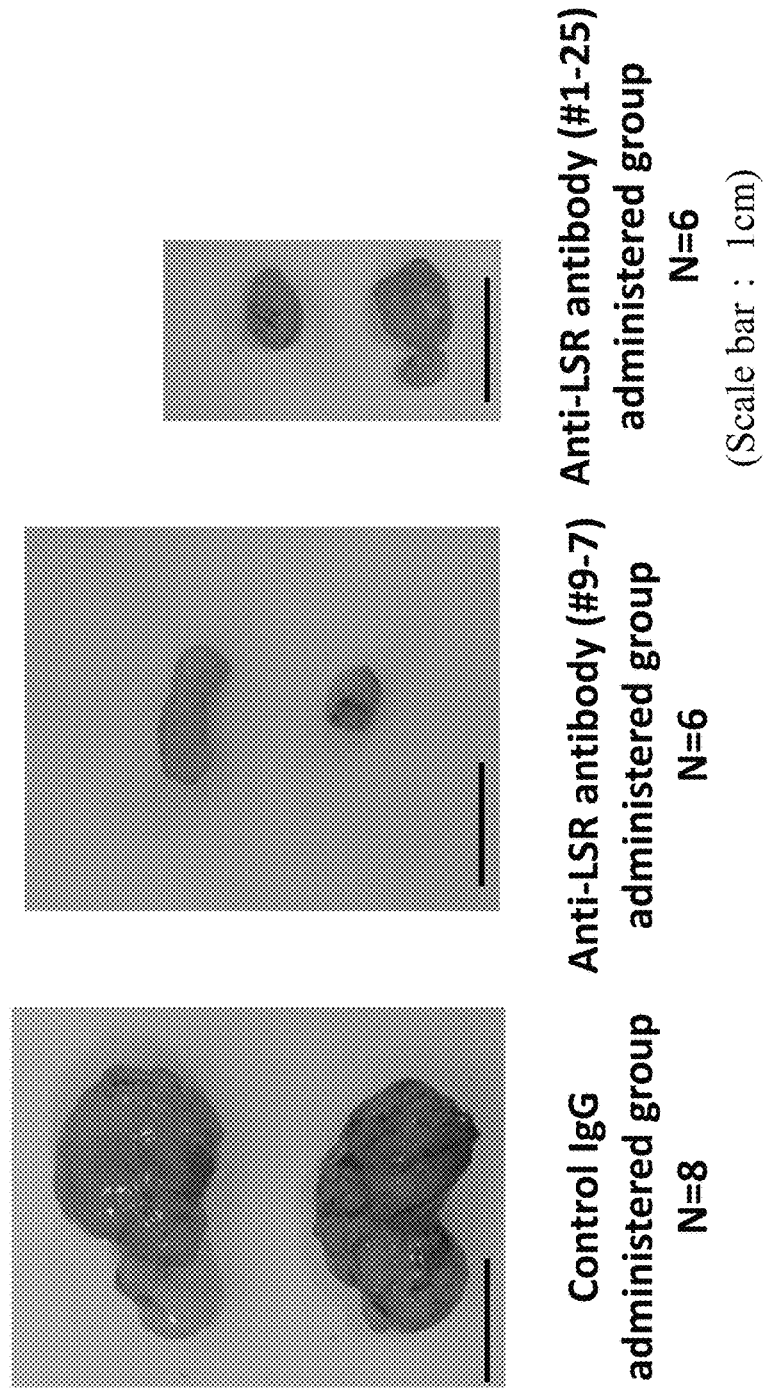

FIG. 28 is a diagram showing results of assessing the anti-LSR antibody described in the Examples for the anti-tumor effect after administration of #9-7 or #1-25 to a malignant tumor model mouse. From the left, control IgG administered group (n=8), anti-LSR antibody (#9-7) administered group (n=6), and anti-LSR antibody (#1-25) administered group (n=6) are shown.

Figure 29:
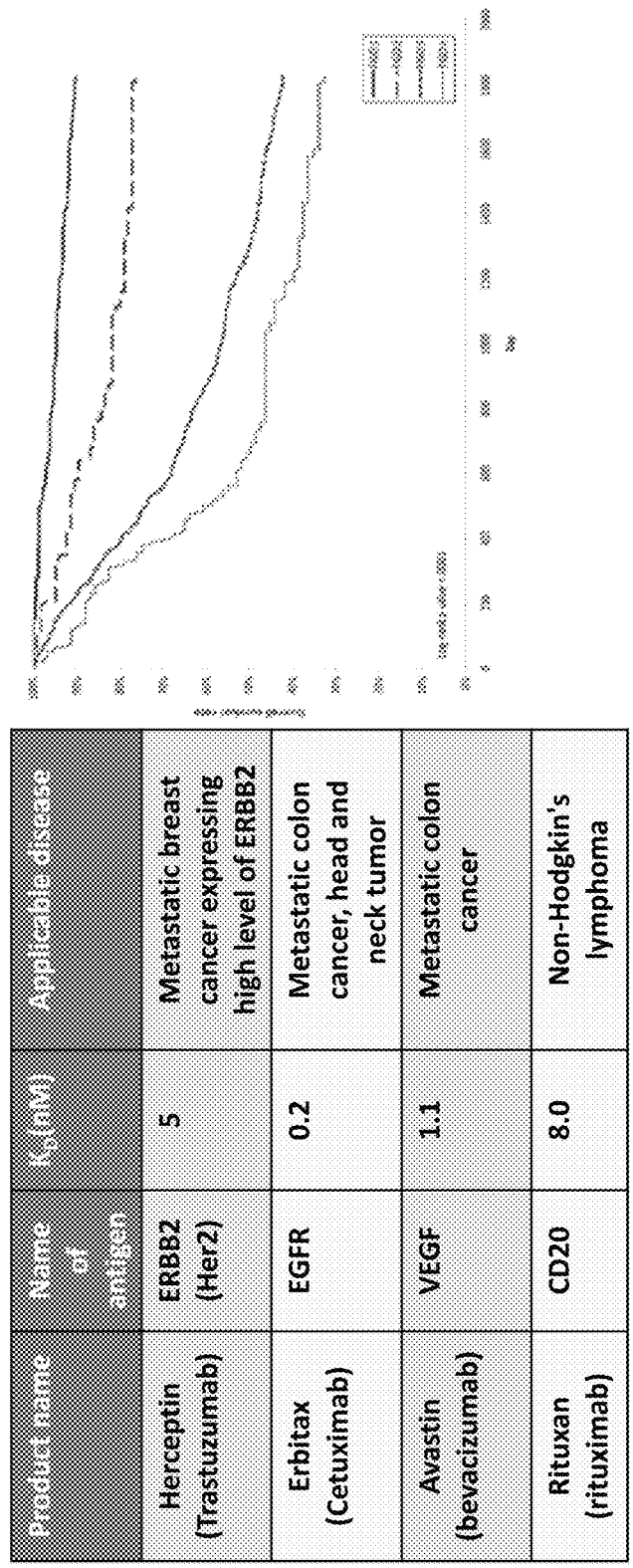

FIG. 29 shows that recurrent ovarian cancer does not have an effective therapeutic method. Conventionally, there was no effective therapeutic method for recurrent ovarian cancer. The epidemiological characteristic of ovarian cancer is that ovarian cancer readily infiltrate into the surrounding by the lymph node and peritoneal metastasis or the like and advances quickly. For instance, 40% or more of ovarian cancer in Japanese patients is considered serous, 24% clear cells, 17% endometrioid, and 13% mucinous adenocarcinoma. As a 1st line of defense, cisplatin or taxol is used, and Avastin is used for recurrent ovarian cancer. However, it was considered that improvement in survival rate was not observed. Since a therapeutic method during the progression stage or recurrence is non-existent, ovarian cancer was considered as tumor with poor prognosis. Thus, development of a novel therapeutic method is considered imperative. The Table on the left shows antibody medicaments approved as a cancer therapeutic drug (Carter P J Nat. Rev. Immunol. 006, May 6(5) 343-357, Review). The graph on the right side of FIG. 29 shows the 5 year survival rate (31% in Stage IV) (Japanese Society of Obstetrics and Gynecology, Fujinka Shuyo Iinkai Hokoku [*Gynecology tumor committee report*], 2012, Vol. 64, No. 6).

Figure 30:
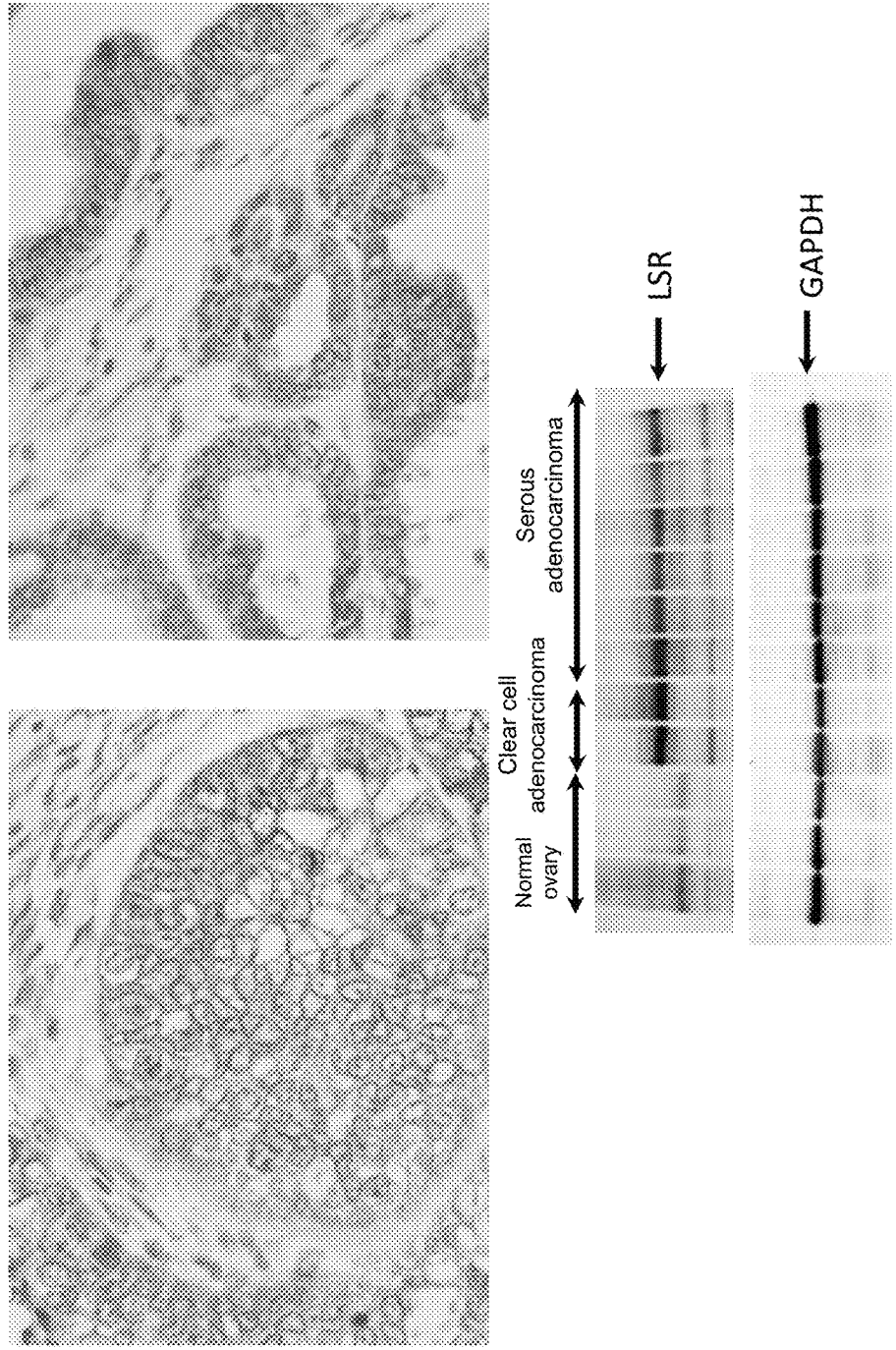

FIG. 30 is an immunostaining diagram showing that LSRs are expressed in ovarian cancer tissue. The left shows ovarian serous adenocarcinoma and the right shows ovarian clear cell adenocarcinoma. The bottom panel shows Western blot of each cell. The left three columns show normal ovary, columns 4-5 from the left show clear cell adenocarcinoma, and column 6 from the left to the right end show serous adenocarcinoma. LSR indicates the band of LSRs, and GAPDH indicates the control.

Figure 31:
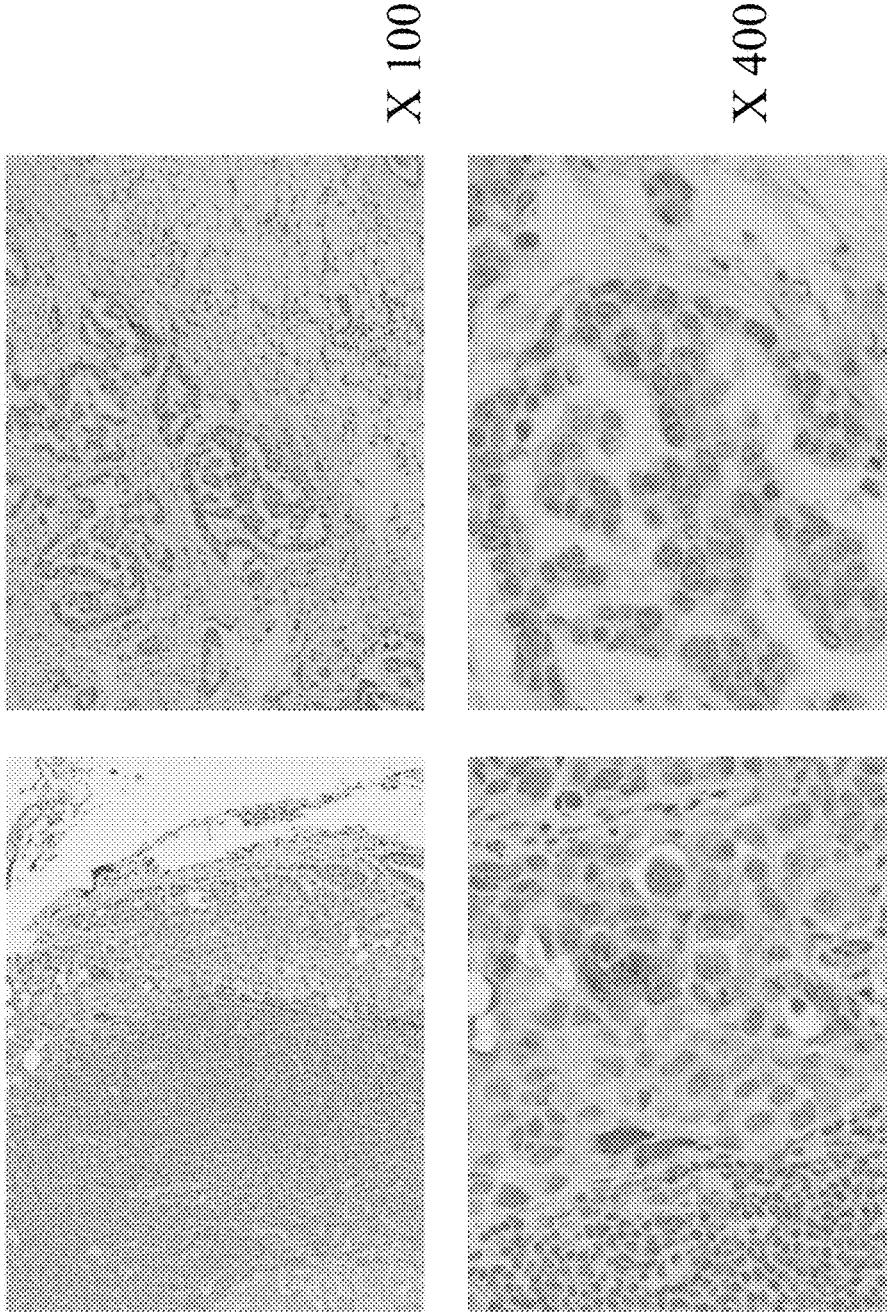

FIG. 31 is a diagram showing that LSRs are also expressed in ovarian cancer metastasized sites. The left column shows lymph node metastasis and the right column shows greater omentum metastasis. The top panel shows 100 times magnification and the bottom panel shows 400 times magnification.

Figure 32:
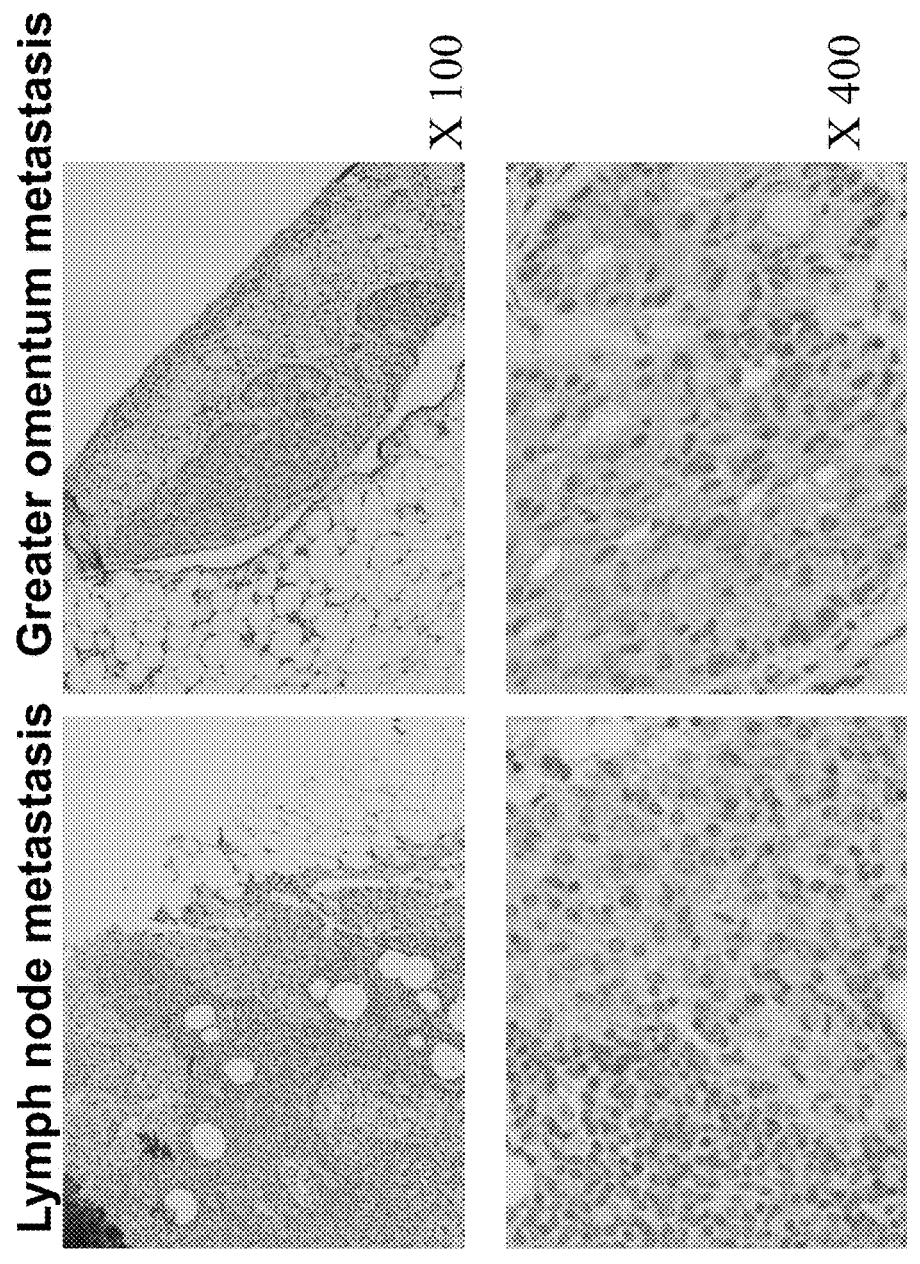

FIG. 32 is a diagram showing that LSRs are also expressed in ovarian cancer metastasized sites. The left column shows lymph node metastasis and the right column shows greater omentum metastasis. The top panel shows 100 times magnification and the bottom panel shows 400 times magnification.

Figure 33:
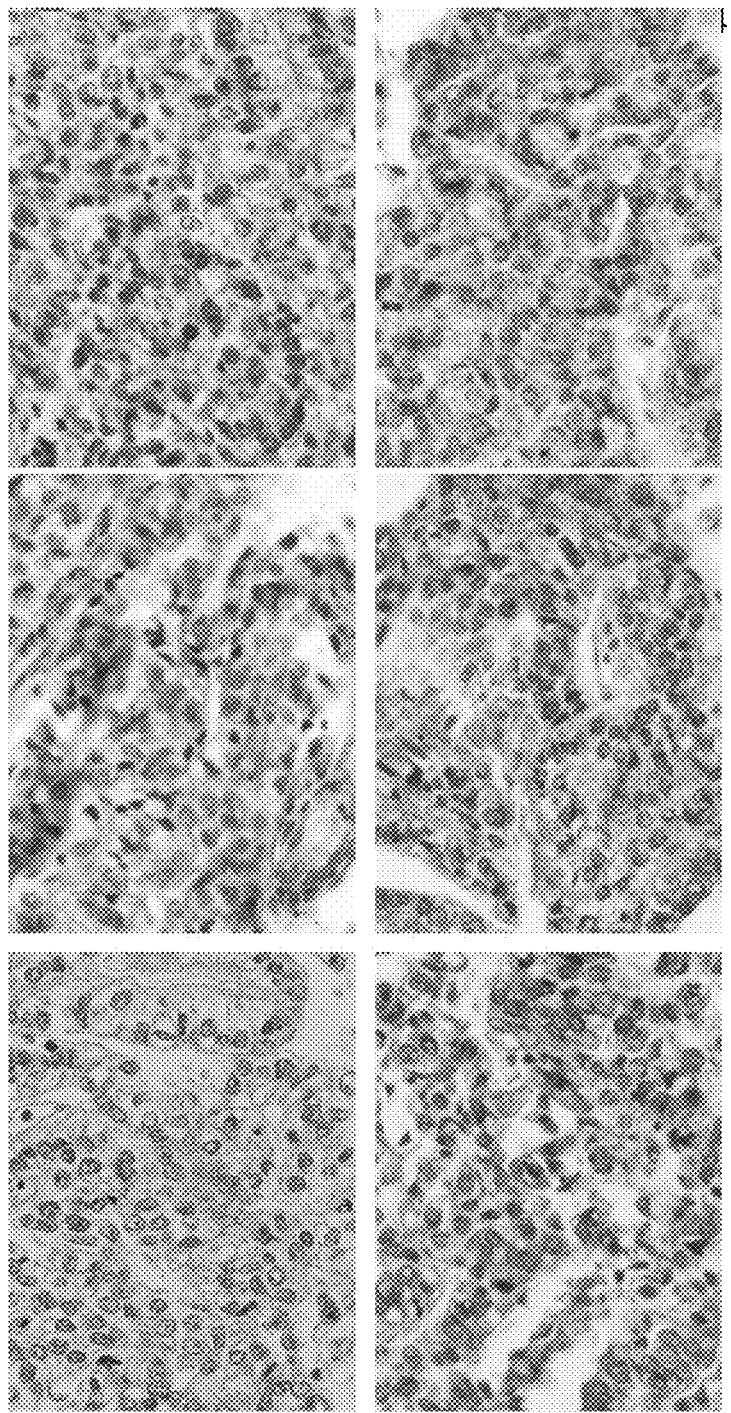

FIG. 33 is a diagram showing that LSRs are expressed in ovary cancer from an early stage. The top left shows hematoxyl in and eosin stain (HE) staining. Top middle shows #1-25A, top right shows #1-45A, bottom left shows #9-7B, bottom middle shows #1-25B, and bottom right shows #1-45B. The cells shown are ovarian clear cells in Stage Ic/IIc.

Figure 34:
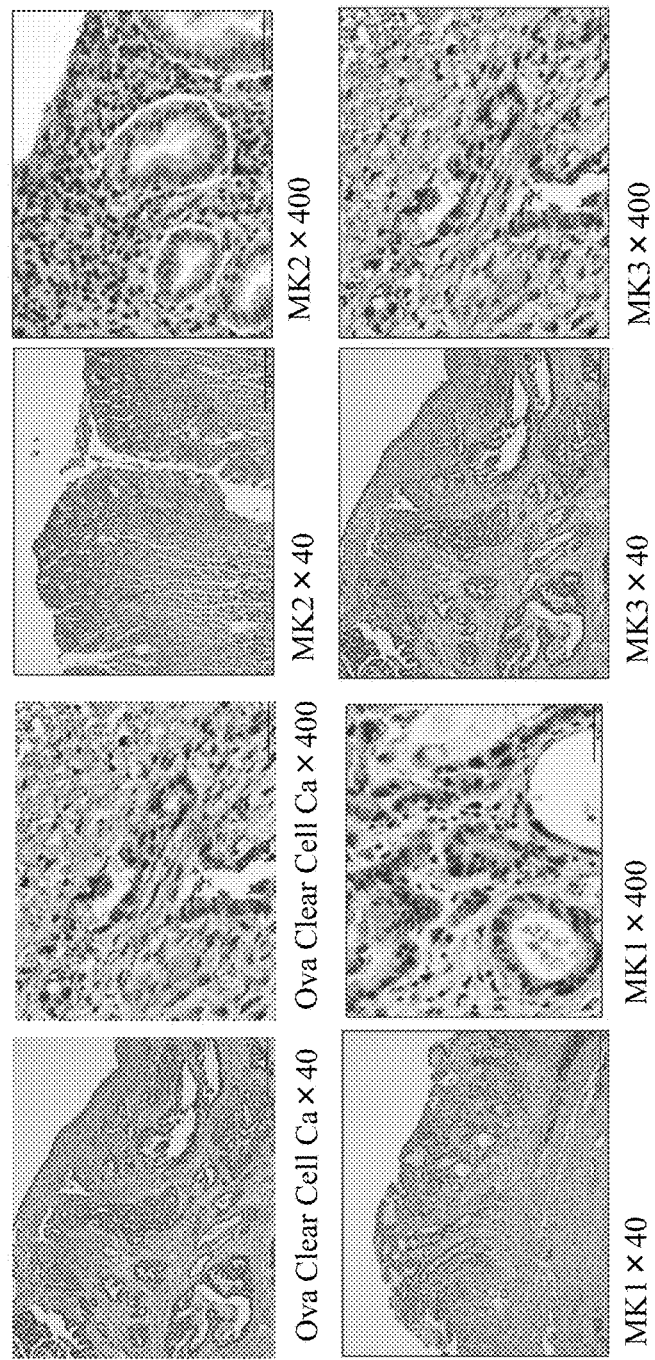

FIG. 34 shows that LSRs are also specifically expressed in gastric cancer. The results of examination by immunostaining are shown, which are results of immunostaining. The top row shows, from the left column, 40 and 400 times magnification of ovarian clear cell cancer and 40 and 400 times magnification of MK2 cells. The bottom row shows pictures of 40 and 400 times magnificent of MK1 and 40 and 400 times magnification of MK3.

Figure 35:
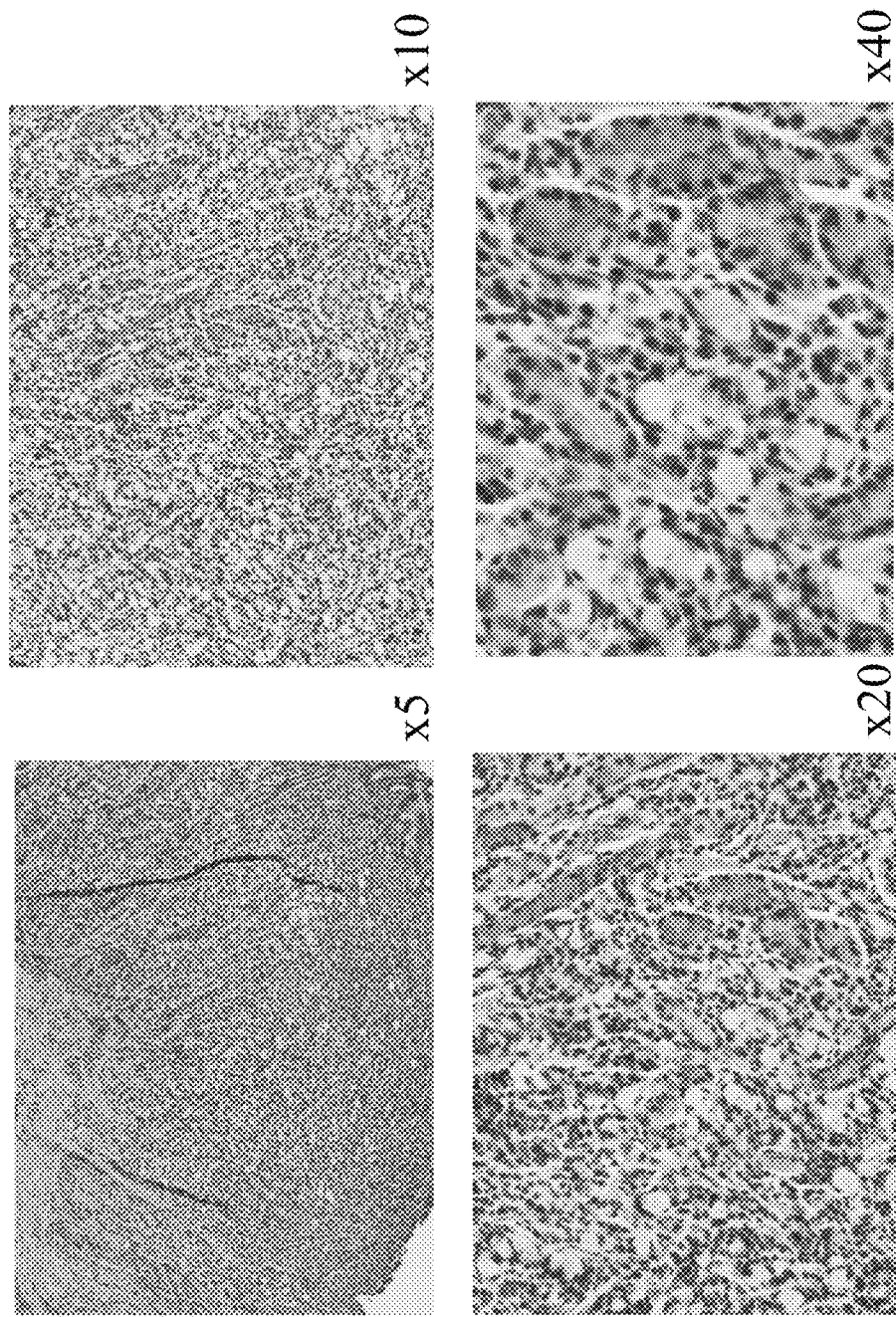

FIG. 35 is a diagram showing that LSRs are strongly expressed in gastric cancer (signet ring cell cancer). The top left panel shows a picture magnified 5 times, top right shows a picture magnified 10 times, bottom left shows a picture magnified 20 times, and bottom right shows a picture magnified 40 times.

Figure 36:
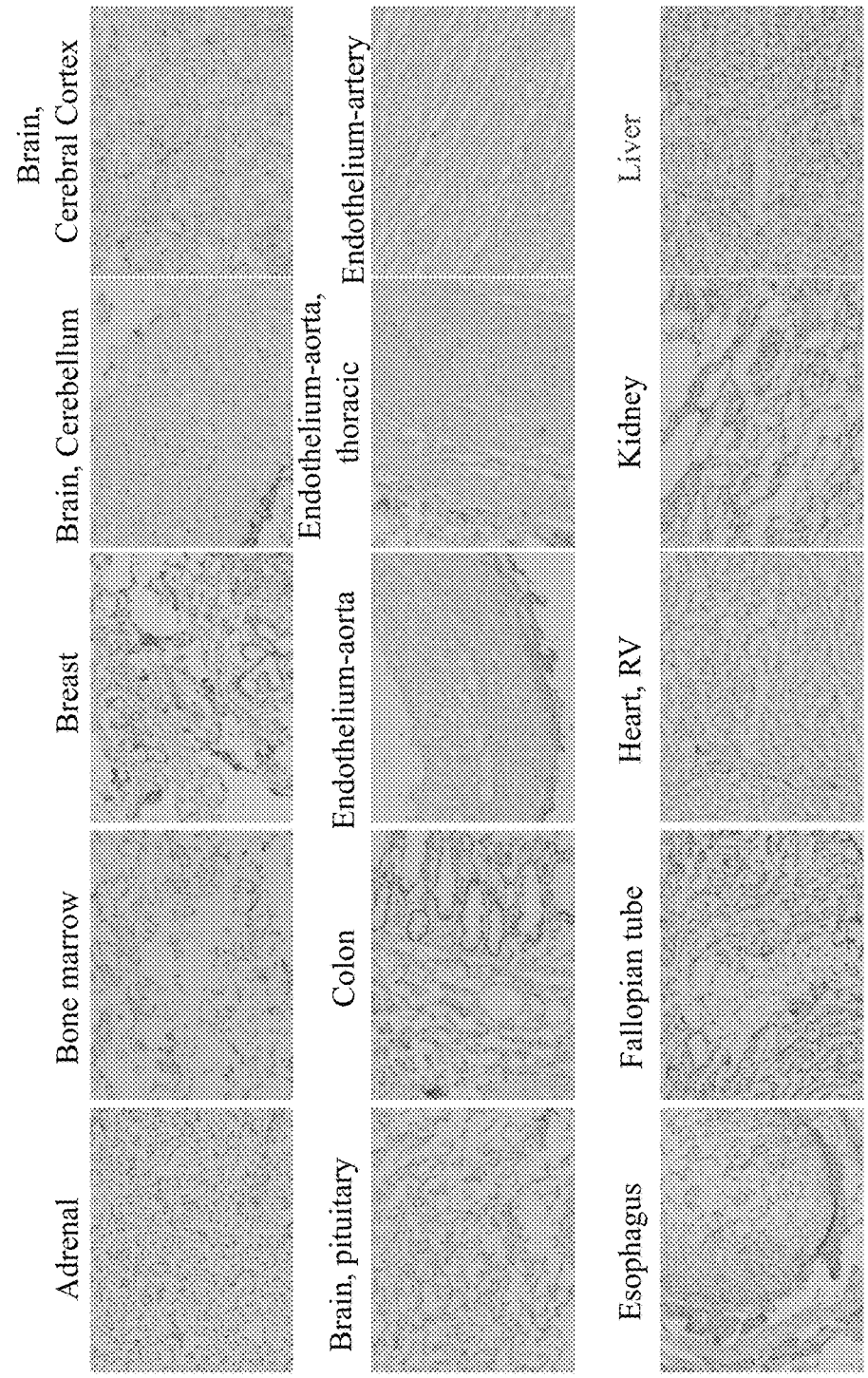

FIG. 36 is a diagram showing analysis of LSR expression by IHC using a normal frozen tissue array. The top row shows, from the left, adrenal gland, bone marrow, breast, brain (cerebellum), and brain (cerebral cortex). The middle row shows, from the left, brain (pituitary gland), colon, endothelium (aorta), endothelium (aorta, thoracic), and endothelium (artery). The bottom row shows, from the left, esophagus, fallopian tube, heart (right ventricle), kidney, and liver.

Figure 37A:
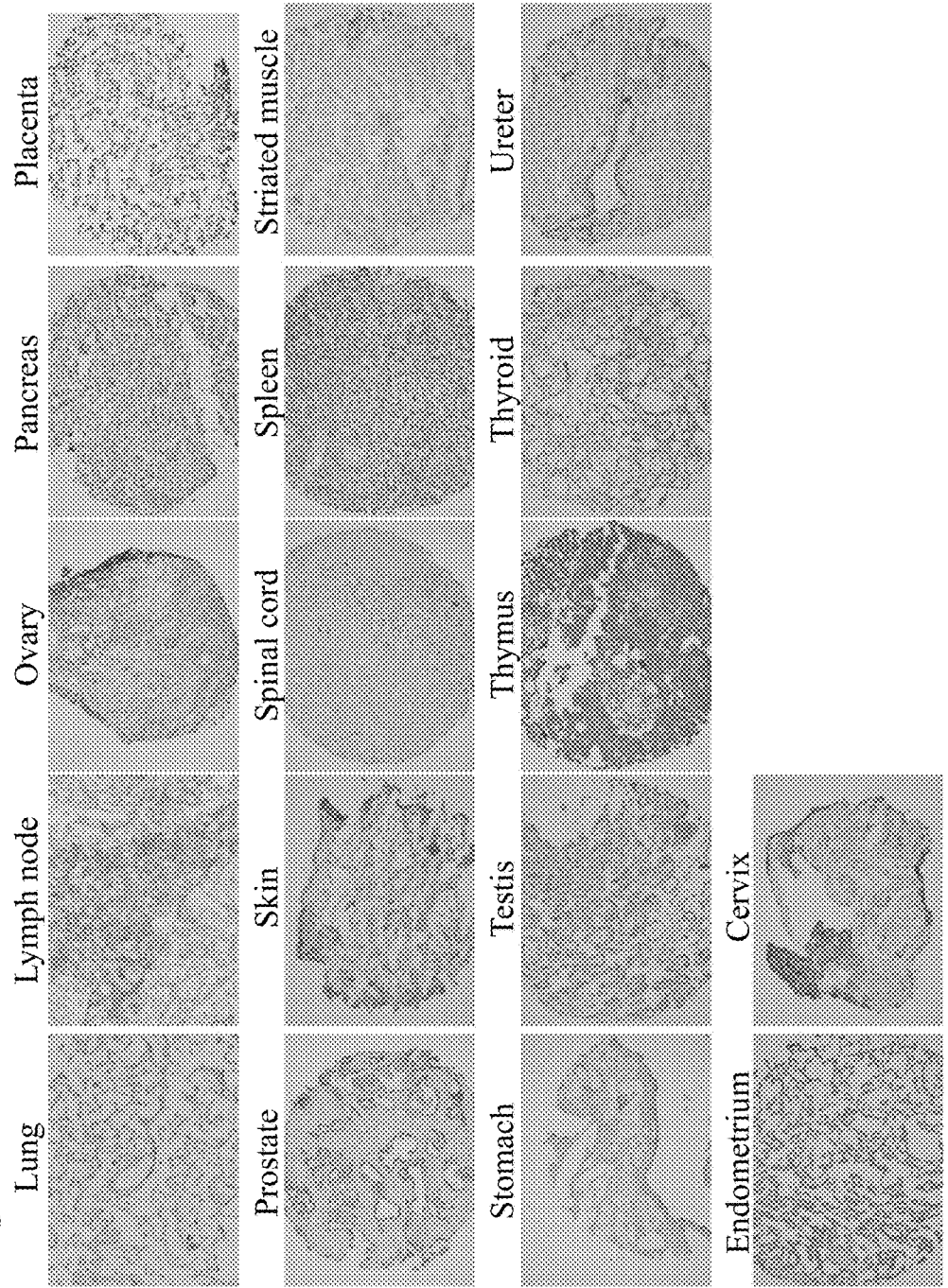

FIG. 37A is a diagram showing analysis of LSR expression by IHC using a normal frozen tissue array. The top row shows, from the left, lung, lymph node, ovary, pancreas, and placenta. The second row from the top shows, from the left, prostate, skin, spinal cord, spleen, and striated muscle. The second row from the bottom shows, from the left, stomach, testis, thymus, thyroid, and ureter. The bottom row shows, from the left, endometrium and cervix.

FIG. 37B shows results of calculating the dissociation constant ($K_D$) of anti-LSR antibodies by FACS. RMG-I cells were stained with antibodies of various concentrations and analyzed by FACS. As shown, #9-7 had $K_D$=2.52 nM, #1-25 had $K_D$=2.03 nM, #16-6 had $K_D$=2.33 nM, #26-2 had $K_D$=4.04 nM, #27-6 had $K_D$=4.29 nM, and #1-43 had $K_D$=24.62 nM.

Figure 38:
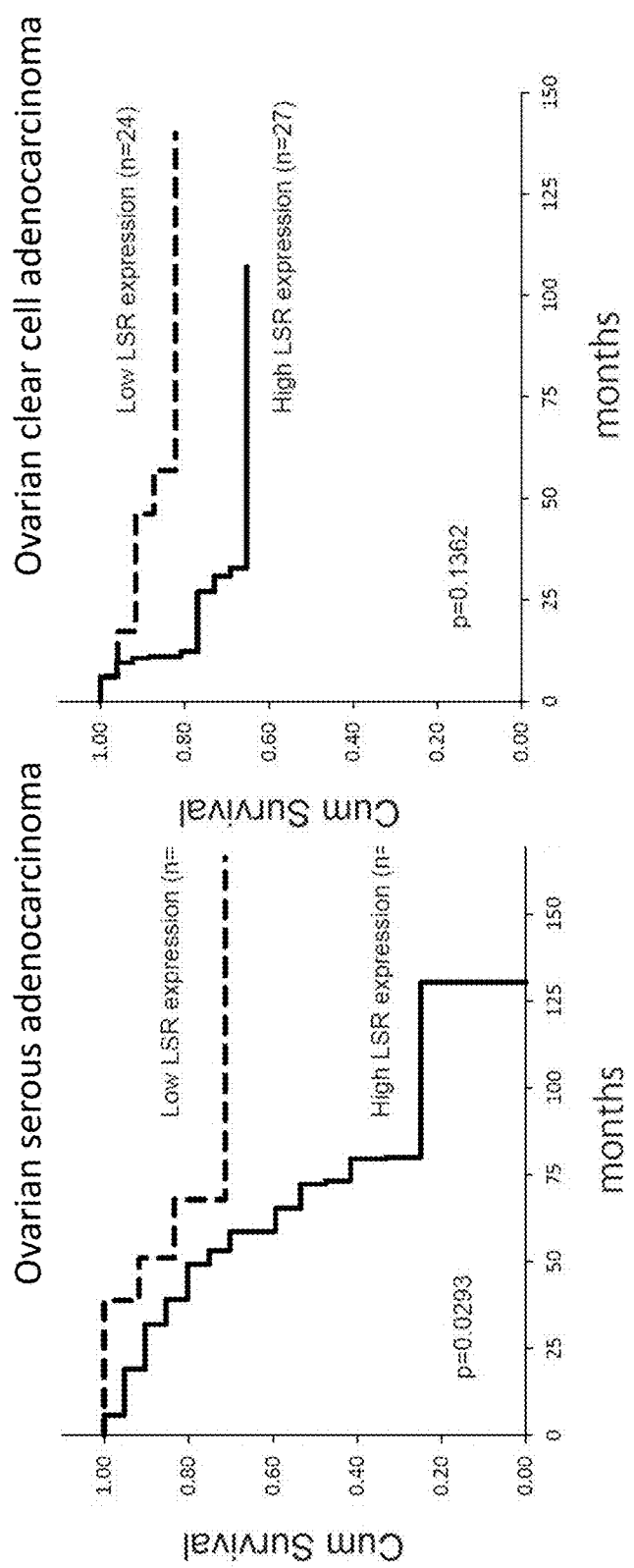

FIG. 38 shows results of investigating prognosis of ovarian serous adenocarcinoma patients or ovarian clear cell adenocarcinoma based on whether the LSR expression is high or low. 21 cases of patients with strong expression of LSRs and 12 cases of patients with weak expression were studied for ovarian serous adenocarcinoma, and 27 cases of patients with strong expression of LSRs and 24 cases of patients with weak expression were studied for ovarian clear cell adenocarcinoma. It can be seen that ovarian serous adenocarcinoma with high level of expression has poorer prognosis compared to the group with low level of expression.

Figure 39:
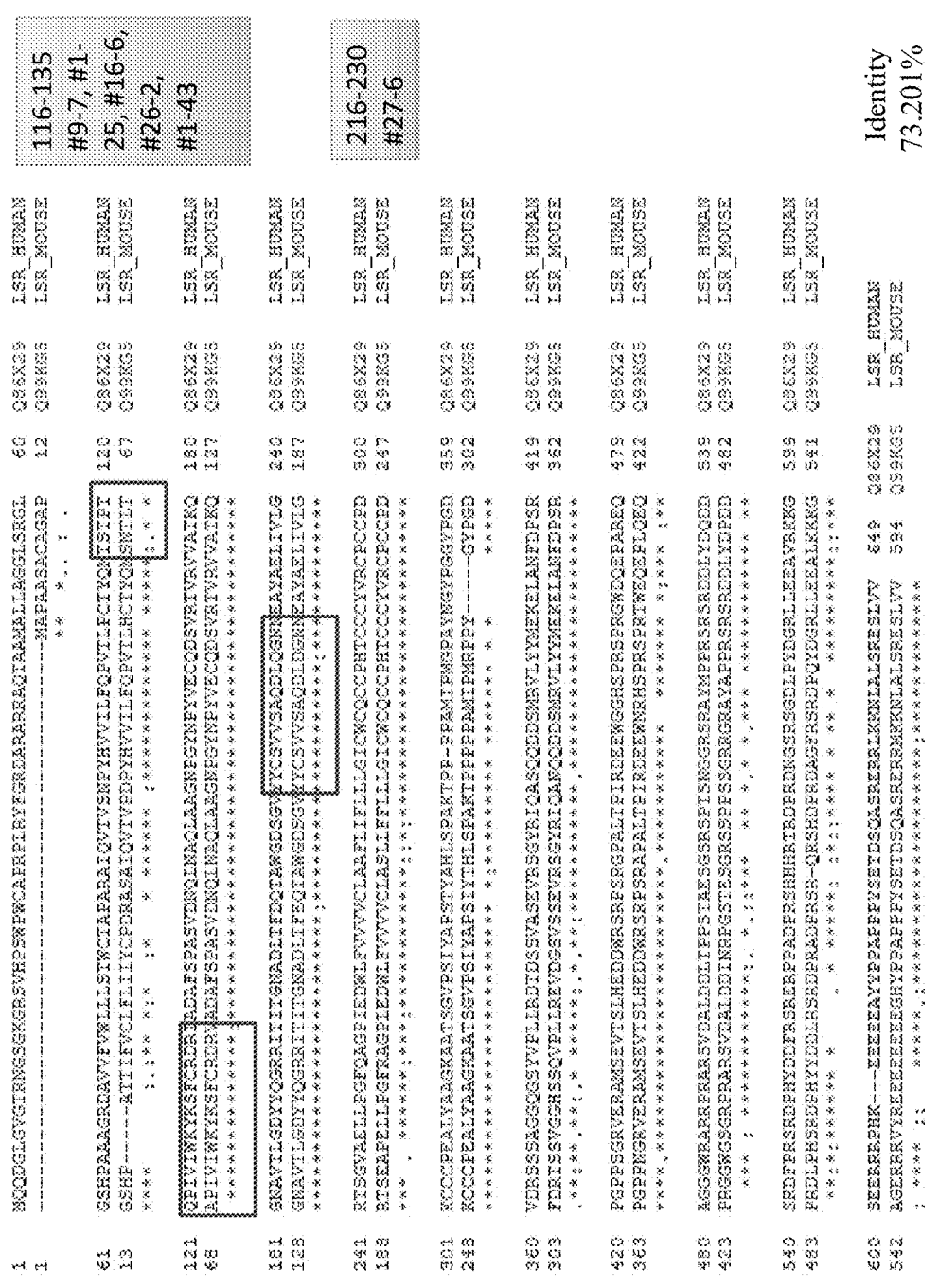

FIG. 39 shows a comparison of the epitope region of hLSR antibody of the antibody of the present invention with the amino acid sequence of hLSR (SEQ ID NO: 21) and mLSR (SEQ ID NO: 22).

Figure 40:
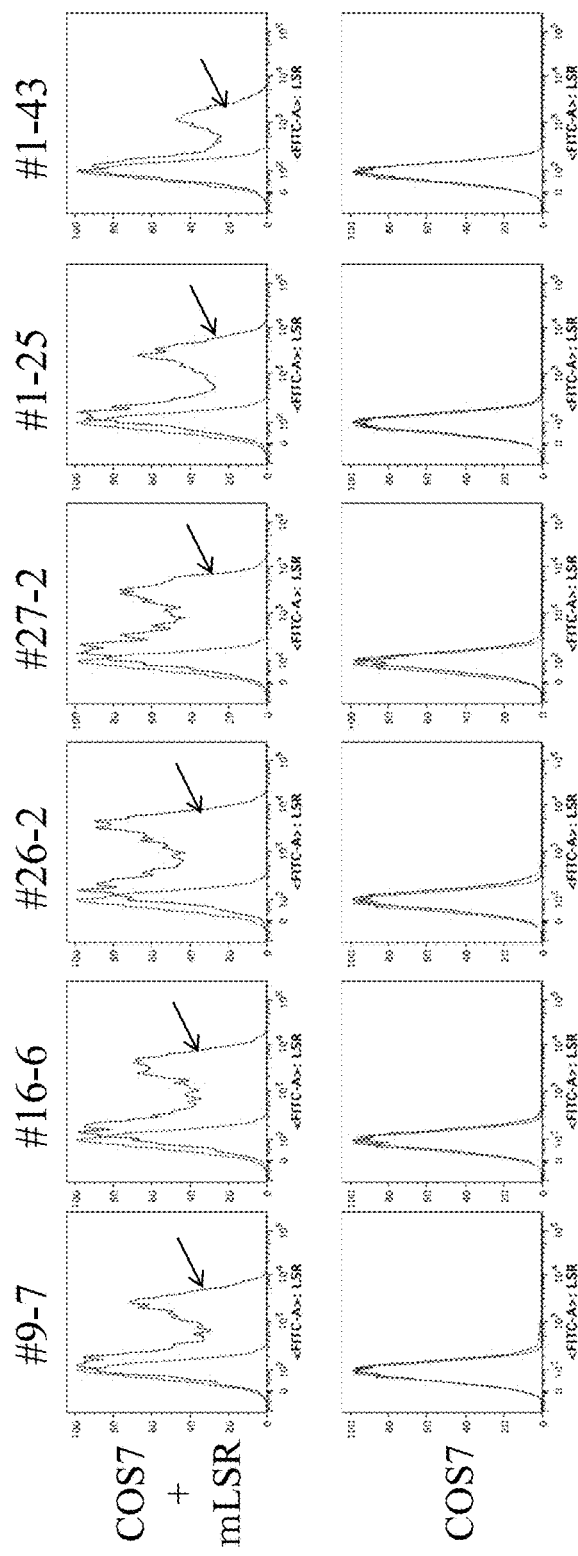

FIG. 40 shows that an anti-hLSR antibody cross-reacts with mLSR. The original diagram is shown in red and blue, where red indicates mIgG2a. Blue indicates the staining pattern in clones of various anti-LSR antibodies. Blue is marked with an arrow in this diagram. The reaction of various antibodies to COS7 cells subjected to transgenesis with pCMV5-mLSR-myc/DDK such that mSR is transiently expressed was confirmed by FACS. The top row shows mixture of COS7 and mLSR and the bottom row shows only COS7 cells. Various antibodies are shown, which are from the left, #9-7, #16-6, #26-2, #27-2, #1-25, and #1-43.

Figure 41:

FIG. 41 shows that anti-LSR induces cell cycle arrest in RMG-I cells in the G0/G1 phase. The graph shows the percentage of cells in the G0/G1 phase, S phase and G2/M phase. For each phase, results for no treatment, treatment with the control IgG, and treatment with antibody #1-25 are shown from the left. The experiment was carried out with a 6 well plate at 15000 cells/well under the conditions of RPMI 1640 medium+1% FBS+1% penicillin-streptomycin (100 μg/ml antibody condition, 96 hours). Treatment with antibody #1-25 was statistically significant (p<0.0001) (one way ANOVA and Dunnett's test).

Figure 42:
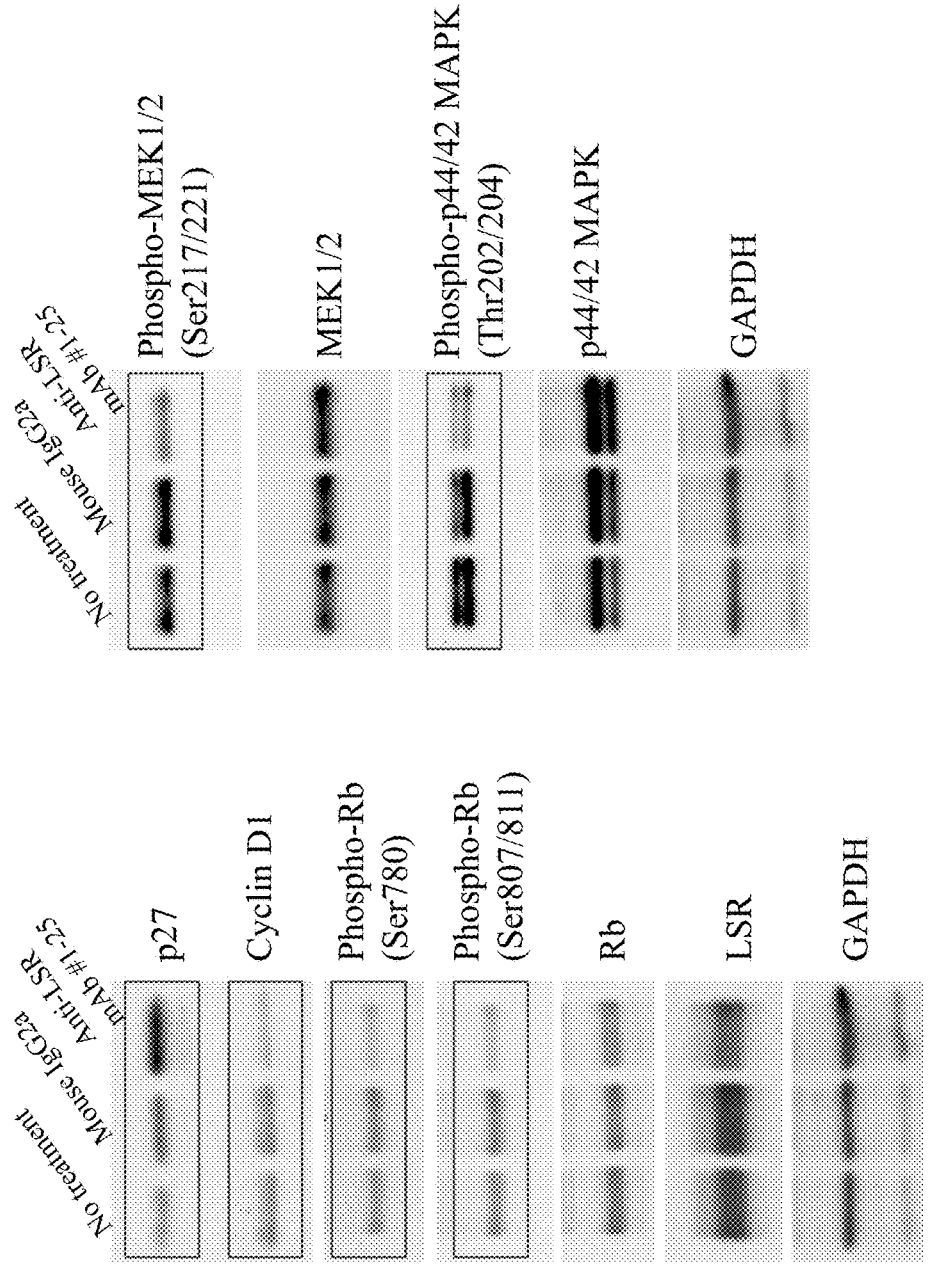

FIG. 42 shows that anti-LSR antibodies enhance p27 expression, suppress cyclin D1 expression, suppress Rb and MAPK activity, and suppress cell growth. Expression was observed by Western blot. The left panel shows, from the top, p27, cyclin D1, phosphorylated Rb (retinoblastoma protein; Ser780), phosphorylated Rb (Ser807/811), Rb only, LSR, and GAPDH as a control. The right panel shows, from the top, phosphorylated-MEK1/2, MEK1/2, phosphorylated p44/42 MAPK, p44/42 MAPK, and GAPDH. For each protein, the results of using, from the left, no treatment, mouse IgG2a, and anti-LSR mAb #1-25 are shown.

Figure 43:
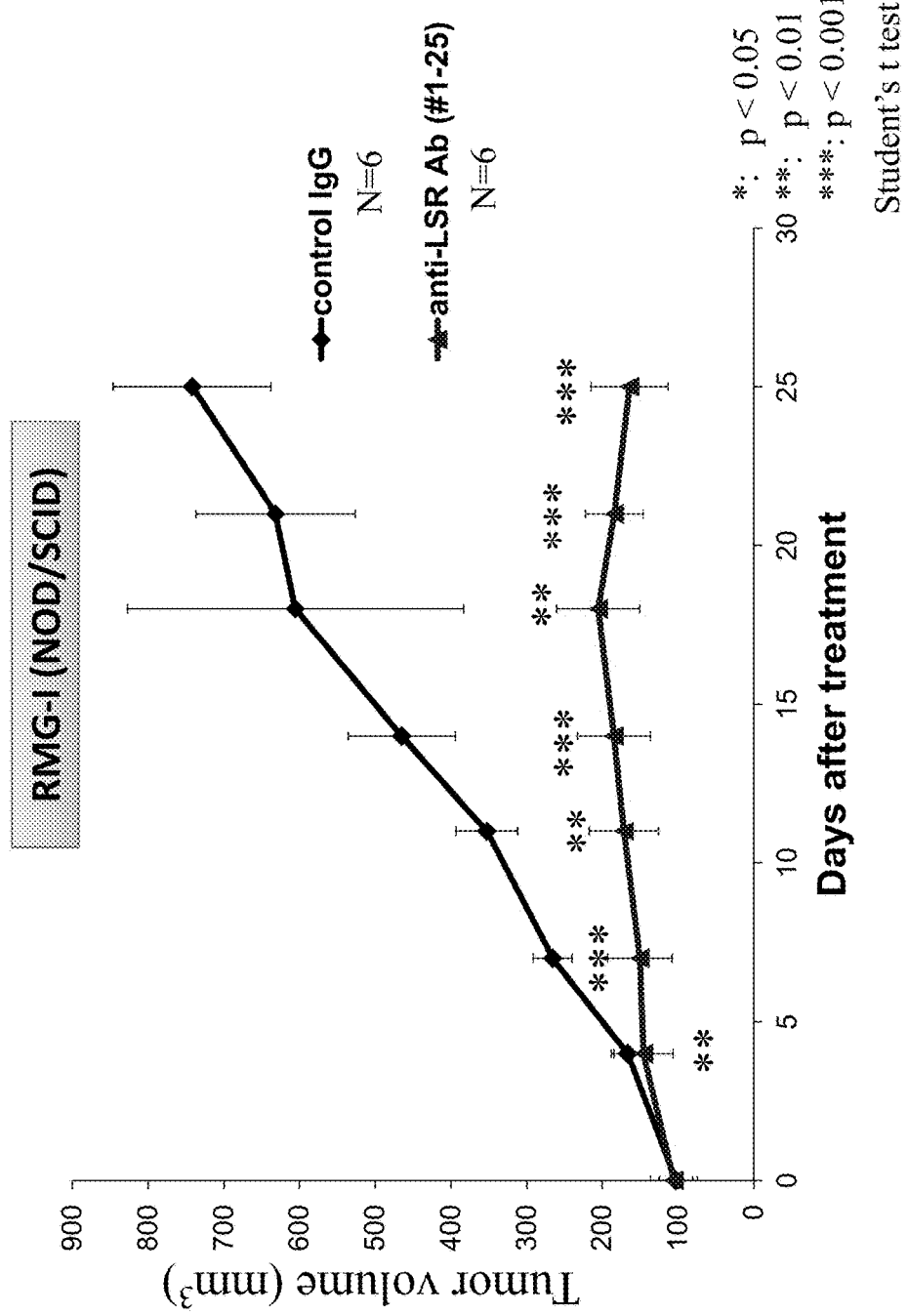

FIG. 43 shows that an anti-LSR antibody also has an ADCC non-dependent anti-tumor effect in addition to anti-tumor effects mediated by ADCC. This is an experiment modeled after RMG-I (NOD/SCID). The graph shows days after treatment (horizontal axis) and tumor volume (mm$^3$) (vertical axis). The rhombuses indicate the control IgG (N=6) and the triangles indicate treatment with anti-LSR Ab (#1-25) (N=6). *, , and * indicate statistical significance (p<0.05, 0.01, and 0.001, Student's t-test), respectively.

Figure 44:
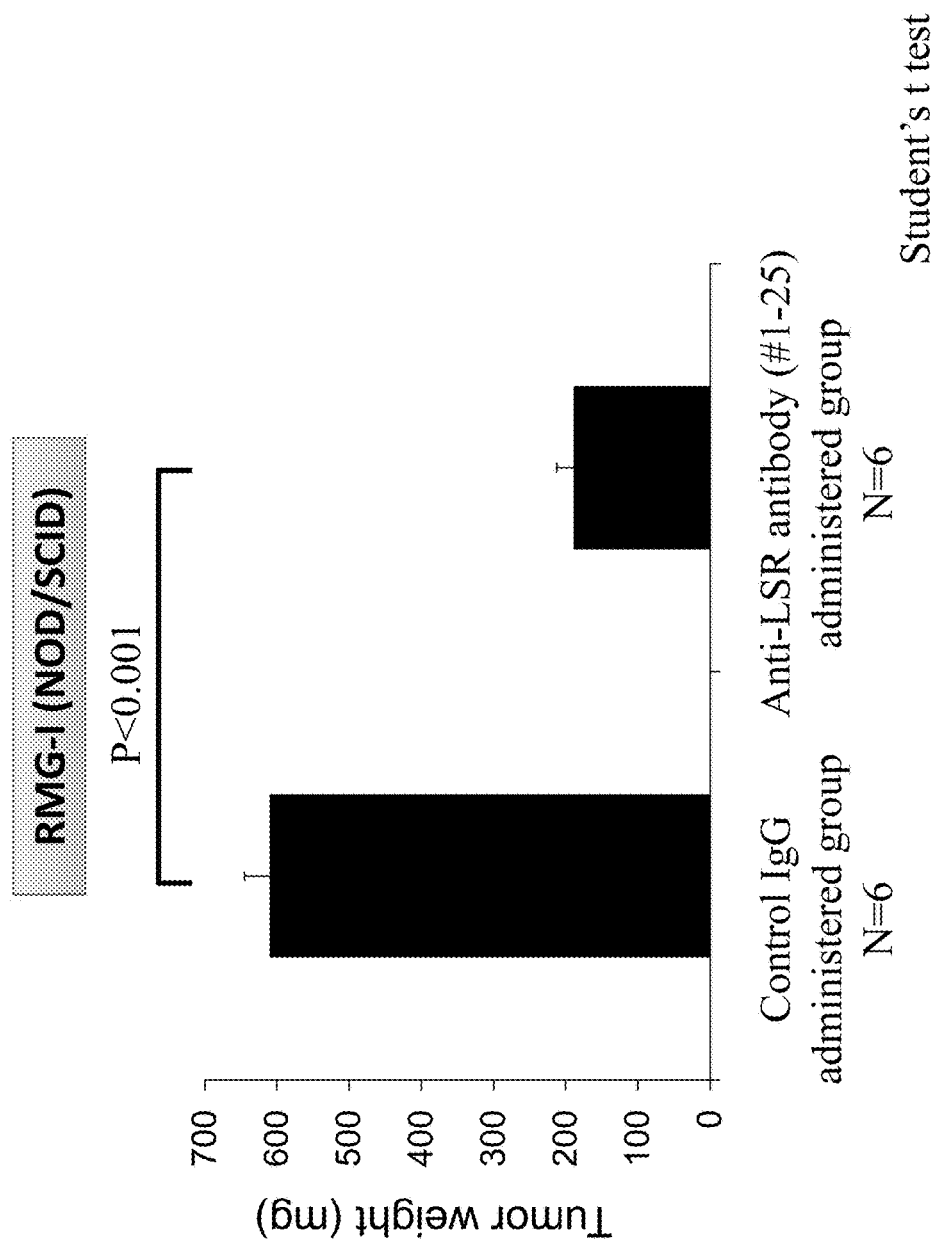

FIG. 44 is another graph showing that an anti-LSR antibody also has ADCC non-dependent anti-tumor effects in addition to an antitumor effect mediated by ADCC. The left side shows the control IgG administered group and the right side shows the anti-LSR antibody (#1-25) administered group. Each group was N=6, and the vertical axis is tumor weight (mg). RMG-I (NOD/SCID) was used as the model. The results were statistically significant (p<0.001, Student's t-test).

Figure 45:
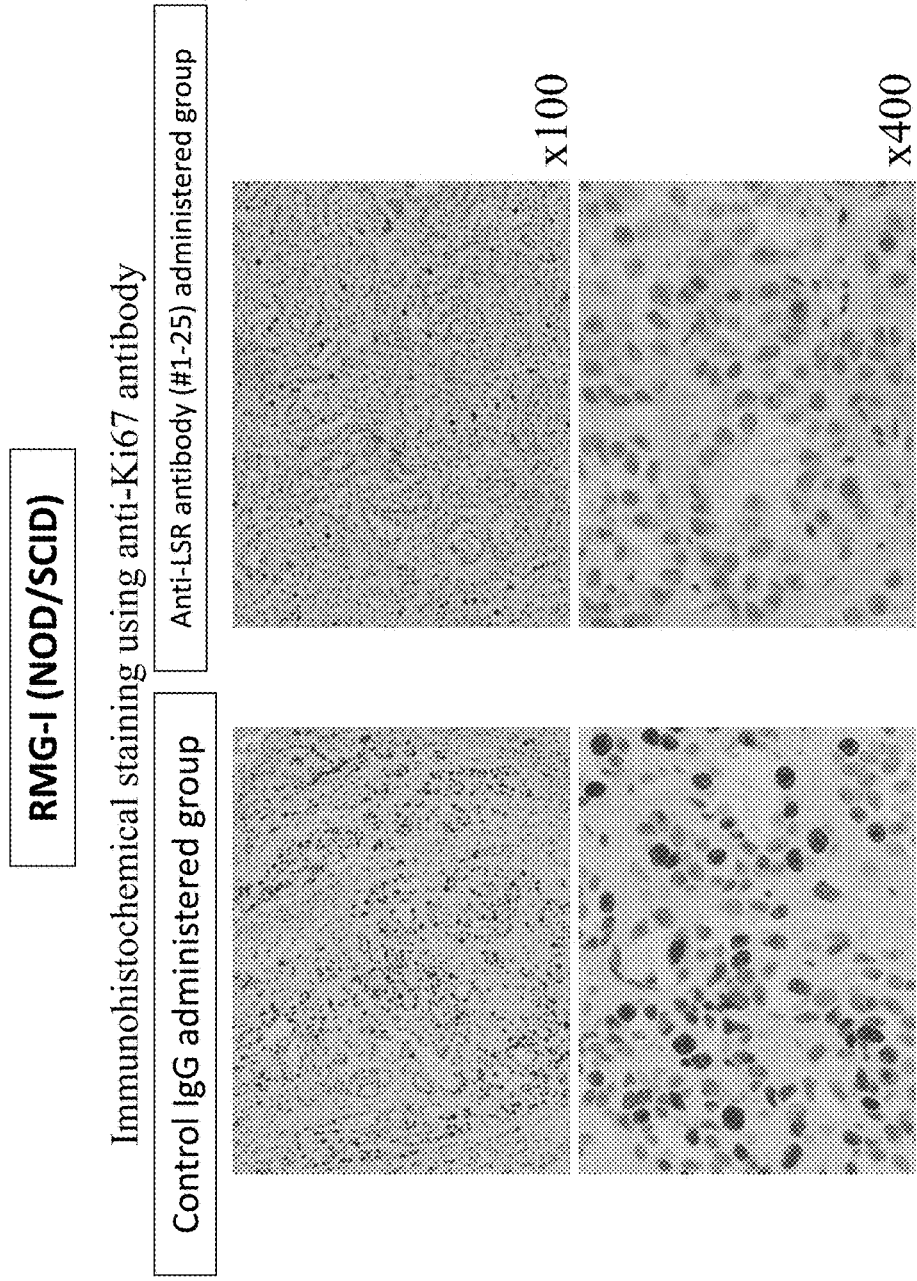

FIG. 45 shows that tumor cells in the growth phase were decreased in vivo by anti-LSR antibodies. Anti-Ki67 antibodies were used for immunohistochemical staining, and RMG-I (NOD-SCID) was used. The left column shows the control IgG administered group, and the right column shows the anti-LSR antibody (#1-25) administered group. The top row shows 100 times magnification and the bottom row shows 400 times magnification.

Figure 46:
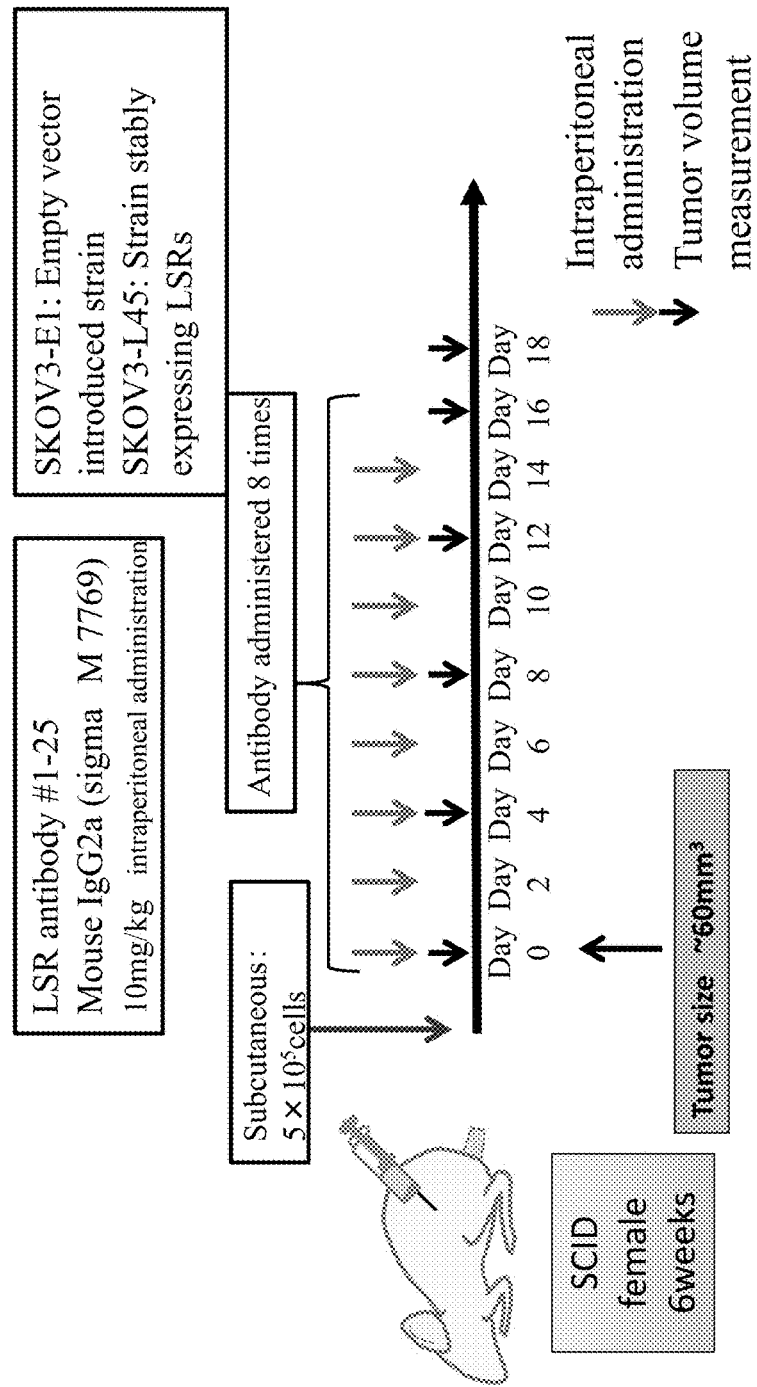

FIG. 46 shows examination of antitumor effects of anti-LSR antibodies on ovarian cancer cell strain (SKOV3-E1, SKOV3-L45, and xenograft model). #1-25 was used as the LSR antibody, and mouse IgG2a (Sigma M7769) was used as the control. 10 mg/kg was intraperitoneally administered. SKOV3-E1 was used as an empty vector introduced strain, and SKOV3-L45 was used as a strain stably expressing LSRs. The arrows on the top side indicate intraperitoneal administration (every other day, up to day 14), and the bottom indicates tumor volume measurement (every 4 days up to day 16 as well as measurement on day 18). An SCID female 6-week old mouse was used as a model. The tumor size was about 60 mm$^3$ on day 0.

FIG. 47 shows that an anti-LSR monoclonal antibody exhibits an antitumor effect on an ovarian cancer cell strain xenograft model expressing LSRs. The graph on the left shows SKOV3-L45 (SCID) (strains stably expressing LSRs) and the graph on the right shows SKOV3-E1 (SCID) (empty vector). For each graph, the horizontal axis indicates the days after treatment, and the vertical axis indicates the tumor volume (mm$^3$). The rhombuses indicate the control IgG (N=5) and the triangles indicate treatment with anti-LSR Ab (#1-25) (N=5). *, , and * indicate statistical significance (p<0.05, 0.01, and 0.001, Student's t-test), respectively.

Figure 48:
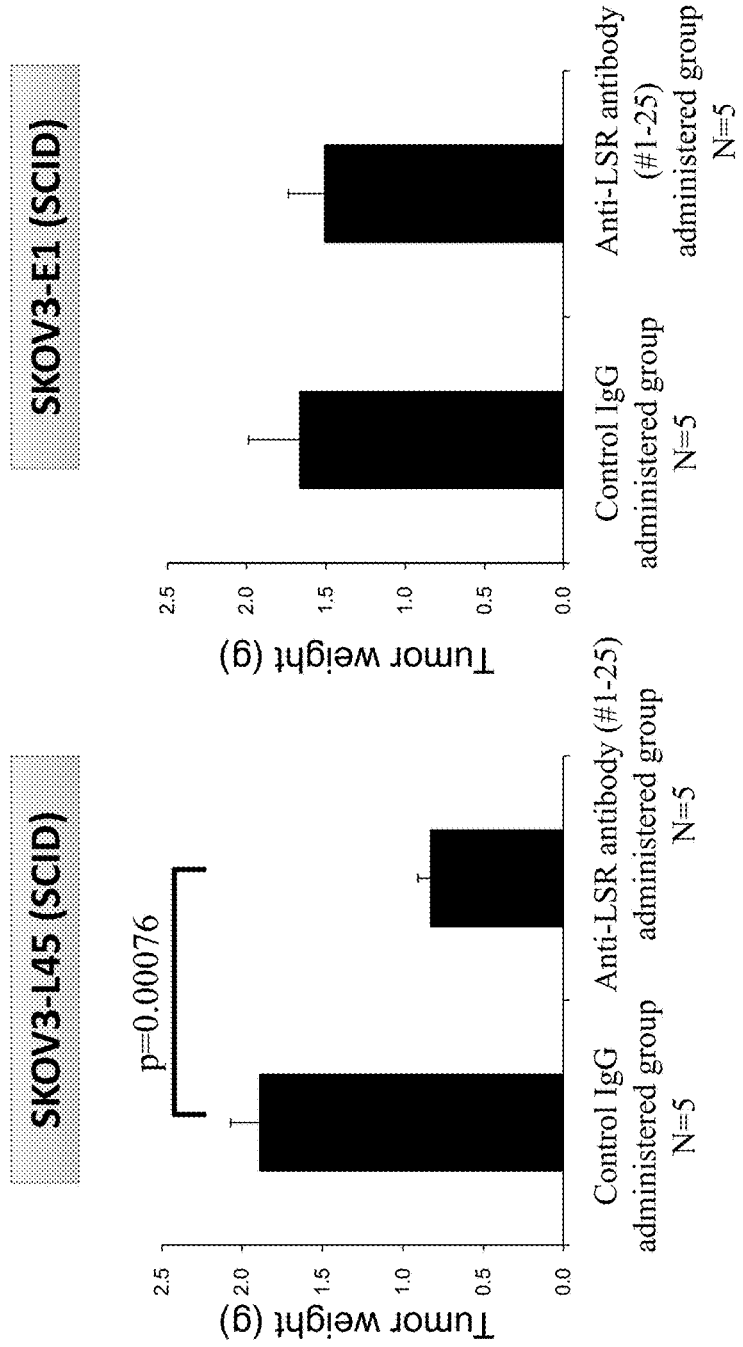

FIG. 48 shows that an anti-LSR monoclonal antibody exhibits an antitumor effect on an ovarian cancer cell strain xenograft model expressing LSRs. The graph on the left shows SKOV3-L45 (SCID) (strains stably expressing LSRs) and the graph on the right shows SKOV3-E1 (SCID) (empty vector). N=5 for each group, and the vertical axis is the tumor weight (mg). The rhombuses indicate the control IgG (N=5) and the triangles indicate treatment with anti-LSR Ab (#1-25) (N=5). As shown, it was demonstrated that anti-LSR monoclonal antibodies do not exhibit an antitumor effect on LSR negative cells, but exhibit an antitumor effect specifically against LSR expressing positive cells (was statistically significant (p<0.00076, Student's t-test)).

Figure 49:
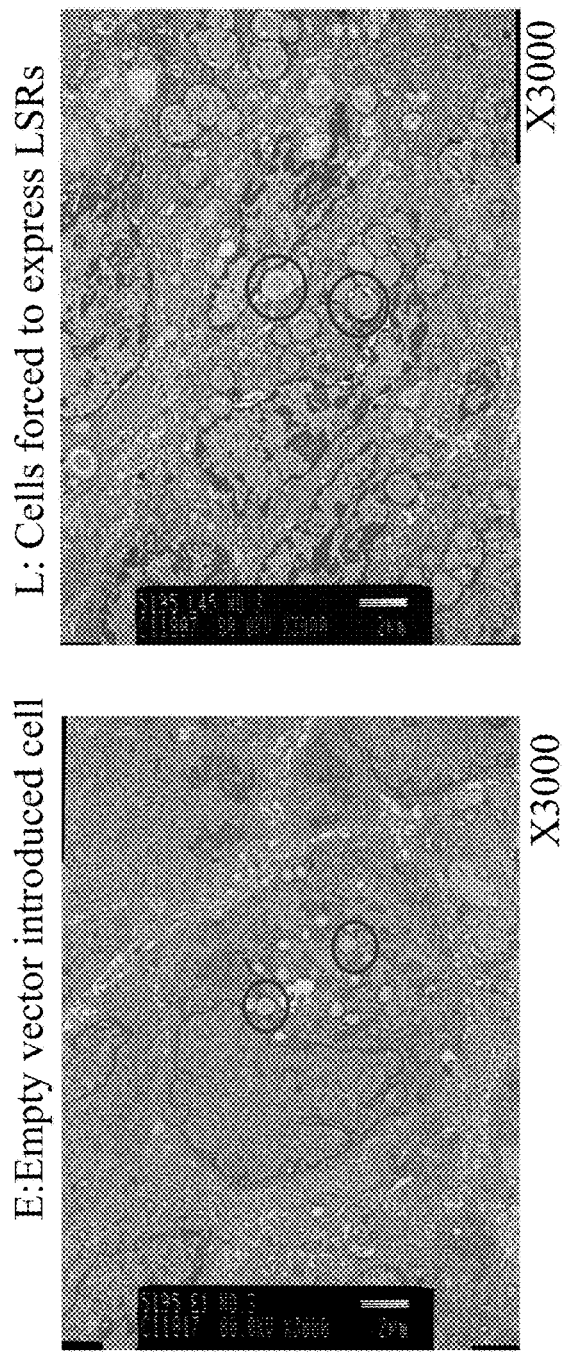

FIG. 49 shows that an LSR incorporates VLDL and promotes lipid metabolism. The left side shows a vector introduced cell, and the right side shows cells forced to express LSRs.

Figure 50:
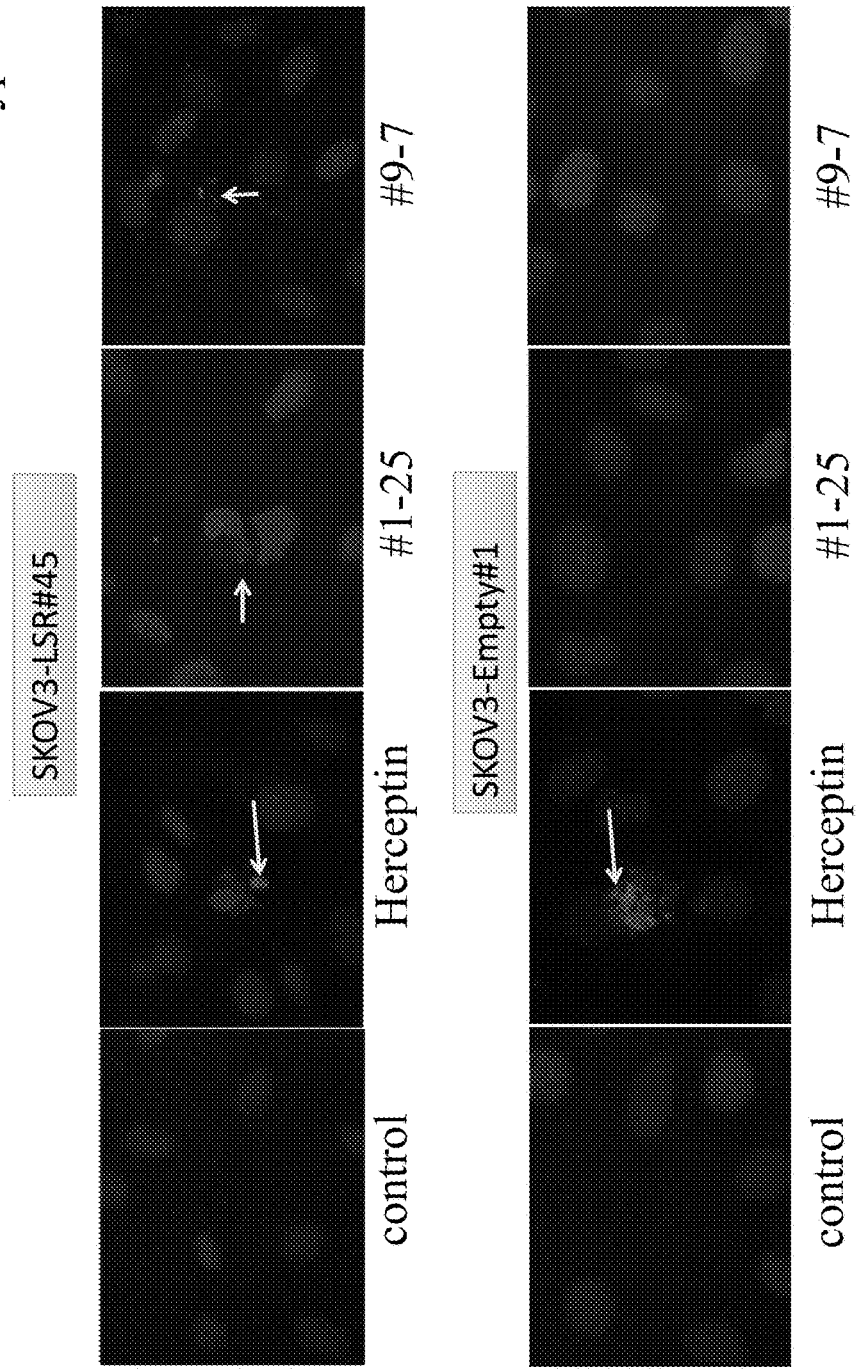

FIG. 50 shows results of examining intracellular incorporation of LSR monoclonal antibodies. The top row shows results of SKOV3-LSR#45 and the bottom row shows results of SKOV3-Empty#1 (empty vector). The results are shown, from the left, for control treatment, Herceptin treatment, antibody #1-25 treatment, and antibody #9-7 treatment. The arrows indicate various clones of anti-LSR antibodies or Herceptin incorporated into the cell.

Figure 51:
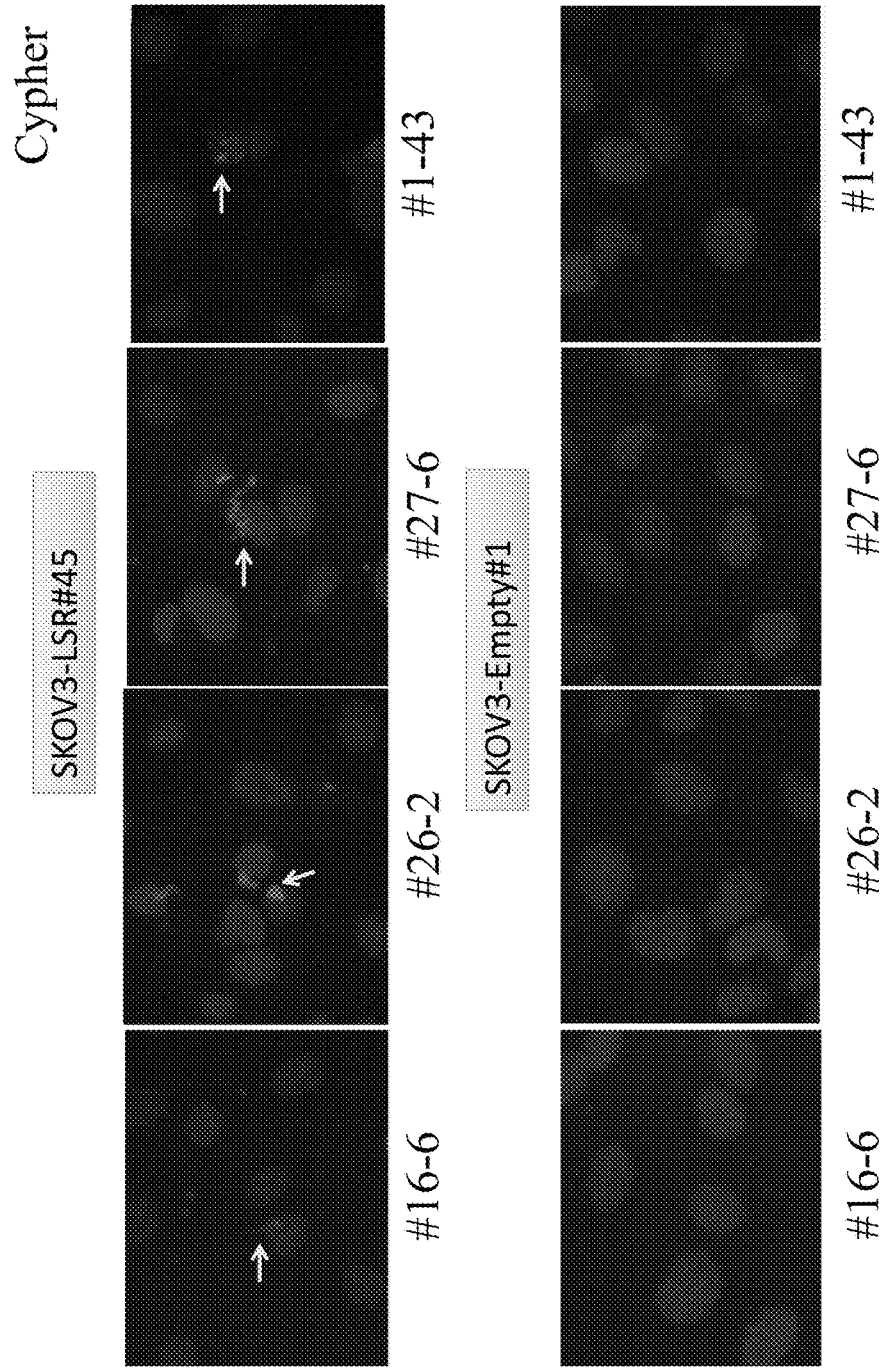

FIG. 51 shows results of examining intracellular incorporation of LSR monoclonal antibodies similar to FIG. 50. The top row shows results for SKOV3-LSR#45 and the bottom row shows SKOV3-Empty#1 (empty vector). From the left, antibodies #16-6, #26-2, #27-6 and #1-43 are shown. The arrows show various clones of anti-LSR antibodies incorporated into the cell.

FIG. 52 shows the protocol for a safety test on anti-LSR antibodies using a mouse. 1 mg/body weight of mouse IgG2a (Sigma M7769) and anti-LSR antibody #1-26 was intraperitoneally administered to C57BL/6J (8 weeks old) to assess the following items on day 7. The brain, heart, kidney, liver, lung and spleen are selected as the extracted organs. The measured items include while blood cell (WBC), red blood cell (RBC), hemoglobin (Hb), platelet (Plt), total bilirubin (T-Bil), alanine aminotransferase (ALT), alkaline phosphatase (ALP), amylase (Amy), blood urea nitrogen (BUN), chrome (Cr), calcium (Ca), phosphorus (P), total protein (TP), albumin (Alb), sodium (Na), potassium (K), globulin (Globn), and glutamine (Glu). VetScan™ HMII (Abaxis, Inc.) was used as an automated blood cell counter, and VetScan™ VS2 (Abaxis Inc 0 was used as a veterinary biochemical blood analyzer.

FIG. 53 shows a comparison of control IgG versus anti-LSR antibody (male). In the Table, the left column shows the items, second column from the left shows control IgG (n=3), the third column shows anti-LSR antibodies (n=3), the second column from the right shows normal values, and the right end shows the p value (statistical significance in Student'st-test). In addition to the abbreviations explain in FIG. 52, Ly indicates lymphocytes and Mo indicates monocytes. Gr indicates granulocytes and Hct indicates hematocrit values.

FIG. 54 shows a comparison of control IgG versus anti-LSR antibody (female). Each of the values is the same as that in FIGS. 52-53.

FIG. 55 shows a comparison of control IgG versus anti-LSR antibody (male). In the Table, the left column shows the items, the second column from the left shows control IgG (n=3), the third column shows anti-LSR antibodies (n=3), the second column from the right shows normal values, and the right end shows the p value (statistical significance in Student's t-test). The abbreviations are as explained in FIG. 52.

FIG. 56 shows a comparison of control IgG versus anti-LSR antibody (female). Each of the values is the same as that in FIGS. 52-53 and 55.

DESCRIPTION OF EMBODIMENTS

The embodiments of the present invention are described in detail hereinafter. It should be noted that descriptions are omitted when appropriate for the same content in order to avoid complicating the content by repeating. Throughout the entire specification, a singular expression should be understood as encompassing the concept thereof in the plural form, unless specifically noted otherwise. Thus, singular articles (e.g., "a", "an", "the" and the like in case of English) should also be understood as encompassing the concept thereof in the plural form unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the terms commonly understood by those skilled in the art to which the present invention pertains. In case of a contradiction, the present specification (including the definitions) takes precedence.

First, explanations are provided for the terms and general techniques used in the present invention.

As used herein, "LSR (lipolysis stimulated lipoprotein receptor)" is generally known as a molecule associated with the metabolism of a low density lipoprotein (LDL). The details of the amino acid sequence or the like of LSRs can be found on the websites of the NCBI (National Center for Biotechnology Information), HGNC (HUGO Gene Nomenclature Committee) or the like. Examples of accession numbers of LSRs described in NCBI are NP_991403 (amino acid) and /NM_205834.3 (mRNA). An example of the amino acid sequence of an LSR is SEQ ID NO: 7. An example of the base sequence of an LSR mRNA is SEQ ID NO: 8. The amino acid sequence of an LSR is not limited, as long as the sequence has LSR activity. Thus, it is understood that not only proteins (or nucleic acid encoding the same) having an amino acid sequence set forth in a specific sequence identification number or accession number, but also a functionally active analog or derivative thereof, a functionally active fragment thereof or homolog thereof, or a mutant encoded by a nucleic acid which hybridizes to a nucleic encoding said protein under a highly stringent condition or lowly stringent condition can also be used in the present invention, as long as they align with the specific objective of the present invention.

As used herein, "derivative", "analog", or "mutant" includes, but is not intended to be limited to, molecules comprising a region substantially homologous to a target protein (e.g., LSR). Such a molecule, in various embodiments, is at least 30%, 40%, 50%, 60%, 70%, 80%, 90%, 95% or 99% identical throughout the amino acid sequence of the same size or in comparison to a sequence aligned by a homology computer program known in the art. Alternatively, a nucleic acid encoding such a molecule can hybridize to a sequence encoding the constituent protein under a (highly) stringent condition, moderately stringent condition, or non-stringent condition. This refers to a product of altering a naturally-occurring protein by an amino acid substitution, deletion and addition, respectively, a protein whose derivative exhibits the biological function of the naturally-occurring protein, although not necessarily to the same degree. For instance, the biological function of such a protein can be investigated by a suitable and available in vitro assay described herein or known in the art. As used herein, "functionally active" refers to polypeptides, i.e., fragments or derivatives, having a structural function, regulatory function or biochemical function of a protein such as biological activity in accordance with an embodiment associated with the polypeptides, i.e., fragments or derivatives, of the present invention. The discussion regarding LSRs in the present invention mainly pertains to humans, but it is understood that many animals other than humans, especially mammals, are within the scope of the present invention, as they are known to express LSRs. Preferably, the functional domain of LSRs e.g., transmembrane domain (positions 260-280) or phosphorylation sites (positions 309, 328, 406, 493, 528, 530, 535, 540, 551, 586, 615, and 646), are conserved.

A fragment of an LSR in the present invention is a polypeptide comprising any region of the LSR. As long as such a fragment serves the function of interest (e.g., marker or therapeutic target) of the present invention, it is not necessary that the fragment has biological functions of a naturally-occurring LSR.

Thus, a representative nucleotide sequence of an LSR may be:
(a) a polynucleotide having a base sequence set forth in SEQ ID NO: 7 or a fragment sequence thereof;
(b) a polynucleotide encoding a polypeptide consisting of the amino acid sequence set forth in SEQ ID NO: 8 or a fragment thereof;

(c) a polypeptide encoding a variant polypeptide having a mutation selected from the group consisting of a substitution, addition, and deletion of one or more amino acids in the amino acid sequence set forth in SEQ ID NO: 8, the variable polypeptide having biological activity, or a fragment thereof;
(d) a polynucleotide, which is a splice mutant or an allelic mutant of the base sequence set forth in SEQ ID NO: 7, or a fragment thereof;
(e) a polynucleotide encoding a species homolog of a polypeptide consisting of the amino acid sequence set forth in SEQ ID NO: 8, or a fragment thereof;
(f) a polynucleotide encoding a polypeptide, which hybridizes with the polynucleotide of any one of (a)-(e) under stringent conditions and has biological activity; or
(g) a polynucleotide encoding a polypeptide consisting of abase sequence, which is at least 70%, at least 80%, at least 90%, at least 95%, at least 96%, at least 97%, at least 98%, or at least 99% identical to the polynucleotide of any one of (a)-(e) or a complementary sequence thereof and has biological activity. Biological activity in this regard typically refers to the property of being distinguishable from other proteins that are present in the same organism as a marker or activity of an LSR.

The amino acid of an LSR may be
(a) a polypeptide consisting of the amino acid sequence set forth in SEQ ID NO: 8 or a fragment thereof;
(b) a polypeptide, which has a mutation selected from the group consisting of a substitution, addition, and deletion of one or more amino acids in the amino acid sequence set forth in SEQ ID NO: 8 and has biological activity;
(c) a polypeptide encoded by a splice mutant or an allelic mutant of the base sequence set forth in SEQ ID NO: 7;
(d) a polypeptide, which is a species homolog of the amino acid sequence set forth in SEQ ID NO: 8;
(e) a polypeptide, which has an amino acid sequence that is at least 70%, at least 80%, at least 90%, at least 95%, at least 96%, at least 97%, at least 98%, or at least 99% identical to the polypeptide of any one of (a)-(d) and has biological activity. Biological activity in this regard typically refers to the property of being distinguishable from other proteins that are present in the same organism as a marker or activity of an LSR (for example, when used as an antigen, a property of comprising a region that can function as a specific epitope).

In the context of the present invention, "substance that binds to an LSR", "LSR binding agent", or "LSR interaction molecule" is a molecule or substance that binds at least transiently to an LSR. For detection purposes, it is preferable that such a molecule or substance is advantageously capable of indicating that the molecule or substance is bound (i.e., labelled or in a labelable state). For therapeutic purposes, it is more advantageous that such a molecule or substance is bound to a therapeutic agent. Examples of a substance that binds to an LSR include antibodies, antisense oligonucleotides, siRNAs, low molecular weight molecules (LMW), binding peptides, aptamers, ribozymes, peptidomimetics and the like. A substance that binds to an LSR or LSR interaction molecule may be an LSR inhibitor, and encompasses, for instance, binding proteins or binding peptides directed to an LSR, especially those directed to an active site of an LSR, as well as nucleic acids directed to a gene of an LSR. A nucleic acid directed to an LSR refers to, for example, a double stranded or single stranded DNA or RNA inhibiting the expression of an LSR gene or activity of an LSR or a modified product or derivative thereof, including, but not limited to, antisense nucleic acids, aptamers, siRNAs (small interfering RNA) and ribozymes. As used herein, "binding protein" or "binding peptide", with respect to an LSR, refers to any protein or peptide that binds to the LSR, including, but not limited to, antibodies directed to the LSR (e.g., polyclonal antibodies or monoclonal antibodies), antibody fragments and functional equivalents.

As used herein, "protein", "polypeptide", "oligopeptide" and "peptide" are used herein in the same meaning and refer to an amino acid polymer of any length. The polymer may be straight, branched or cyclic. An amino acid may be a naturally-occurring, non-naturally occurring or altered amino acid. The term may also encompass those assembled into a complex of multiple polypeptide chains. The term also encompasses naturally-occurring or artificially altered amino acid polymers. Examples of such an alteration include disulfide bond formation, glycosylation, lipidation, acetylation, phosphorylation, and any other manipulation or alteration (e.g., conjugation with a labeling component). The definition also encompasses, for example, polypeptides comprising one or more analogs of an amino acid (e.g., including non-naturally occurring amino acids and the like), peptide-like compounds (e.g., peptoids) and other alterations in the art. As used herein, "amino acid" is a general term for organic compounds with an amino group and a carboxyl group. When the antibody according to an embodiment of the present invention comprises a "specific amino acid sequence", any of the amino acids in the amino acid sequence may be chemically modified. Further, any of the amino acids in the amino acid sequence may be forming a salt or a solvate. Further, any of the amino acids in the amino acid sequence may have an L form or a D form. Even for such cases, the protein according to an embodiment of the present invention is considered as comprising the above-described "specific amino acid sequence". Examples of known chemical modifications applied to an amino acid comprised in a protein in a living body include modifications of the N-terminus (e.g., acetylation, myristylation and the like), modifications of the C-terminus (e.g., amidation, addition of glycosylphosphatidylinositol and the like) modifications of a side chain (e.g., phosphorylation, glycosylation and the like) and the like. The modifications may be naturally-occurring or non-naturally occurring, as long as the objective of the present invention is met.

As used herein, "polynucleotide", "oligonucleotide" and "nucleic acid" are used herein in the same meaning, and refer to a polymer of nucleotides with any length. The terms also encompass "oligonucleotide derivative" and "polynucleotide derivative". "Oligonucleotide derivative" and "polynucleotide derivative" refer to an oligonucleotide or polynucleotide that comprises a nucleotide derivative or has a bond between nucleotides which is different from normal. The terms are used interchangeably. Specific examples of such an oligonucleotide include 2'-O-methyl-ribonucleotide, oligonucleotide derivatives having a phosphodiester bond in an oligonucleotide converted to a phosphorothioate bond, oligonucleotide derivatives having a phosphodiester bond in an oligonucleotide converted to an N3'-P5' phosphor amidate bond, oligonucleotide derivatives having ribose and phosphodiester bond in an oligonucleotide converted to a peptide nucleic acid bond, oligonucleotide derivatives having uracil in an oligonucleotide replaced with C-5 propinyluracil, oligonucleotide derivatives having uracil in an oligonucleotide replaced with C-5 thiazoluracil, oligonucleotide derivatives having cytosine in an oligonucleotide replaced with C-5 propinylcytosine, oligonucleotide derivatives having cytosine in an oligonucleotide replaced with phenoxazine-modified cytosine, oligonucleotide derivatives having ribose in DNA replaced with 2'-O-propylribose, oligonucleotide derivatives having ribose in an oligonucleotide replaced with 2'-methoxyethoxyribose and the like. Unless noted otherwise, specific nucleic acid sequences are also intended to encompass conservatively altered variants (e.g., degenerate codon substitute) and complement sequences as well as the expressly shown sequences. Specifically, degenerate codon substitutes can be achieved by preparing a sequence with the third position of one or more selected (or all) codons substituted with a mixed base and/or deoxyinosine residue (Batzer et al., Nucleic Acid Res 19: 5081 (1991); Ohtsuka et al., J. Biol. Chem. 260: 2605-2608 (1985); Rossolini et al., Mol. Cell. Probes 8: 91-98 (1994)). As used herein, "nucleic acid" is used interchangeably with a gene, cDNA, mRNA, oligonucleotide, and polynucleotide. As used herein, "nucleotide" may be a naturally-occurring or non-naturally occurring.

As used herein, "gene" refers to an agent defining a genetic trait. "Gene" may refer to "polynucleotide", "oligonucleotide" and "nucleic acid".

As used herein, "homology" of genes refers to the level of identity of two or more genetic sequences with one another. In general, having "homology" refers to having a high level of identity or similarity. Thus, two genes with high homology have higher identity or similarity of sequences. It is possible to investigate whether two types of genes are homologous by direct comparison of sequences or, for nucleic acids, by a hybridization method under a stringent condition. When two genetic sequences are directly compared, the genes are homologous when DNA sequences are representatively at least 50% identical, preferably at least 70% identical, and more preferably at least 80%, 90%, 95%, 96%, 97%, 98%, or 99% identical between the genetic sequences. Thus, as used herein, "homolog" or "homologous gene product" refers to a protein in another species, preferably mammal, exerting the same biological function as a protein constituent of a complex which will be further described herein. Such a homolog is also called "ortholog gene product". It is understood that such a homolog, homologous gene product, ortholog gene product or the like can also be used, as long as they are in alignment with the objective of the present invention.

Amino acids may be mentioned herein by either their commonly known three letter symbols or their one character symbols recommended by the IUPAC-IUB Biochemical Nomenclature Commission. Similarly, nucleotides may be mentioned by their commonly recognized one character codes. Comparison of similarity, identity and homology of an amino acid sequence and a base sequence is calculated herein by using a default parameter using a sequence analysis tool, BLAST. For example, identity can be searched by using BLAST 2.2.28 (published on Apr. 2, 2013) of the NCBI. Herein, values for identity generally refer to a value obtained by alignment under the default condition using the above-described BLAST. However, when a higher value is obtained by changing a parameter, the highest value is considered the value of identity. When identity is evaluated in a plurality of regions, the highest value there among is considered the value of identity. Similarity is a value calculated by taking into consideration a similar amino acid in addition to identity.

In one embodiment of the present invention, "several" may be, for example, 10, 8, 6, 5, 4, 3 or 2, or a value less than any one of the values. It is known that a polypeptide with one or several amino acid residue deletions, additions, insertions, or substitutions by other amino acids maintains its biological activity (Mark et al., Proc Natl Acad Sci USA. 1984 September; 81 (18): 5662-5666., Zoller et al., Nucleic Acids Res. 1982 Oct. 25; 10(20): 6487-6500., Wang et al., Science. 1984 Jun. 29; 224 (4656): 1431-1433.). An antibody with a deletion or the like can be made, for example, by site-directed mutagenesis, random mutagenesis, biopanning using an antibody phage library or the like. For example, KOD-Plus-Mutagenes is Kit (TOYOBO CO., LTD.) can be used for site-directed mutagenesis. An antibody with the same activity as the wild-type can be selected from mutant antibodies introduced with a deletion or the like by performing various characterizations such as FACS analysis and ELISA.

In one embodiment of the present invention, "90% or greater" may be, for example, 90, 95, 96, 97, 98, 99 or 100% or greater or within the range of any two values described above. For the above-described "homology", the percentage of the number of homologous amino acids in two or a plurality of amino acid sequences may be calculated in accordance with a known method in the art. Before calculating the percentage, amino acid sequences in a group of amino acid sequences to be compared are aligned. A space is introduced in a portion of amino acid sequences when necessary to maximize the percentage of the same amino acids. An alignment method, method of calculating the percentage, comparison method, and computer programs associated therewith have been well known in the art (e.g., BLAST, GENETYX and the like). As used herein, "homology" can be represented by a value measured with BLAST of the NCBI, unless specifically noted otherwise. Blastp can be used in the default setting for an algorithm for comparing amino acid sequences with BLAST. Results of measurement are expressed in a numerical form as Positives or Identities.

As used herein, "polynucleotide which hybridizes under a stringent condition" refers to commonly used, well-known conditions in the art. Such a polynucleotide can be obtained by using a method such as colony hybridization, plaque hybridization, or southern blot hybridization while using a polynucleotide selected from among the polynucleotides of the present inventions as a probe. Specifically, the above-described polynucleotide refers to a polynucleotide that can be identified by using a filter with immobilized DNA from a colony or plaque and performing hybridization at 65° C. in the presence of 0.7-1.0 M NaCl and then using an SSC (saline-sodium citrate) solution with 0.1-2 times concentration (composition of an SSC solution with 1 time concentration is 150 mM sodium chloride and 15 mM sodium citrate) to wash the filter under the condition of 65° C. For "stringent condition", the following are examples of conditions that can be used. (1) low ionic strength and a high temperature are used for washing (e.g., 0.015 M sodium chloride/0.0015 M sodium citrate/0.1% sodium dodecyl sulfate at 50° C.), (2) a denaturing agent such as formamide is used in hybridization (e.g., 50% (v/v) formamide, 0.1% bovine serum albumin/0.1% ficoll/0.1% polyvinyl pyrrolidone/50 mM sodium phosphate buffer with a pH of 6.5, 750 mM sodium chloride, and 75 mM sodium citrate at 42° C.), or (3) a solution comprising 20% formamide, 5×SSC, 50 mM sodium phosphate (pH 7.6), 5×Denhardt's solution, 10% dextran sulfate, and 20 mg/ml denatured sheared salmon sperm DNA, is incubated overnight at 37° C. and then a filter is washed with 1×SSC at about 37-50° C. The formamide concentration may be 50% or greater. Washing time may be 5, 15, 30, 60, 120 minutes, or greater. A plurality of elements are considered to affect stringency in a hybridization reaction such as temperature, salt concentration and the like. Ausubel et al., Current Protocols in Molecular Biology, Wiley Interscience Publishers, (1995)

can be referred for details. "Highly stringent condition", for example, is 0.0015 M sodium chloride, 0.0015 M sodium citrate, and 65-68° C. or 0.015 M sodium chloride, 0.0015 M sodium citrate, 50% formamide and 42° C. Hybridization can be performed in accordance with the method described in experimental publications such as Molecular Cloning $2^{nd}$ ed., Current Protocols in Molecular Biology, Supplement 1-38, DNA Cloning 1: Core Techniques, A Practical Approach, Second Edition, Oxford University Press (1995). In this regard, a sequence comprising only an A sequence or only a T sequence is preferably excluded from a sequence that hybridizes under stringent conditions. A moderately stringent condition can be readily determined by those skilled in the art based on, for example, the length of a DNA and is shown in Sambrook et al., Molecular Cloning: A Laboratory Manual, Third Ed., Vol. 1, 7.42-7.45 Cold Spring Harbor Laboratory Press, 2001, including, for a nitrocellulose filters, use of hybridization conditions of a pre-wash solution of 1.0 mM EDTA (pH 8.0), 5×SSC, 0.5% SDS, and about 50% formamide and 2×SSC-6×SSC at about 40-50° C. (or other similar hybridization solutions such as a Stark's solution in about 50% formamide at about 42° C.) and washing conditions of 0.5×SSC, 0.1% SDS at about 60° C. Thus, the polypeptides used in the present invention encompass polypeptides encoded by a nucleic acid molecule that hybridizes under highly or moderately stringent conditions to a nucleic acid molecule encoding a polypeptide described in the present invention in particular.

As used herein, a "purified" substance or biological agent (e.g., nucleic acid, protein or the like) refers to a substance or a biological agent from which at least a part of an agent naturally accompanying the substance or biological agent has been removed. Thus, the purity of a biological agent in a purified biological agent is generally higher than the purity in the normal state of the biological agent (i.e., concentrated). The term "purified" as used herein refers to the presence of preferably at least 75% by weight, more preferably at least 85% by weight, still more preferably at least 95% by weight, and most preferably at least 98% by weight of a biological agent of the same type. The substance or biological agent used in the present invention is preferably a "purified" substance. An "isolated" substance or biological agent (e.g., nucleic acid, protein, or the like) as used herein refers to a substance or biological agent having agents that naturally accompany the substance or biological agent substantially removed. The term "isolated" as used herein varies depending on the objective. Thus, the term does not necessarily have to be represented by purity. However, when necessary, the term refers to the presence of preferably at least 75% by weight, more preferably at least 85% by weight, still more preferably at least 95% by weight, and most preferably at least 98% by weight of a biological agent of the same type. The substance used in the present invention is preferably an "isolated" substance or biological agent.

As used herein, a "corresponding" amino acid, nucleic acid, or moiety refers to an amino acid or a nucleotide which has or is expected to have, in a certain polypeptide molecule or polynucleotide molecule (e.g., LSR), similar action as a predetermined amino acid, nucleotide or moiety in a benchmark polypeptide or a polynucleotide for comparison, and, particularly in the case of enzyme molecules, refers to an amino acid which is present at a similar position in an active site and makes a similar contribution to catalytic activity and refers to a corresponding moiety in a complex molecule (e.g., transmembrane domain or the like). For example, for an antisense molecule, it can be a similar moiety in an ortholog corresponding to a specified moiety of the antisense molecule. A corresponding amino acid can be a specified amino acid subjected to, for example, cysteination, glutathionylation, S—S bond formation, oxidation (e.g., oxidation of methionine side chain), formylation, acetylation, phosphorylation, glycosylation, myristylation or the like. Alternatively, a corresponding amino acid can be an amino acid responsible for dimerization. Such a "corresponding" amino acid or nucleic acid may be a region or a domain over a certain range. Thus, it is referred herein as a "corresponding" region or domain in such a case. Such a corresponding region or domain is useful for designing a complex molecule in the present invention.

As used herein, a "corresponding" gene (e.g., polynucleotide sequence or molecule) refers to a gene (e.g., polynucleotide sequence or molecule) of a certain species which has or is expected to have similar action as a predetermined gene in a benchmark species for comparison. When there is a plurality of genes having such action, the corresponding gene refers to a gene having the same evolutionary origin. Hence, a gene corresponding to a certain gene may be an ortholog of such a gene. Thus, an LSR corresponding to human LSRs can be found in other animals (especially mammals). Such a corresponding gene can be identified by using a technique that is well known in the art. For example, a corresponding gene in a certain animal (e.g., mouse) can be found by searching a database comprising sequences of the animal from using the sequence of SEQ ID NO: 7, 8 or the like as a query sequence, as a benchmark gene of the corresponding gene (e.g., LSR or the like).

As used herein, "fragment" refers to a polypeptide or polynucleotide with a sequence length of 1 to n–1 with respect to the full length polypeptide or polynucleotide (with length n). The length of a fragment can be appropriately changed in accordance with the objective. Examples of the lower limit of such a length include 3, 4, 5, 6, 7, 8, 9, 10, 15, 20, 25, 30, 40, 50 and more amino acids for a polypeptide. Lengths represented by an integer that is not specifically listed herein (e.g., 11 and the like) also can be suitable as a lower limit. Further, examples of length include 5, 6, 7, 8, 9, 10, 15, 20, 25, 30, 40, 50, 75, 100, and more nucleotides for a polynucleotide. Lengths represented by an integer that is not specifically listed herein (e.g., 11 and the like) also can be suitable as a lower limit. As used herein, such a fragment is understood to be within the scope of the present invention, for example, when a full length version functions as a marker or a target molecule, as along as the fragment itself also functions as a marker or a target molecule.

The term "activity" according to the present invention refers to a function of a molecule in the broadest sense herein. Activity, although not intended to be limiting, generally includes a biological function, biochemical function, physical function, and chemical function of a molecule. Examples of activity include enzymatic activity, an ability to interact with another molecule, an ability to activate, promote, stabilize, inhibit, suppress, or destabilize a function of another molecule, stability, and an ability to localize at a specific position in a cell. When applicable, the term also relates to a function of a protein complex in the broadest sense.

As used herein, "biological function", when referring to a certain gene or a nucleic acid molecule or a polypeptide related thereto, refers to a specific function that the gene, the nucleic acid molecule or the polypeptide may have in a living body. Examples of such a function include, but are not limited to, production of a specific antibody, enzyme activity, impartation of resistance and the like. In the present invention, examples of this function include, but are not limited to, a function of an LSR involved in inhibition of VLDL incorporation or the like. As used herein, biological function can be exerted by "biological activity". As used herein, "biological activity" refers to the activity a certain agent (e.g., polynucleotide, protein or the like) may have in a living body. Biological activity encompasses an activity of exerting a variety of functions (e.g., transcription promoting activity), and also encompasses, for example, an activity of activating or inactivating another molecule by an interaction with a certain molecule. When two agents interact, biological activity thereof may be a bond between two molecules and a biological change induced thereby. For example, two molecules are considered to be bound together if, when one molecule is precipitated using an antibody, the other molecule co-precipitates. Observation of such co-precipitation is one example of a determination approach. For example, when a certain agent is an enzyme, the biological activity thereof encompasses enzyme activity thereof. In another example, when a certain agent is a ligand, binding to a receptor corresponding to the ligand is encompassed. Such biological activity can be measured by a technique that is well known in the art. Thus, "activity" refers to various measurable indicators, which indicate or reveal a bond (either direct or indirect) or affect a response (i.e., having a measurable effect in response to some exposures of stimuli). Examples thereof includes affinity of a compound that directly binds to the polypeptide or polynucleotide of the present invention, the amount of proteins upstream or downstream after some stimulations or events, or the level of other similar functions.

As used herein, "expression" of a gene, a polynucleotide, a polypeptide or the like refers to the gene or the like being subjected to a certain action in vivo to be converted into another form. Preferably, expression refers a gene, a polynucleotide or the like being transcribed and translated into a form of a polypeptide. However, transcription to make an mRNA is also one embodiment of expression. Thus, "expression product" as used herein encompasses such a polypeptide or protein, or mRNA. More preferably, such a polypeptide form can be a form which has undergone post-translation processing. For example, the LSR expression level can be determined by any method. Specifically, the LSR expression level can be found by assessing the amount of mRNA of LSRs, the amount of LSR protein, and the biological activity of the LSR protein. The amount of mRNA or protein of LSRs can be determined by the method described in detail in other parts of the specification or a method known in the art.

As used herein, "functional equivalent" refers to any entity having the same function of interest but a different structure relative to the original target entity. Thus, it is understood that a functional equivalent of "LSR" or an antibody thereof encompasses mutants or variants (e.g., amino acid sequence variant or the like) of the LSR or antibody thereof, not the LSR or antibody thereof itself, which have the biological action of the LSR and those that can change, upon action, into the LSR or the antibody thereof itself or a mutant or variant of the LSR or the antibody thereof (e.g., including nucleic acid encoding an LSR or an antibody thereof itself or a mutant or variant of the LSR or antibody thereof, and vector, cell and the like comprising such a nucleic acid). It is understood, even without specific mention, that a functional equivalent of an LSR or an antibody thereof can be used similarly to the LSR or antibody thereof. A functional equivalent can be found by searching a database or the like. As used herein, "search" refers to utilizing a certain nucleic acid base sequence electronically, biologically, or by another method to find another nucleic acid base sequence having a specific function and/or property. Examples of electronic search include, but are not limited to, BLAST (Altschul et al., J. Mol. Biol. 215: 403-410 (1990)), FASTA (Pearson & Lipman, Proc. Natl. Acad. Sci., USA 85: 2444-2448 (1988)), Smith and Waterman method (Smith and Waterman, J. Mol. Biol. 147: 195-197 (1981)), Needleman and Wunsch method (Needleman and Wunsch, J. Mol. Biol. 48: 443-453 (1970)) and the like. Examples of biological search include, but are not limited to, stringent hybridization, a macroarray with a genomic DNA applied to a nylon membrane or the like or a microarray with a genomic DNA applied to a glass plate (microarray assay), PCR, in situ hybridization and the like. Herein, a gene used in the present invention is intended to include corresponding genes identified by such electronic search or biological search.

As a functional equivalent of the present invention, it is possible to use an amino acid sequence with one or more amino acid insertions, substitutions or deletions, or addition to one or both ends. As used herein, "one or more amino acid insertions, substitutions or deletions, or addition to one or both ends" in an amino acid sequence refers to an alteration with a substitution of a plurality of amino acids or the like to the extent that can occur naturally by a well-known technical method such as site-directed mutagenesis or natural mutation. An altered amino acid sequence can have, for example, 1-30, preferably 1-20, more preferably 1-9, still more preferably 1-5, and especially preferably 1-2 amino acid insertions, substitutions or deletions or additions to one or both ends. Preferably, an altered amino acid sequence may be an amino acid sequence having one or more (preferably 1 or several, or 1, 2, 3 or 4) conservative substitutions in an LSR amino acid sequence. "Conservative substitution" refers herein to a substitution of one or more amino acid residues with other chemically similar amino acid residue so as not to substantially alter a function of a protein. Examples thereof include cases where a hydrophobic residue is substituted with another hydrophobic residue, cases where a polar residue is substituted with another polar residue having the same charge and the like. Functionally similar amino acids that can be substituted in this manner are known in the art for each amino acid. Specific examples include alanine, valine, isoleucine, leucine, proline, tryptophan, phenylalanine, methionine and the like for nonpolar (hydrophobic) amino acids, glycine, serine, threonine, tyrosine, glutamine, asparagine, cysteine and the like for polar (neutral) amino acids. Examples of positively charged (basic) amino acid include arginine, histidine, lysine and the like. Further, examples of a negatively-charged (acidic) amino acid include aspartic acid, glutamic acid and the like.

As used herein, "suppressant" refers to a substance or agent that inhibits biological action of a receptor or a cell against a target entity (e.g., receptor or cell). An LSR suppressant of the present invention is an agent that can temporarily or permanently reduce or eliminate a function of a target LSR, a cell expressing an LSR or the like. Examples of such a factor include, but are not limited to, antibodies, antigen binding fragments thereof, derivatives, functional equivalents, antisenses, RNAi agents such as siRNAs and other nucleic acid forms.

As used herein, "agonist" refers to a substance that expresses or enhances biological action of a receptor against a target entity (e.g., receptor). Examples thereof include natural agonists (also referred to as ligands), as well as synthesized agonists, altered agonists and the like.

As used herein, "antagonist" refers to a substance that suppresses or inhibits the expression of biological action of a receptor against a target entity (e.g., receptor). Examples thereof include natural antagonists (also referred to as ligands), as well as synthesized antagonists, altered antagonists and the like. Antagonists include those that competitively or non-competitively suppress or inhibit expression against an agonist. An antagonist can also be obtained by altering an agonist. Since physiological phenomena are suppressed or inhibited, an antagonist may be encompassed in the concept of suppressant (inhibitor) or suppressing agent. Thus, antagonists as used herein are substantially used synonymously with "suppressant".

As used herein, an "antibody" includes, in a broad sense, polyclonal antibodies, monoclonal antibodies, multi-specific antibodies, chimeric antibodies, anti-idiotype antibodies, and fragments thereof such as Fv fragments Fab' fragments, F(ab')$_2$ and Fab fragments, as well as other conjugates or functional equivalents produced by recombination (e.g., chimeric antibodies, humanized antibodies, multifunctional antibodies, bispecific or oligospecific antibodies, single chain antibodies, scFV, diabodies, sc(Fv)$_2$ (single chain (Fv)$_2$), and scFv-Fc). Furthermore, such an antibody may be fused, by a covalently bond or recombination, with an enzyme such as alkaline phosphatase, horseradish peroxidase, or a galactosidase. The anti-LSR antibody used in the present invention is sufficient if it binds to a protein of LSRs, regardless of the origin, type, shape or the like thereof. Specifically, known antibodies such as a non-human animal antibody (e.g., a mouse antibody, a rat antibody, or a camel antibody), a human antibody, a chimeric antibody, or a humanized antibody can be used. In the present invention, a monoclonal or polyclonal antibody can be utilized as an anti-LSR antibody, but a monoclonal antibody is preferable. It is preferable that an antibody binds specifically to an LSR protein.

Further, antibodies encompass modified and non-modified antibodies. Modified antibodies may be formed by an antibody binding to various molecules such as polyethylene glycol. A modified antibody can be obtained by applying a chemical modification to an antibody by using a known approach.

"Anti-LSR antibody" in one embodiment of the present invention encompasses antibodies having binding affinity to LSRs. The production method of such an anti-LSR antibody is not particularly limited. For example, the antibody may be produced by immunizing mammals or birds with an LSR.

Further, it is understood that examples of a "functional equivalent" of an "antibody to LSR (anti-LSR antibody) or a fragment thereof" includes, for antibodies, antibodies themselves having LSR binding activity and optionally suppressing activity and fragments thereof themselves, as well as chimeric antibodies, humanized antibodies, multi-functional antibodies, bispecific or oligospecific antibodies, single chain antibodies, scFV, diabodies, sc(Fv)$_2$ (single chain(Fv)$_2$), scFv-Fc and the like.

The anti-LSR antibody according to one embodiment of the present invention is preferably an anti-LSR antibody that specifically binds to a specific epitope of an LSR from the viewpoint of malignant tumor growth being particularly highly suppressed.

The anti-LSR antibody according to one embodiment of the present invention may be a monoclonal antibody. A monoclonal antibody can be made to more efficiently act against an LSR relative to a polyclonal antibody. It is preferred that a chicken is immunized with an LSR from the viewpoint of efficient production of anti-LSR monoclonal antibodies.

The antibody class of the anti-LSR antibody according to one embodiment of the present invention is not particularly limited. For example, the class may be IgM, IgD, IgG, IgA, IgE, or IgY.

The anti-LSR antibody according to one embodiment of the present invention may be an antibody fragment having antigen binding activity (hereinafter, also referred to as "antigen binding fragment"). In such a case, there is an effect of improved stability, antibody production efficiency or the like.

The anti-LSR antibody according to one embodiment of the present invention may be a fusion protein. The fusion protein may comprise a polypeptide or oligopeptide bound to the N or C-terminus of an anti-LSR antibody. The oligopeptide in this regard may be an His-tag. The fusion protein may also be fused to a mouse, human, or chicken antibody partial sequence. Such fusion proteins are also encompassed as one form of the anti-LSR antibody according to the present embodiment.

The anti-LSR antibody according to one embodiment of the present invention may be, for example, an antibody obtained via the step of immunizing an organism with a purified LSR, LSR-expressing cell, or an LSR containing lipid membrane. It is preferable that an LSR-expressing cell is used for immunization from the viewpoint of enhancing a therapeutic effect against LSR positive malignant tumor.

The anti-LSR antibody according to one embodiment of the present invent ion may be an antibody having a CDR set of an antibody obtained via the step of immunizing an organism with a purified LSR, LSR-expressing cell, or an LSR containing lipid membrane. It is preferable that an LSR-expressing cell is used for immunization from the viewpoint of enhancing a therapeutic effect against LSR positive malignant tumor. A CDR set is a set of heavy chain CDRs 1, 2, and 3 and light chain CDRs 1, 2, and 3.

"LSR expressing cell" in one embodiment of the present invention may be obtained, for example, by introducing a polynucleotide encoding an LSR into a cell and having the LSR expressed. LSRs in this regard encompass LSR fragments. Further, "LSR-containing lipid membrane" in one embodiment of the present invention may be obtained, for example, by mixing an LSR and a lipid bilayer. LSRs in this regard encompass LSR fragments. Further, the anti-LSR antibody according to one embodiment of the present invention is preferably an antibody obtained via the step of immunizing a chicken with an antigen or an antibody having a CDR set of such an antibody from the viewpoint of enhancing a therapeutic effect against LSR positive malignant tumor.

The anti-LSR antibody according to one embodiment of the present invention may have any binding strength as long as the object can be accomplished. Examples thereof include, but are not limited to, at least $1.0 \times 10^6$ or greater, $2.0 \times 10^6$ or greater, $5.0 \times 10^6$ or greater, and $1.0 \times 10^7$ or greater. The $K_D$ value (kd/ka) generally may be $1.0 \times 10^{-7}$(M) or less and can be $1.0 \times 10^{-9}$(M) or $1.0 \times 10^{-10}$ or less.

The anti-LSR antibody according to one embodiment of the present invention may have ADCC or CDC activity.

The anti-LSR antibody according to one embodiment of the present invention may be an antibody that binds to a wild-type or mutant LSR. Mutant LSRs include mutants due to a difference in the DNA sequences among individuals. The amino acid sequence of a wild-type or mutant LSR is preferably 80% or more, more preferably 90% or more, more preferably 95% or more, and especially preferably 98% or more homologous to the amino acid sequence set forth in SEQ ID NO: 8.

"Antibody" in one embodiment of the present invention encompasses molecules capable of specifically binding to a specific epitope on an antigen and populations thereof. Further, the antibody may be a polyclonal antibody or monoclonal antibody. The antibody can be present in various forms. For example, the antibody may be in one or more types of forms selected from the group consisting of a full-length antibody (antibody having an Fab region and an Fc region), Fv antibody, Fab antibody, F(ab')$_2$ antibody, Fab' antibody, diabody, single chain antibody (e.g., scFv), dsFv, multi-specific antibody (e.g., bispecific antibody), peptide or polypeptide having antigen binding affinity, chimeric antibody (e.g., mouse-human chimeric antibody, chicken-human chimeric antibody or the like), mouse antibody, chicken antibody, humanized antibody, human antibody, and similar antibodies (or equivalents). Further, the antibody encompasses modified or non-modified antibodies. Modified antibodies may be formed by an antibody binding to various molecules such as polyethylene glycol. A modified antibody can be obtained by applying a chemical modification to an antibody by using a known approach. Furthermore, such an antibody may be fused by a covalent bond or recombination with an enzyme such as alkaline phosphatase, horseradish peroxidase, or a galactosidase. The anti-LSR antibody used in the present invention is sufficient if it binds to an LSR protein, regardless of the origin, type, shape or the like thereof. Specifically, known antibodies such as a non-human animal antibody (e.g., a mouse antibody, a rat antibody, or a camel antibody), a human antibody, a chimeric antibody, or a humanized antibody can be used. In the present invention, a monoclonal or polyclonal antibody can be utilized as the anti-LSR antibody, but a monoclonal antibody is preferable. It is preferable that an antibody binds specifically to an LSR protein. Further, the antibody encompasses modified and non-modified antibodies. Modified antibodies may be formed by an antibody binding to various molecules such as polyethylene glycol. A modified antibody can be obtained by applying a chemical modification to an antibody by using a known approach.

"Polyclonal antibody" in one embodiment of the present invention can be produced, for example, by administering an immunogen comprising an antigen of interest to mammals (e.g., rat, mouse, rabbit, cow, monkey or the like), birds or the like in order to induce production of a polyclonal antibody specific to the antigen. An immunogen may be administered by one or more immunizing agents and, when desired, an injection of an adjuvant. An adjuvant may be used to increase immune responses and may comprise a Freund's adjuvant (complete or incomplete), mineral gel (aluminum hydroxide or the like), surfactant (lysolecithin or the like) or the like. Immunization protocols are known in the art and, in some cases, may be implemented by any method that induces an immune response, which matches the selected host organism (Tanpakushitsu Jikken Handobukku [*Protein experiment handbook*], Yodosha (2003): 86-91).

"Monoclonal antibody" in one embodiment of the present invention encompasses individual antibodies constituting a population being antibodies corresponding to substantially a single epitope except for antibodies having a mutation that can occur naturally in small amounts. Further individual antibodies constituting a population may be antibodies that are substantially the same except for antibodies having a mutation that can occur naturally in small amounts. Monoclonal antibodies are highly specific, which are different from common polyclonal antibodies that typically include different antibodies corresponding to different epitopes. In addition to their specificity, monoclonal antibodies are useful in that they can be synthesized from hybridoma culture which is not contaminated with other immunoglobulins. The description "monoclonal" may indicate a characteristic of being obtained from a substantially homogeneous antibody population. However, such a description does not mean that antibodies must be produced by a specific method. For example, monoclonal antibodies may be made by a method similar to a hybridoma method as described in "Kohler G, Milstein C., Mature. 1975 Aug. 7; 256 (5517): 495-497". Alternatively, monoclonal antibodies may be made by a method similar to a recombinant method as described in U.S. Pat. No. 4,816,567. Further, monoclonal antibodies may be isolated from a phage antibody library using a method similar to the technique that is described in, "Clackson et al., Mature. 1991 Aug. 15; 352 (6336): 624-628." or, "Marks et al., J Mol Biol. 1991 Dec. 5; 222 (3): 581-597". Further, monoclonal antibodies may be made by the method described in "Tanpakushitsu Jikken Handobukku [*Protein experiment handbook*], Yodosha (2003): 92-96".

Antibodies can be mass-produced by using any approach that is known in the art. Examples of construction of mass production system for a representative antibody and antibody manufacture include the following. Specifically, an H chain antibody expression vector and L chain antibody expression vector are transfected into a CHO cell. The cells are cultured by using a selection reagent G418 and Zeocin and cloned by limiting dilution. After cloning, clones stably expressing antibodies are selected by ELISA. The culture is expanded with selected CHO cells, and the culture supernatant comprising antibodies are collected. Antibodies can be purified from the collected culture supernatant by Protein A or Protein G purification.

"Fv antibody" in one embodiment of the present invention is an antibody comprising an antigen recognition site. This region comprises a dimer of one heavy chain variable domain non-covalently bound to one light chain variable domain. In this configuration, three CDRs of each variable domain can interact with one another to form an antigen binding site on the surface of a VH-VL dimer.

"Fab antibody" in one embodiment of the present invention is, for example, a fragment obtained by treating an antibody comprising an Fab region and an Fc region with proteinase papain, which is an antibody in which about half of the N-terminus side of the H chain is bound to the entire L chain via some disulfide bonds. Fabs can be obtained, for example, by treating the anti-LSR antibody according to the embodiments of the present invention comprising an Fab region and an Fc region with proteinase papain.

"F(ab')$_2$ antibody" in one embodiment of the present invention is a fragment obtained by treating an antibody comprising an Fab region and an Fc region with proteinase pepsin, which is an antibody comprising two sites corresponding to Fabs. F(ab')$_2$ can be obtained, for example, by treating the anti-LSR antibody according to the embodiments of the present invention comprising an Fab region and an Fc region with proteinase pepsin. For example, the following Fab' can be made by thioether bond or a disulfide bond.

"Fab' antibody" in one embodiment of the present invention is an antibody obtained, for example, by cleaving a disulfide bond of a hinge region of F(ab')$_2$. For example, F(ab')$_2$ can be obtained through treatment with a reducing agent dithiothreitol.

"ScFv antibody" in one embodiment of the present invention is an antibody comprising VH and VL linked with a suitable peptide linker. ScFv antibodies can be produced, for example, by obtaining a cDNA encoding VH and VL of the anti-LSR antibody according to the embodiment of the present invention, constructing a polynucleotide encoding VH-peptide linker-VL, incorporating the polynucleotide into a vector, and using a cell for expression.

"Diabody" in one embodiment of the present invention is an antibody having divalent antigen binding activity. Divalent antigen binding activity can be configured to be identical or configured such that one of them has a different antigen binding activity. A diabody can be produced, for example, by constructing a polynucleotide encoding scFv such that the length of the amino acid sequence of a peptide linker is 8 residues or less, incorporating the resulting polynucleotide into a vector and using a cell for expression.

"dsFv" in one embodiment of the present invention is an antibody in which a polypeptide introduced with cysteine residues in VH and VL is bound via a disulfide bond between the above-described cysteine residues. The position to which cysteine residues are introduced can be selected based on steric structure prediction of an antibody in accordance with the method demonstrated by Reiter et al (Reiter et al., Protein Eng. 1994 May; 7(5): 697-704).

"Peptide or polypeptide with antigen binding affinity" in one embodiment of the present invention is an antibody comprised of antibody VH, VL or CD1, 2 or 3 thereof. A peptide comprising a plurality of CDRs can be bound directly or via a suitable peptide linker.

The production method of the above-described Fv antibody, Fab antibody, F(ab')$_2$ antibody, Fab' antibody, scFv antibody, diabody, dsFv antibody, and peptide or polypeptide having antigen binding affinity (hereinafter, also referred to as "Fv antibodies") is not particularly limited. Fv antibodies can be produced, for example, by incorporating a DNA encoding a region of the Fv antibodies in the anti-LSR antibody according to the embodiment of the present invention into an expression vector and using an expression cell. Further, Fv antibodies may be produced by a chemical synthesis method such as the Fmoc (fluorenylmethyloxycarbonyl) or tBOC (t-butyloxycarbonyl) method. It should be noted that the antigen binding fragment according to one embodiment of the present invention may be one or more types of the above-described Fv antibodies.

"Chimeric antibody" in one embodiment of the present invention is, for example, a variable region of an antibody linked to a constant region of an antibody between xenogenic organisms and can be constructed by a genetic engineering technique. A mouse-human chimeric antibody can be made by, for example, the method described in "Roguska et al., Proc Natl Acad Sci USA. 1994 Feb. 1; 91 (3): 969-973." For example, the basic method of making a mouse-human chimeric antibody links a mouse leader sequence and a variable region sequence in a cloned cDNA with a sequence encoding a human antibody constant region already present in an expression vector of a mammalian cell. Further, after linking the mouse leader sequence and variable region sequence in a cloned cDNA with the sequence encoding a human antibody constant region, the resultant sequence may be linked with a mammalian cell expression vector. A fragment of a human antibody constant region can be from any human antibody H chain constant region and human antibody L chain constant region. Examples of human H chain fragment include Cγ1, Cγ2, Cγ3, and Cγ4, and examples of L chain fragment include Cλ and Cκ.

"Humanized antibody" in one embodiment of the present invention is, for example, an antibody, which has one or more CDRs from non-human species, a framework region (FR) from a human immunoglobulin, and a constant region from human immunoglobulin and binds to a desired antigen. Antibodies can be humanized by using various approaches known in the art (Almagro et al., Front Biosci. 2008 Jan. 1; 13: 1619-1633). Examples thereof include CDR grafting (Ozaki et al., Blood. 1999 Jun. 1; 93(11): 3922-3930.), Re-surfacing (Roguska et al., Proc Natl Acad Sci USA. 1994 Feb. 1; 91 (3): 969-973.), FR shuffle (Damschroder et al., Mol Immunol. 2007 April; 44 (11): 3049-3060. Epub 2007 Jan. 22.) and the like. An amino acid residue of a human FR region may be substituted with a corresponding residue from a CDR donor antibody in order to alter (preferably in order to improve) the antigen bond. The FR substitution can be implemented by a method well known in the art (Riechmann et al., Nature. 1988 Mar. 24; 332 (6162):323-327.) For example, an FR residue that is important for antigen binding may be identified by modeling an interaction between a CDR and an FR residue. Further, an abnormal FR residue at a specific position may be identified by sequence comparison.

"Human antibody" in one embodiment of the present invention is, for example, an antibody in which a region comprising a variable region and constant region of a heavy chain and variable region and constant region of a light chain constituting the antibody is derived from a gene encoding a human immunoglobulin. Main production methods include a method using a transgenic mouse for making human antibodies, phage display and the like. A method using a transgenic mouse for making human antibodies produces human antibodies with diverse antigen binding capabilities instead of mouse antibodies when a functional human Ig gene is introduced into an endogenous Ig knockout mouse. Furthermore, this mouse can be immunized to obtain human monoclonal antibodies by a conventional hybridoma method. Such antibodies can be made, for example, by the method described in "Lonberg et al., Int Rev Immunol. 1995; 13 (1): 65-93." Phase display is a system that typically expresses an exogenous gene as a fusion protein such that phage infectivity is not lost on the N-terminus side of a coat protein (g3p, g10p, or the like) of fibrous phage such as M13 or T7 which is an *E. coli* virus. Antibodies can be made, for example, by the method described in "Vaughan et al., Nat Biotechnol. 1996 March; 14 (3): 309-314".

Further, antibodies may be prepared by grafting a heavy chain CDR or light chain CDR of the anti-LSR antibody according to the embodiment of the present invention onto any antibody by CDR-grafting (Ozaki et al., Blood. 1999 Jun. 1; 93(11): 3922-3930). Further, antibodies can be obtained by linking a DNA encoding a heavy chain CDR or light chain CDR of the anti-LSR antibody according to the embodiment of the present invention and a DNA encoding a region excluding a heavy chain CDR or light chain CDR of a known antibody derived from a human or a non-human organism to a vector in accordance with a known method in the art and using a known cell for expression. When obtaining antibodies in this manner, a known method in the art (e.g., method of allowing amino acid residues of an antibody to randomly mutate and screening for antibodies with high reactivity, phage display, or the like) may be used to optimize the region excluding a heavy chain CDR or light chain CDR in order to enhance the efficiency of anti-LSR antibody acting upon a target antigen. Further, an FR region may be optimized by using, for example, FR shuffle (Damschroder et al., Mol Immunol. 2007 April; 44 (11): 3049-3060. Epub 2007 Jan. 22.) or a method of replacing a vernier zone amino acid residue or packaging residue (Japanese Laid-Open Publication No. 2006-241026 or Foote et al., J Mol Biol. 1992 Mar. 20; 224(2): 487-499).

"Heavy chain" in one embodiment of the present invention is typically the main constituent element of a full-length antibody. A heavy chain is generally bound to a light chain by a disulfide bond and non-covalent bond. A region called a variable region (VH) which has an amino acid sequence that is not constant even among antibodies in the same class of the same species, is present in a domain on the N-terminus side of a heavy chain. VH is generally known to greatly contribute to the specificity and affinity to an antigen. For example, "Reiter et al., J Mol Biol. 1999 Jul. 16; 290(3): 685-98." describes that a molecule with only a VH, when made, bound to an antigen with specificity and high level of affinity. Furthermore, "Wolfson W, Chem Biol. 2006 December; 13 (12): 1243-1244." describes that there are antibodies having only a heavy chain without a light chain among camel antibodies.

"CDR (complementarity determining region)" in one embodiment of the present invention is a region that is in actual contact with an antigen to form a binding site in an antibody. CDRs are generally located on an Fv (variable region: including heavy chain variable region (VH) and light chain variable region (VL)) of an antibody. Further, CDRs generally have CDR1, CDR2, and CDR3 consisting of about 5-30 amino acid residues. In addition, CDRs of a heavy chain are particularly known for their contribution to binding of an antibody to an antigen. Among the CDRs, CDR3 is known to contribute the most in binding of an antibody to an antigen. For example, "Willy et al., Biochemical and Biophysical Research Communications Volume 356, Issue 1, 27 Apr. 2007, Pages 124-128" describes that a heavy chain CDR3 was altered to elevate the binding capability of an antibody. An Fv region other than the CDRs is called a framework region (FR), consisting of FR1, FR2, FR3, and FR4, which are conserved relatively well among antibodies (Kabat et al., "Sequence of Proteins of Immunological Interest" US Dept. Health and Human Services, 1983.) Specifically, a factor characterizing the reactivity of an antibody is considered to be in CDRs, especially heavy chain CDRs.

A plurality of methods for defining CDRs and determining the positions thereof have been reported. For example, the Kabat definition (Sequences of Proteins of Immunological Interest, 5th ed., Public Health Service, National Institutes of Health, Bethesda, Md. (1991)) or the Chothia definition (Chothia et al., J. Mol. Biol., 1987; 196: 901-917) may be used. One embodiment of the present invention uses the Kabat definition as an optimal example, but the definition is not necessarily limited thereto. Further, the definitions may be determined in some cases after considering both the Kabat definition and the Chonthia definition. For example, an overlapping portion of CDR according to each of the definitions, or a portion comprising both CDRs according to each of the definitions can be deemed the CDR. A specific example of such a method is the method of Martin et al using Oxford Molecular's AbM antibody modeling software, which is a proposal combining the Kabat definition and the Chonthia definition (Proc. Natl. Acad. Sci. USA, 1989; 86: 9268-9272). Such CDR information can be used to produce a mutant that can be used in the present invention. Such an antibody mutant comprises one or several (e.g., 2, 3, 4, 5, 6, 7, 8, 9, and 10) substitutions, additions, or deletions in the framework of the original antibody. However, a mutant can be produced such that the CDR does not comprise a mutation.

As used herein, "antigen" refers to any substrate that can be specifically bound by an antibody molecule. As used herein, "immunogen" refers to an antigen that can initiate lymphocyte activation which leads to an antigen specific immune response. As used herein, "epitope" or "antigen determinant" refers to a site in an antigen molecule to which an antibody or a lymphocyte receptor binds. A method of determining an epitope is well known in the art. Such an epitope can be determined by those skilled in the art by using a well-known and conventional technique when a primary sequence of an amino acid or a nucleic acid is provided. It is understood that the antibody of the present invention can be similarly used even for antibodies having other sequences, as long as the epitope is the same.

It is understood that antibodies with any specificity may be used as the antibody used herein, as long as false positive reactions are reduced. Thus, the antibodies used in the present invention may be a polyclonal antibody or a monoclonal antibody.

As used herein, "means" refers to anything that can be a tool for accomplishing an objective (e.g., detection, diagnosis, therapy). As used herein, "selective recognizing means" in particular refers to means capable of recognizing a certain subject differently from others.

As used herein, "marker (substance, protein or gene)" refers to a substance that can be an indicator for tracking whether a target is in or at risk of being in a certain condition (e.g., diseased state, disorder state, level of or presence of malignant state or the like). Examples of such a marker include genes, gene products, metabolites, enzymes and the like. In the present invention, detection, diagnosis, prognosis, poor prognosis, diagnosis of poor prognosis, diagnosis of prognostic state, preliminary detection, prediction, or prediagnosis of a certain state (e.g., state of a disease such as cancer) can be materialized by using an agent or means specific to a marker associated with such a state, or a composition, kit or system comprising the same or the like. As used herein, "expression product" (also referred to as a gene product) refers to a protein or mRNA encoded by a gene. It is found in the present specification that a gene product (LSR), which does not exhibit association with malignant tumor, especially to therapy thereof, can be used as an indicator for ovarian cancer.

"Malignant tumor" as used herein includes, for example, tumor that develops from a mutation of normal cells. Malignant tumor can develop from any organ or tissue of the entire body. Such malignant tumor comprises one or more type selected from the group consisting of lung cancer, esophageal cancer, gastric cancer, liver cancer, pancreatic cancer, renal cancer, adrenal cancer, bile duct cancer, breast cancer, colon cancer, small intestine cancer, ovarian cancer, uterine cancer, bladder cancer, prostate cancer, ureteral cancer, renal pelvis cancer, ureteral cancer, penile cancer, testicular cancer, cerebral tumor, cancer of the central nervous system, cancer of the peripheral nervous system, head and neck cancer, glioma, glioblastoma multiform, skin cancer, melanoma, thyroid cancer, salivary gland cancer, malignant lymphoma, carcinoma, sarcoma, and hematologic malignancy. Ovarian cancer in this regard includes, for example, ovarian serous adenocarcinoma and ovarian clear cell adenocarcinoma. Uterine cancer includes, for example, endometrial cancer and cervical cancer. Head and neck cancer includes, for example, or al cavity cancer, pharyngeal cancer, nasal cavity cancer, paranasal cancer, salivary gland cancer, and thyroid cancer. Lung cancer includes, for example, non-small-cell lung cancer and small cell lung cancer. Further, malignant tumor may be LSR positive.

Among malignant tumor, serous adenocarcinoma is cancer that progresses very rapidly. It is difficult to completely eliminate the cancer even with commercially available anticancer agents. Furthermore, in recurrences, commercially available anticancer agents hardly have any effect thereon. Further, hardly any therapeutic effect can be expected on clear cell adenocarcinoma by commercially available anticancer agents. Meanwhile, the anti-LSR antibody according to the embodiment of the present invention can be a novel therapeutic drug for serous adenocarcinoma and clear cell adenocarcinoma.

"LSR positive malignant tumor" in one embodiment of the present invention includes malignant tumor that significantly expresses or overexpresses LSRs. Whether malignant tumor is LSR positive may be assessed, for example, by RT-PCR, Western blot, or immunohistochemically staining method. Further, when total protein of malignant tumor cells is subjected to Western blot and a band corresponding to LSRs (e.g., band near 649aa) can be observed by visual inspection, the malignant tumor may be determined as LSR positive. Further, when the amount of LSR expression of malignant tumor cells from a patient is significantly more than for normal cells, the malignant tumor may be determined as LSR positive. It is preferable that an anti-LSR antibody is used to inspect LSR expression from the viewpoint of materializing a more optimal dosing by accurately diagnosing malignant tumor as LSR positive.

As used herein, "subject (person)" refers to a target subjected to diagnosis, detection, therapy or the like of the present invention (e.g., an organism such as a human or a cell, blood, serum or the like extracted from an organism).

As used herein, "sample" refers to any substance obtained from a subject or the like. For example, serum and the like are encompassed thereby. Those skilled in the art can appropriately select a preferred sample based on the descriptions herein.

As used herein, "agent" is used broadly and may be any substance or other elements (e.g., energy, radiation, heat, electricity and other forms of energy) as long as the intended objective can be achieved. Examples of such a substance include, but are not limited to, protein, polypeptide, oligopeptide, peptide, polynucleotide, oligonucleotide, nucleotide, nucleic acid (including, for example, DNAs such as cDNA and genomic DNA and RNAs such as mRNA), polysaccharide, oligosaccharide, lipid, organic small molecule (e.g., hormone, ligand, information transmitting substance, organic small molecule, molecule synthesized by combinatorial chemistry, small molecule that can be used as medicine (e.g., small molecule ligand and the like)) and a complex molecule thereof. Typical examples of an agent specific to a polynucleotide include, but are not limited to, a polynucleotide having complementarity with a certain sequence homology (e.g., 70% or greater sequence identity) to a sequence of the polynucleotide, polypeptide such as a transcription factor that binds to a promoter region and the like. Typical examples of an agent specific to a polypeptide include, but are not limited to, an antibody directed specifically to the polypeptide or a derivative or analog thereof (e.g., single stranded antibody), a specific ligand or receptor when the polypeptide is a receptor or ligand, a substrate when the polypeptide is an enzyme and the like.

As used herein, "diagnosis" refers to identifying various parameters associated with a disease, disorder, condition (e.g., malignant tumor) or the like in a subject to determine the current or future state of such a disease, disorder, or condition. The condition in the body can be investigated by using the method, apparatus, or system of the present invention. Such information can be used to select and determine various parameters of a formulation or method for the treatment or prevention to be administered, disease, disorder, or condition in a subject or the like. As used herein, "diagnosis" when narrowly defined refers to diagnosis of the current state, but when broadly defined includes "early diagnosis", "predictive diagnosis", "prediagnosis" and the like. Since the diagnostic method of the present invention in principle can utilize what comes out from a body and can be conducted away from a medical practitioner such as a physician, the present invention is industrially useful. In order to clarify that the method can be conducted away from a medical practitioner such as a physician, the term as used herein may be particularly called "assisting" "predictive diagnosis, prediagnosis or diagnosis".

The term "prognosis" as used herein refers to prediction of the possibility of progression or death due to cancer, such as the possibility of recurrence, metastasis and diffusion, drug resistance and the like of a neoplastic disease such as malignant tumor (e.g., ovarian cancer). Thus, as used herein, "excellent prognostic state" refers to a state where recurrence of primary cancer is not observed beyond a certain period of time (e.g., 4 years) after removal of the cancer tissue, and "poor prognostic state" or "poor prognosis" refers to a state where recurrence of primary cancer is observed beyond a certain period of time (e.g., 4 years) after removal of the cancer tissue. A prognostic agent is a variable related to natural course of malignant tumor, which affects the rate of recurrence of outcome of a patient who has experienced malignant tumor. Examples of clinical indicator associated with exacerbation in prognosis include lymph node metastasis and highly malignant tumor. A prognostic agent is often used to classify patients into subgroups with different fundamental risks of recurrence. In this manner, expression of LSRs of the present invention can be used as a prognostic agent. The term "prediction" as used herein refers to the possibility of a patient having a specific clinical outcome, regardless of good or bad, after extraction of primary tumor. Thus, LSRs of the present invention can be used as a poor prognosis marker. A therapeutic method can be determined by clinically using the prediction method of the present invention to select the optimal therapeutic method for a specific patient. The prediction method of the present invention would be a beneficial means for prediction if there is a possibility that a patient would have a positive reaction to a therapeutic regimen, e.g., surgical intervention or the like. A prognostic agent can be included in the prediction.

As used herein, "detecting drug (agent)" or "inspection drug (agent)" broadly refers to all agents capable of detecting or inspecting a target of interest.

As used herein, "diagnostic drug (agent)" broadly refers to all agents capable of diagnosing a condition of interest (e.g., disease such as malignant tumor or the like).

As used herein, "therapy" refers to the prevention of exacerbation, preferably maintaining of the current condition, more preferably alleviation, and still more preferably disappearance of a disease or disorder (e.g., malignant tumor) in case of such a condition, including being capable of exerting a prophylactic effect or an effect of improving a disease of a patient or one or more symptoms accompanying the disease. Preliminary diagnosis with suitable therapy may be referred to as "companion therapy" and a diagnostic agent therefor may be referred to as "companion diagnostic agent".

As used herein, "therapeutic drug (agent)" broadly refers to all agents capable of treating a condition of interest (e.g., diseases such as malignant tumor or the like). In one embodiment of the present invention, "therapeutic drug" may be a pharmaceutical composition comprising an effective ingredient and one or more pharmacologically acceptable carriers. A pharmaceutical composition can be manufactured, for example, by mixing an effective ingredient and the above-described carriers by any method known in the technical field of pharmaceuticals. Further, mode of usage of a therapeutic drug is not limited, as long as it is used for therapy. A therapeutic drug may be an effective ingredient alone or a mixture of an effective ingredient and any ingredient. Further, the shape of the above-described carriers is not particularly limited. For example, the carrier may be a solid or liquid (e.g., buffer solution). It should be noted that a therapeutic drug of malignant tumor includes a drug (prophylactic drug) for preventing malignant tumor or a growth suppressant for malignant tumor cells.

As used herein, "prevention" refers to the action of taking a measure against a disease or disorder (e.g., malignant tumor) from being in such a condition prior to being in such a condition. For example, it is possible to use the agent of the present invention to perform diagnosis, and optionally use the agent of the present invention to prevent or take measures to prevent malignant tumor or the like.

As used herein, "prophylactic drug (agent)" broadly refers to all agents capable of preventing a condition of interest (e.g., diseases such as malignant tumor or the like).

As used herein, "interaction" refers, for two substances, to applying a force (e.g., intermolecular force (Van der Waals force), hydrogen bond, hydrophobic interaction, or the like) between one substance and the other substance. Generally, two substances that have interacted are in a conjugated or bound state. The detection, inspection, and diagnosis in the present invention can be materialized by utilizing such interaction.

As used herein, the term "bond" refers to a physical or chemical interaction between two substances or between combinations thereof. A bond includes an ionic bond, non-ionic bond, hydrogen bond, Van der Waals bond, hydrophobic interaction and the like. A physical interaction (bond) may be direct or indirect. Indirect physical interaction (bond) is mediated by or is due to an effect of another protein or compound. A direct bond refers to an interaction, which does not occur through or due to an effect of another protein or compound and does not substantially involve another intermediate.

Thus, an "agent" (or detection agent or the like) that "specifically" interacts (or binds) to a biological agent such as a polynucleotide or a polypeptide as used herein encompasses agents with affinity to the biological agent such as a polynucleotide or polypeptide that is typically similar or higher, preferably significantly (e.g., statistically significantly) higher, than affinity to other unrelated polynucleotides or polypeptides (especially those with less than 30% identity). Such affinity can be measured, for example, by hybridization assay, binding assay or the like.

As used herein, "specific" interaction (or bond) of a first substance or agent with a second substance or agent refers to the first substance or agent interacting with (or binding to) the second substance or agent at a higher level of affinity than to substances or agents other than the second substance or agent (especially other substances or agents in a sample comprising the second substance or agent). Examples of an interaction (or bond) specific to a substance or agent include, but are not limited to, hybridization in a nucleic acid, antigen-antibody reaction in a protein, enzyme-substrate reaction, other nucleic acid protein reactions, protein-lipid interaction, nucleic acid-lipid interaction and the like. Thus, when substances or agents are both nucleic acids, a first substance or agent "specifically interacting" with a second substance or agent encompasses the first substance or agent having at least partial complementarity to the second substance or agent. Further, examples of a first substance or agent "specifically" interacting with (or binding to) a second substance or agent when substances or agents are both proteins include, but are not limited to, interaction by an antigen-antibody reaction, interaction by a receptor-ligand reaction, enzyme-substrate interaction and the like. When two types of substances or agents include a protein and a nucleic acid, a first substance or agent "specifically" interacting with (or binding to) a second substance or factor encompasses an interaction (or a bond) between an antibody and an antigen. Such a specific interactive or binding reaction can be utilized to detect or quantify a target in a sample.

As used herein, "detection" or "quantification" of polynucleotide or polypeptide expression can be accomplished by using a suitable method including, for example, an immunological measuring method and measurement of mRNAs, including a bond or interaction to a detection agent, inspection agent or diagnostic agent. Examples of a molecular biological measuring method include northern blot, dot blot, PCR and the like. Examples of an immunological measurement method include ELISA using a microtiter plate, RIA, fluorescent antibody method, luminescence immunoassay (LIA), immunoprecipitation (IP), single radial immunodiffusion (SRID), turbidimetric immunoassay (TIA), western blot, immunohistochemical staining and the like. Further, examples of a quantification method include ELISA, RIA and the like. Quantification may also be performed by a gene analysis method using an array (e.g., DNA array, protein array). DNA arrays are outlined extensively in (Ed. by Shujunsha, Saibo Kogaku Bessatsu "DNA Maikuroarei to Saishin PCR ho" [*Cellular engineering, Extra issue, "DNA Microarrays and Latest PCR Methods"*]. Protein arrays are discussed in detail in Nat Genet. 2002 December; 32 Suppl: 526-32. Examples of a method of analyzing gene expression include, but are not limited to, RT-PCR, RACE, SSCP, immunoprecipitation, two-hybrid system, in vitro translation and the like, in addition to the methods discussed above. Such additional analysis methods are described in, for example, Genomu Kaiseki Jikkenho Nakamura Yusuke Labo Manyuaru [*Genome analysis experimental method Yusuke Nakamura Lab Manual*], Ed. by Yusuke Nakamura, Yodosha (2002) and the like. The entirety of the descriptions therein is incorporated herein by reference.

As used herein, "amount of expression" refers to the amount of polypeptide, mRNA or the like expressed in a cell, tissue or the like of interest. Examples of such an amount of expression include amount of expression of the polypeptide of the present invention at a protein level assessed by any suitable method including an immunological measurement method such as ELISA, RIA, fluorescent antibody method, western blot, and immunohistochemical staining by using the antibody of the present invention, and the amount of expression of the polypeptide used in the present invention at an mRNA level assessed by any suitable method including a molecular biological measuring method such as northern blot, dot blot, and PCR. "Change in amount of expression" refers to an increase or decrease in the amount of expression of the polypeptide used in the present invention at a protein level or mRNA level assessed by any suitable method including the above-described immunological measuring method or molecular biological measuring method. A variety of detection or diagnosis based on a marker can be performed by measuring the amount of expression of a certain marker.

As used herein, "decrease" or "suppression" of activity or expression product (e.g., protein, transcript (RNA or the like)) or synonyms thereof refers to: a decrease in the amount, quality or effect of a specific activity, transcript or protein; or activity that decreases the same. Among decrease, "elimination" refers to activity, expression product or the like being less than the detection limit and especially referred to as "elimination". As used herein, "elimination" is encompassed by "decrease" or "suppression".

As used herein, "increase" or "activation" of activity or expression product (e.g., protein, transcript (RNA or the like)) or synonyms thereof refers to: an increase in the amount, quality or effect of a specific activity, transcript or protein; or activity that increases the same.

As used herein, "(nucleic acid) primer" refers to a substance required for initiating a reaction of a polymeric compound to be synthesized in a polymer synthesizing enzyme reaction. A synthetic reaction of a nucleic acid molecule can use a nucleic acid molecule (e.g., DNA, RNA or the like) complementary to a portion of a sequence of a polymeric compound to be synthesized.

A primer can be used herein as a marker detecting means.

As used herein, "probe" refers to a substance that can be means for search, which is used in a biological experiment such as in vitro and/or in vivo screening. Examples thereof include, but are not limited to, a nucleic acid molecule comprising a specific base sequence, a peptide comprising a specific amino acid sequence, a specific antibody, a fragment thereof and the like. As used herein, a probe is used as means for marker detection, inspection, or diagnosis.

As used herein, "label" refers to an entity (e.g., substance, energy, electromagnetic wave or the like) for distinguishing a molecule or substance of interest from others. Such a method of labeling includes RI (radioisotope) method, fluorescence method, biotin method, chemiluminescent method and the like. When a plurality of markers of the present invention or agents or means for capturing the same are labeled by a fluorescence method, labeling is performed with fluorescent substances having different fluorescent emission maximum wavelengths. It is preferable that the difference in fluorescent emission maximum wavelengths is 10 nm or greater. When labeling a ligand, any label that does not affect the function can be used. However, Alexa™Fluor is desirable as a fluorescent substance. Alexa™Fluor is a water-soluble fluorescent dye obtained by modifying coumarin, rhodamine, fluorescein, cyanine or the like. This is a series compatible with a wide range of fluorescence wavelengths. Relative to other fluorescent dyes for the corresponding wavelength, Alexa™Fluor is very stable, bright and has a low level of pH sensitivity. Combinations of fluorescent dyes with fluorescence maximum wavelength of 10 nm or greater include a combination of Alexa™555 and Alexa™633, combination of Alexa™488 and Alexa™555 and the like. When a nucleic acid is labeled, any label can be used that can bind to abase portion thereof. However, it is preferable to use a cyanine dye (e.g., Cy3, Cy5 or the like of the CyDye™ series), rhodamine 6G reagent, 2-acetylaminofluorene (AAF), AAIF (iodine derivative of AAF) or the like. Examples of a fluorescent substance with a difference in fluorescent emission maximum wavelengths of 10 nm or greater include a combination of Cy5 and a rhodamine 6G reagent, a combination of Cy3 and fluorescein, a combination of a rhodamine 6G reagent and fluorescein and the like. The present invention can utilize such a label to alter a subject of interest to be detectable by the detecting means to be used. Such alteration is known in the art. Those skilled in the art can appropriately carryout such a method in accordance with the label and subject of interest.

As used herein, "tag" refers to a substance for distinguishing a molecule by a specific recognition mechanism such as receptor-ligand, or more specifically, a substance serving the role of a binding partner for binding a specific substance (e.g., having a relationship such as biotin-avidin or biotin-streptavidin). A tag can be encompassed in the scope of "label". Accordingly, a specific substance to which a tag is bound can distinguish the specific substance by a contact with a substrate, to which a binding partner of a tag sequence is bound. Such a tag or label is well known in the art. Typical tag sequences include, but are not limited to, myc tag, His tag, HA, Avi Tag™ (Avidity LLC, Aurora, Colo.) and the like. Such a tag may be bound to the marker of the present invention or a detection agent, inspection agent, or diagnostic agent (may be a primer, probe or the like) of the marker.

As used herein, "in vivo" refers to inside of a living body. In specific context, "in a living body" refers to the position where a substance of interest should be disposed.

As used herein, "in vitro" refers to a state where a portion of a living body is extracted or freed "outside of a living body" (e.g., in a test tube) for various research purposes. This is a term that is an antonym of in vivo.

As used herein, when a procedure is performed outside of the body, but the subject of the procedure is intended to be subsequently returned in the body, the series of operations is referred to as "ex vivo". An embodiment that treats a cell in a living body with an agent of the present invention and returns the cell in a patient is also anticipated in the present invention.

As used herein, "kit" refers to a unit generally providing portions to be provided (e.g., inspection drug, diagnostic drug, therapeutic drug, antibody, label, manual and the like) into two or more separate sections. This form of a kit is preferred when a composition that should not be provided in a mixed state and is preferably mixed immediately before use for safety or the like is intended to be provided. Such a kit advantageously comprises an instruction or manual describing how the provided portions (e.g., inspection drug, diagnostic drug, or therapeutic drug) are used or how a reagent should be handled. When the kit is used herein as a reagent kit, the kit generally comprises an instruction describing how to use an inspection drug, diagnostic drug, therapeutic drug, antibody and the like.

As used herein, "instruction" is a document with an explanation of the method of use of the present invention for a physician or other users. The instruction has a description of the detection method of the present invention, method of use of a diagnostic agent, or administration of a medicament or the like. Further, an instruction may have a description instructing or al administration or administration to the esophagus (e.g., by injection or the like) as a site of administration. The instruction is prepared in accordance with a format defined by the regulatory agency of the country in which the present invention is practiced (e.g., the Ministry of Health, Labor and Welfare in Japan, Food and Drug Administration (FDA) in the U.S. or the like), with an explicit description showing approval by the regulatory agency. The instruction is a so-called package insert and is typically provided in, but not limited to, paper media. The instructions may also be provided in a form such as electronic media (e.g., web sites provided on the Internet or emails).

Preferred Embodiments

Preferred embodiments of the present invention are described hereinafter. The embodiments are provided hereinafter for better understanding of the present invention. It is understood that the scope of the present invention should not be limited to the following descriptions. Thus, it is apparent that those skilled in the art can readily make modifications within the scope of the present invention while referring to the descriptions herein. It is understood that the following embodiments of the present invention can be used alone or in combine.

(Therapy and Prevention of Malignant Tumor)

In one aspect, the present invention provides a novel therapeutic or prophylactic drug for malignant tumor. The therapeutic or prophylactic drug is a therapeutic or prophylactic drug for malignant tumor, comprising an LSR suppressant (e.g., anti-LSR antibody). LSR positive malignant tumor can be treated or prevented by using such a therapeutic or prophylactic agent. Since such a therapeutic or prophylactic drug uses antibodies, it is an excellent drug from the viewpoint of safety.

There are LSR positive and LSR non-positive patients or patients who may be in such a group in malignant tumor patients or patients who may be in such a group. For this reason, it is preferable that the therapeutic drug of the present invention is administered to a patient among the malignant tumor patients who is determined to have malignant tumor that is LSR positive malignant tumor. In this manner, a drug can be administered more optimally by diagnosing in advance the presence of LSR positive.

In one specific embodiment, the composition or medicament (therapeutic drug, prophylactic drug or the like) of the present invention is formulated in anticipation of implementation in administration to a patient determined to have an episode of LSR positive malignant tumor.

In one embodiment, the LSR suppressant used in the present invention is an antibody, a fragment or a functional equivalent thereof, or a nucleic acid.

In a specific embodiment, the LSR suppressant used in the present invention preferably has the ability to inhibit exacerbation due to VLDL. In a more specific embodiment, the LSR antibody of the present invention is an antibody having the ability to inhibit exacerbation due to VLDL. Although not wishing to be bound by any theory, LSRs affect cancer growth by incorporating VLDL and enhancing lipid metabolism. That is, it is understood that suppression of LSR functions in cancer cells expressing LSRs results in enhanced suppression of cancer cell growth. The antibodies of the present invention can suppress VLDL incorporation into LSRs of cancer cells to enhance suppression of cancer cell growth. Thus, target cancer or cancer cells of the present invention may be cancer or cells associated with VLDL (e.g., cancer shown in the Examples or cancer associated with cancer cells, ovarian cancer or the like). In a specific embodiment, the LSR suppressant used in the present invention is a nucleic acid, which is an antisense nucleic acid, siRNA or the like. Specifically, the siRNA may comprise SEQ ID NO: 9-14 or the like.

In another embodiment, the LSR suppressantis an antibody or a fragment or a functional equivalent thereof. The antibody of the present invention may be a specific sequence described in other parts of the present specification. The antibody may be an antibody or antigen binding fragment thereof comprising any sequence comprising CDRs of the full length sequence, or an antibody or antigen binding fragment thereof comprising a variable region of the following sequence, the framework region thereof comprising 1, 2, 3, 4, 5, 6, 7, 8, 9, 10, 12, 15, 17, 20 or more substitutions, additions, or deletions. The antibody can be manufactured by using an embodiment described in other parts of the specification and/or an approach known in the art. For therapy or prevention of the present invention, it is preferable that such an antibody or a fragment or functional equivalent thereof has activity to suppress LSRs or downstream information transmitting pathway thereof. Such activity may be confirmed by observing the amount of expression or activity of LSRs, or by directly using malignant tumor cell strains such as ovarian clear cell adenocarcinoma to observe inhibition of cell growth, cytotoxic activity with antibody-dependent cell-mediated cytotoxicity (ADCC), tumor regression after transplantation into model animals or the like. Such approaches are well known in the art, while the approach used herein may also be used.

In another aspect, the present invention provides a method of preventing or treating malignant tumor of a subject, comprising administering an effective amount of LSR suppressant to the subject in need thereof. It is understood that any form described in other parts of the present specification can be used as the LSR suppressant used in the prophylactic or therapeutic method of the present invention.

In another aspect, the present invention also provides a composition or a medicament (therapeutic drug or prophylactic drug) for preventing or treating malignant tumor, comprising an LSR binding agent. In a preferred embodiment, the composition or medicament (therapeutic drug, prophylactic drug or the like) further comprises a cell-killing agent. Thus, such a composition or medicament (therapeutic drug, prophylactic drug or the like) may include a complex molecule.

In a specific embodiment, the LSR binding agent is an antibody, a fragment or a functional equivalent thereof, or a nucleic acid. In a preferred embodiment, the LSR binding agent is an antibody or a fragment or a functional equivalent thereof, further bound to a cell-killing agent.

As used herein, "cell-killing agent" is an agent that may dissolve a cell membrane. When the agent is a peptide, the cell killing agent is called a cytotoxic peptide. Cytotoxic peptide has various nomenclatures in the art. For example, "soluble peptidic component" and "cell-killing sequence" are also called "cytolic peptide (sequence)", "cell dissolving peptide (sequence)" or the like. However, they are used synonymously in the content of the present invention. Representative examples of such a cytotoxic agent include those listed in Gail D. et al., Cancer Res 2008; 68: 9280-9290.; Ian Krop and Eric P. Winer, Clin Cancer Res; 20(1); 1-6. and K Naito et al., Leukemia (2000) 14, 1436-144, as well as, but not limited to, maytansinoid, emtansine, N-acetyl-γ calicheamicin dimethyl hydrazide (NAc-γ calicheamicin, DMH) comprised in CMA-676 and the like. Representative cell killing peptide includes, but is not limited to, cell membrane dissolving peptide, cell membrane potential destabilizing peptide, cell membrane dissolving/nucleic acid binding peptide, and mitochondrial membrane disintegrating peptide.

Such a cell-killing agent may be bound to the binding agent of the present invention such as an antibody with a spacer as needed. As used herein, "spacer" refers to a moiety that forms a chemical bond between molecules of chain-like polymers so as to bridge the molecules. Such a spacer is also called a linker. Representative spacers of a peptide include, but are not limited to, a sequence of 0-5 amino acids consisting of G and P. A spacer is not essential and may not be present.

A combination of the binding agent of the present invention and cell-killing agent can also be considered a complex molecule. An example is provided to explain such a molecule. Such a molecule can be explained as a molecule made by combining a cytotoxic portion corresponding to the explosive charge portion and a portion responsible for specificity to a cancer cell corresponding to the warhead portion (e.g., peptide/sequence that specifically binds to a receptor which is highly expressed in cancer cells, typically an antibody). When a spacer is used, the molecule would be comprised of a cancer cell specific binding agent+spacer+ cell-killing agent. Any cancer specific binding agent, any spacer, and any cell-killing agent can be combined herein in any manner. Examples of a manufacturing method and usage method thereof are described. Such a molecule is generally made by a chemical synthesis method, but when such a molecule is comprised of peptides, a method of forced expression and purification by genetic engineering or a method combining such a method can also be used.

For use of the present invention, LSR expression on the cell surface and sensitivity to damage of cancer cells to cell-killing agent are investigated for cancer cells to be subjected to therapy. Warhead and explosive charge are selected base on the result thereof to design an optimal molecule for the cancer cell. A custom-made peptide toxin obtained from chemical synthesis or the like can be combined as needed with DDS such as atelocollagen and administered locally or systemically for therapy.

In one embodiment, an LSR binding agent is an antibody or a fragment or a functional equivalent thereof. The antibody can be a sequence specifically listed in other parts of the present specification.

It is preferable that an administration pathway of a therapeutic drug that is effective in therapy is used. For example, the administration pathway may be intravenous, subcutaneous, intramuscular, intraperitoneal, or al administration or the like. The mode of administration may be, for example, injection, capsule, tablet, granule or the like. When an antibody or polynucleotide is administered, use thereof as an injection is effective. An aqueous solution for injection may be stored, for example, in a vial or a stainless streel container. Further, an aqueous solution for injection may contain, for example, saline, saccharide (e.g., trehalose), NaCl, NaOH or the like. Further, a therapeutic drug may contain a buffer (e.g., phosphate buffer), stabilizer or the like.

The composition, medicament, therapeutic agent, prophylactic agent and the like of the present invention generally comprise a therapeutically effective amount of therapeutic agent or effective ingredient and a pharmaceutically acceptable carrier or excipient. As used herein, "pharmaceutically acceptable" means that government regulatory agency-approved or pharmacopoeia or other commonly recognized pharmacopoeia-listed for use in animals and more specifically in humans. As used herein "carrier" refers to a diluent, adjuvant, excipient or vehicle administered in conjunction with a therapeutic agent. Such a carrier can be an aseptic liquid such as water or oil, including but not limited to liquids derived from petroleum, animal, plant or synthesis, as well as peanut oil, soybean oil, mineral oil, sesame oil and the like. When a medicament is or ally administered, water is a preferred carrier. For intravenous administration of a pharmaceutical composition, saline and aqueous dextrose are preferred carriers. Preferably, aqueous saline solution and aqueous dextrose and glycerol solution are used as a liquid carrier of an injectable solution. Suitable excipients include light anhydrous silicic acid, crystalline cellulose, mannitol, starch, glucose, lactose, sucrose, gelatin, malt, rice, wheat flour, chalk, silica gel, sodium stearate, glyceryl monostearate, talc, sodium chloride, powdered skim milk, glycerol, propylene, glycol, water, ethanol, carmellose calcium, carmellose sodium, hydroxypropyl cellulose, hydroxypropyl methylcellulose, polyvinyl acetal diethylamino acetate, polyvinylpyrrolidone, gelatin, medium-chain fatty acid triglyceride, polyoxyethylene hydrogenated castor oil 60, saccharose, carboxymethylcellulose, corn starch, inorganic salt and the like. When desired, the composition can contain a small amount of wetting agent or emulsifier or pH buffer. These compositions can be in a form of solution, suspension, emulsion, tablet, pill, capsule, powder, sustained release mixture or the like. It is also possible to use traditional binding agents and carriers, such as tryglyceride, to prepare a composition as a suppository. Oral preparation can also comprise a standard carrier such as medicine grade mannitol, lactose, starch, magnesium stearate, sodium saccharin, cellulose, or magnesium carbonate. Examples of a suitable carrier are described in E. W. Martin, Remington's Pharmaceutical Sciences (Mark Publishing Company, Easton, U.S.A). Such a composition contains a therapeutically effective amount of therapy agent and preferably in a purified form, together with a suitable amount of carrier, such that the composition is provided in a form suitable for administration to a patient. A preparation must be suitable for the administration format. In addition, the composition may comprise, for example, a surfactant, excipient, coloring agent, flavoring agent, preservative, stabilizer, buffer, suspension, isotonizing agent, binding agent, disintegrant, lubricant, fluidity improving agent, corrigent or the like.

When the present invention is administered as a medicament, various delivery systems are known, and such systems can be used to administer a therapeutic agent of the present invention to a suitable site (e.g., esophagus). Such a system, for example, can use a recombinant cell that can express encapsulated therapeutic agent (e.g., polypeptide) in liposomes, microparticles and microcapsules or use of endocytosis mediated by a receptor; construction of a therapy nucleic acid as a part of a retrovirus vector or other vector or the like. The method of introduction includes, but not limited to, intradermal, intramuscular, intraperitoneal, intravenous, subcutaneous, intranasal, epidural and or al pathways. A medicament can be administered by any suitable pathway, such as by injection, bolus injection, or by absorption through epithelial or mucocutaneous lining (e.g., or al cavity, rectum, intestinal mucosa or the like). In addition, an inhaler or mistifier using an aerosolizing agent can be used as needed. Moreover, other biological activating agents can also be administered together. Administration can be systemic or local. When the present invention is used in an ovarian region, a medicament may be administered through any suitable pathway such as direct injection into an affected site of an ovary or the like.

In a specific embodiment where a therapeutic agent is a nucleic acid, the nucleic acid can be constructed as a part of a suitable nucleic acid expression vector and administered in vivo to be present in a cell to promote expression of an encoded protein. This can be implemented, for example, by using a retrovirus vector, direct injection, use of a microparticle gun, coating the nucleic acid with lipid, cell surface receptor or transfection agent, or administering a nucleic acid linked to a tag sequence known to enter the nucleus. Alternatively, a nucleic acid therapeutic agent can be introduced in a cell such that it is incorporated into a host cell DNA by homologous recombination for expression.

In a preferred embodiment, a composition can be prepared as a pharmaceutical composition adapted to administration to humans in accordance with a known method. Such a composition can be administered by an injection. A composition for injection is typically a solution in an aseptic isotonic aqueous buffer. A composition can also comprise a local anesthetic such as lidocaine which alleviates the pain at the site of injection and a solubilizing agent as needed. Generally, ingredients can be supplied separately or by mixing the ingredients together in a unit dosing form and supplied, for example, in a sealed container such as an ampoule or sachet showing the amount of active agent or as a lyophilized powder or water-free concentrate. When a composition is to be administered by injection, the composition can be distributed by using an injection bottle containing aseptic agent-grade water or saline. When a composition is to be administered by injection, an aseptic water or saline ampoule for injection can also be provided such that the ingredients can be mixed prior to administration.

The composition, medicament, therapeutic agent, and prophylactic agent of the present invention can be prepared as a neutral or salt form or other prodrugs (e.g., ester or the like). Pharmaceutically acceptable salts include salts formed with a free carboxyl group, derived from hydrochloric acid, phosphoric acid, acetic acid, oxalic acid, tartaric acid or the like, salts formed with a free amine group, derived from isopropylamine, trimethylamine, 2-ethylaminoethanol, histidine, procaine or the like, and salts derived from sodium, potassium, ammonium, calcium, or ferric hydroxide or the like.

The amount of therapeutic agent of the present invention that is effective in therapy of a specific disorder or condition may vary depending on the properties of the disorder or condition. However, such an amount can be determined by those skilled in the art by a standard clinical technique based on the descriptions herein. Furthermore, an in vitro assay can be used in some cases to assist the identification of the optimal dosing range. The precise dose to be used in a preparation may also vary depending on the administration pathway or the severity of the disease or disorder. Thus, the dose should be determined in accordance with the judgment of the attending physician or the condition of each patient. The dosage is not particularly limited, but may be 0.001, 1, 5, 10, 15, 100 or 1000 mg/kg body weight per dosage or within a range between any two values described above. The dosing interval is not particularly limited, but may be, for example, 1 or 2 administration every 1, 7, 14, 21, or 28 days or 1 or 2 administrations in the range of period between any two values described above. The dosage, dosing interval, and dosing method may be appropriately selected depending on the age, weight, symptom, target organ or the like of the patient. Further, it is preferable that a therapeutic drug contains a therapeutically effective amount, or an amount effective for exerting a desired effect, of effective ingredients. When a malignant tumor marker significantly decreases after administration, the presence of a therapeutic effect may be acknowledged.

"Patient" in one embodiment of the present invention includes humans and mammals excluding humans (e.g., one or more types of mice, guinea pigs, hamsters, rats, rabbits, pigs, sheep, goats, cows, horses, cats, dogs, marmosets, monkeys and the like). Further, the patient may be a patient determined or diagnosed as having an episode of LSR positive malignant tumor. It is preferable that determination or diagnosis in this regard is performed by detecting the LSR protein level.

The pharmaceutical composition, therapeutic agent or prophylactic agent of the present invention can be provided as a kit.

In a specific embodiment, the present invention provides an agent pack or kit comprising one or more containers filled with one or more ingredients of the composition or medicament of the present invention. Optionally, information indicating approval for manufacture, use or sale for administration to a human by a government agency regulating the manufacture, use or sale of medicaments or biological products in a stipulated form can be appended to such a container.

The kit of the present invention can also contain an expression vector encoding a protein to be used as the composition, therapeutic agent, prophylactic agent or medicament of the present invention. Since such a protein, after expression, forms a biologically active complex, the protein may be reconstituted. Such a kit preferably contains a required buffer and a reagent. Optionally, instruction (package insert) for use of the kit and/or information indicating approval for manufacture, use or sale for administration to a human by a government agency regulating the manufacture, use or sale of medicaments or biological products in a stipulated form can be appended to such a container.

In a specific embodiment, the pharmaceutical composition comprising a nucleic acid of the present invention can be administered via liposomes, microparticles, or microcapsules. In various embodiments of the present invention, it may be useful to use such a composition to achieve sustained release of the nucleic acid.

One embodiment of the present invention may be an anti-LSR antibody, which is one or more antibodies selected from the group consisting of (a) an antibody comprising heavy chain CDRs 1, 2, and 3 and light chain CDRs 1, 2, and 3 with amino acid sequences set forth in positions 31-35, 50-66, 99-104, 153-165, 182-188 and 221-230 of SEQ ID NO: 1, respectively, (b) an antibody comprising heavy chain CDRs 1, 2, and 3 and light chain CDRs 1, 2, and 3 with amino acid sequences set forth in positions 31-35, 50-66, 99-103, 152-165, 182-188 and 221-230 of SEQ ID NO: 2, respectively, (c) an antibody comprising heavy chain CDRs 1, 2, and 3 and light chain CDRs 1, 2, and 3 with amino acid sequences set forth in positions 31-35, 50-66, 99-104, 153-165, 182-188 and 221-229 of SEQ ID NO: 3, respectively, (d) an antibody comprising heavy chain CDRs 1, 2, and 3 and light chain CDRs 1, 2, and 3 with amino acid sequences set forth in positions 31-35, 50-66, 99-104, 153-165, 182-188 and 221-229 of SEQ ID NO: 4, respectively, (e) an antibody comprising heavy chain CDRs 1, 2, and 3 and light chain CDRs 1, 2, and 3 with amino acid sequences set forth in positions 31-35, 50-66, 99-104, 153-165, 182-188 and 221-229 of SEQ ID NO: 5, respectively, and (f) an antibody comprising heavy chain CDRs 1, 2, and 3 and light chain CDRs 1, 2, and 3 with amino acid sequences set forth in positions 31-35, 50-66, 99-104, 153-165, 182-188 and 221-229 of SEQ ID NO: 6, respectively, or a mutant of the antibody, which is free of a mutation in the CDRs but comprises one or several substitutions, additions, or deletions in a framework of the antibody in the mutant. Use of such an anti-LSR antibody can effectively suppress especially the growth of LSR-positive malignant tumor cells. Further, LSR-positive malignant tumor can be efficiently diagnosed. Further, another embodiment of the present invention is an anti-LSR antibody comprising at least one of the sets of amino acid sequences of heavy chain CDRs 1, 2, and 3 listed above. These antibodies may be an antibody selected from a monoclonal antibody, polyclonal antibody, chimeric antibody, humanized antibody, human antibody, multifunctional antibody, bispecific or oligospecific antibody, single chain antibody, scFV, diabody, sc(Fv)$_2$ (single chain (Fv)$_2$), and scFv-Fc.

The anti-LSR antibody according to one embodiment of the present invention may comprise a set of amino acid sequences of heavy chain CDRs 1, 2, and 3 and light chain CDRs 1, 2, and 3, and at least one, preferably, 2, 3, 4, 5, 6, 7 or all of the heavy chain FRs 1, 2, 3, and 4 and light chain FRs 1, 2, 3, and 4 are identical, substantially identical, or identical except for a conservative substitution with any one of SEQ ID NOs: 1-6. The anti-LSR antibody may be one or more types of antibodies. Further, another embodiment of the present invention is an anti-LSR antibody comprising at least one of the amino acid sequence set of heavy chain FRs 1, 2, 3, and 4 listed above.

The anti-LSR antibody according to one embodiment of the present invention may be in a form of scFv. In such a case, a linker between a heavy chain and a light chain may have an amino acid sequence set forth in positions 116-132 of SEQ ID NO: 1, positions 116-132 of SEQ ID NO: 2, positions 116-132 of SEQ ID NO: 3, positions 116-132 of SEQ ID NO: 4, positions 116-132 of SEQ ID NO: 5, or positions 116-132 of SEQ ID NO: 6.

VHs of #9-7, #16-6, No. 26-2, No. 27-6, No. 1-25, and No. 1-43 described in Example 2 described below are positions 1-115 of SEQ ID NO: 1, positions 1-115 of SEQ ID NO: 2, positions 1-115 of SEQ ID NO: 3, positions 1-115 of SEQ ID NO: 4, positions 1-115 of SEQ ID NO: 5, and positions 1-115 of SEQ ID NO: 6, respectively. Further, VLs of #9-7, #16-6, No. 26-2, No. 27-6, No. 1-25, and No. 1-43 described in Example 2 described below are positions 133-238 of SEQ ID NO: 1, positions 133-239 of SEQ ID NO: 2, positions 133-238 of SEQ ID NO: 3, positions 133-238 of SEQ ID NO: 4, positions 133-238 of SEQ ID NO: 5, and positions 133-238 of SEQ ID NO: 6, respectively.

The amino acid sequences listed above may be one or more amino acid sequences selected from the group consisting of (i) the above-described amino acid sequence with one or several base sequence deletions, substitutions, insertions or additions, (ii) an amino acid sequence with 90% or greater homology to the above-described amino acid sequence, and (iii) an amino acid sequence encoded by a polynucleotide that hybridizes specifically to a polynucleotide consisting of abase sequence complementary to a base sequence encoding the above-described amino acid under stringent conditions, as long as an anti-LSR antibody has a desired effect.

A vector or polynucleotide encoding the anti-LSR antibody according to one embodiment of the present invention can be introduced into a cell to produce a transformant. Such a transformant can be used to make the anti-LSR antibody according to the embodiment of the present invention. The transformant may be a cell of a human or a mammal excluding humans (e.g., rat, mouse, guinea pig, rabbit, cow, monkey or the like). Examples of a mammalian cell include Chinese hamster ovary cells (CHO cells), monkey cells COS-7 and the like. Further, the tranformant may be *Escherichia* bacteria, yeasts or the like.

For example, an *E. coli* derived plasmid (e.g., pET-Blue), a *Bacillus subtilis* derived plasmid (e.g., pUB110), a yeast derived plasmid (e.g. pSH19), an animal cell expression plasmid (e.g., pA1-11, pdDNA3.1-V5/His-TOPO), bacteriophage such as A phage, a virus-derived vector or the like can be used as the above-described vector. Such vectors may comprise a constituent element required for protein expression such as a promotor, origin of replication, or antibiotic resistant gene. The vector may be an expression gene.

Examples of method of introducing the above-described polynucleotide or vector into cells that can be used include calcium phosphate method, lipofection, electroporation, method using adenovirus, method using a retrovirus, and microinjection (Revised 4th edition Shin Idenshikogaku Handobukku [*New Genetic Engineering Handbook*], Yodosha (2003): 152-179). Examples of a method of producing an antibody using a cell that can be used include the methods described in "Tanpakushitsu Jikken Handobukku [*Protein experiment handbook*], Yodosha (2003): 128-142". Purification of antibodies can use, for example, ammonium sulfate, ethanol precipitation, protein A, protein G, gel filtration chromatography, anion, cation exchange chromatography, phosphocellulose chromatography, hydrophobic interaction chromatography, affinity chromatography, hydroxyapatite chromatography, lectin chromatography or the like "Tanpakushitsu Jikken Handobukku [*Protein experiment handbook*], Yodosha (2003): 27-52".

To implement the present invention, a nucleic acid can be selected as the suppressantin a nucleic acid form of the present invention by using antisense activity as an indicator. In this regard, "antisense activity" refers to activity that can specifically suppress or decrease expression of a target gene. More specifically, antisense activity refers to activity that can decrease the amount of protein expression, depending on the nucleotide sequence introduced into cells, by specifically reducing the amount of mRNA of a gene having a nucleotide sequence region complementary to such a sequence. The approach thereof is roughly classified into a method of introducing an RNA molecule complementary to mRNA made from a target gene directly into cells, and a method of introducing a construct vector that can express an RNA complementary to a gene of interest into cells.

Antisense activity is achieved by a nucleic acid sequence with a length of at least 8 contiguous nucleotides, which is complementary to a nucleic acid sequence of a gene of interest. Such a nucleic acid sequence may be a nucleic acid sequence preferably with a length of at least 9 contiguous nucleotides, more preferably with a length of 10 contiguous nucleotides, and still more preferably with a length of 11 contiguous nucleotides, a length of 12 contiguous nucleotides, a length of 13 contiguous nucleotides, a length of 14 contiguous nucleotides, a length of 15 contiguous nucleotides, a length of 16 contiguous nucleotides, a length of 17 contiguous nucleotides, a length of 18 contiguous nucleotides, a length of 19 contiguous nucleotides, a length of 20 contiguous nucleotides, a length of 21 contiguous nucleotides, a length of 22 contiguous nucleotides, a length of 23 contiguous nucleotides, a length of 24 contiguous nucleotides, a length of 25 contiguous nucleotides, a length of 30 contiguous nucleotides, a length of 40 contiguous nucleotides, or a length of 50 contiguous nucleotides. Such a nucleic acid sequence includes nucleic acid sequences that are at least 70% homologous, more preferably at least 80% homologous, still more preferably 90% homologous or 95% homologous to the aforementioned sequences. Such antisense activity is preferably complementary to a sequence at the 5' terminus of a nucleic acid sequence of a gene of interest. Such an antisense nucleic acid sequence includes the aforementioned sequences with one or several or one or more nucleotide substitutions, additions, and/or deletions. Thus, antisense activity as used herein includes, but is not limited to, decrease in the amount of gene expression.

Common antisense techniques are described in text books (Murray, J A H eds., Antisense RNA and DNA, Wiley-Liss Inc, 1992). Furthermore, the latest research has elucidated a phenomenon called RNA interference (RNAi), leading to development of antisense techniques.

As used herein, "RNAi" is an abbreviation of "RNA interference" and is commonly known in the art. RNA interference is a biological process that inhibits or down-regulates gene expression in cells, mediated by an agent inducing RNAi. For example, RNA interference refers to a phenomenon of specific degradation of homologous mRNA to suppress the synthesis of gene products by introducing into a cell an agent inducing RNAi, such as a double stranded RNA (also called dsRNA), or a technique used therein. As used herein, "RNAi" may in some cases be used synonymously with "agent inducing RNAi", "agent causing RNAi", "RNAi agent" or the like. For RNAi, see, for example, Zamore and Haley, 2005, Science, 309, 1519-1524; Vaughn and Martienssen, 2005, Science 309, 1525-1526; Zamore et al., 2000, Cell, 101, 25-33; Bass, 2001, Nature, 411, 428-429; Elbashir et al., 2001, Nature, 411, 494-498; and Kreutzer et al, International Publication No. WO00/44895; Zernicka-Goetz et al, International Publication No. WO 01/36646; Fire, International Publication No. WO 99/32619; Plaetinck, et al., International Publication No. WO 00/01846; Mello and Fire, International Publication No. WO 01/29058; Deschamps-Depaillette, International Publication No. WO 99/07409 and Li et al., International Publication No. WO 00/44914; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237; Hutvagner and Zamore, 2002, Science, 297, 2056-60; McManus et al., 2002, RNA, 8, 842-850; Reinhart et al., 2002, Gene & Dev., 16, 1616-1626; and Reinhart & Bartel, 2002, Science, 297, 1831. Further, it is understood that the term RNAi as used herein represents a synonym of other terms used to describe sequence specific RNA interference such as post-transcription gene silencing, inhibition of translation, inhibition of transcription, or epigenetics. As used herein, "agent causing RNAi" may be any agent as long as "RNAi" is caused.

Examples of "agent causing RNAi" as used herein include "small interfering nucleic acid" "siNA", "small interfering RNA", "siRNA", "small interfering nucleic acid molecule", "small oligonucleotide molecule", "chemically modified small interfering nucleic acid molecule" and the like. These terms refer to any nucleic acid molecule that can inhibit or downregulate gene expression or virus replication by sequence specifically mediating RNA interference "RNAi" or gene silencing. These terms may represent an individual nucleic acid molecule, multiple such nucleic acid molecules, or a pool of such nucleic acid molecules. The molecules may be a double stranded nucleic acid molecule comprising a self-complementary sense region and an antisense region.

"SiRNA" that is typically used in the present invention is a doubled stranded RNA that is short with a length of generally about 20 bases (e.g., typically about 21-23 bases long) or less. Such an siRNA, when expressed in cells, suppresses gene expression and suppresses expression of a target pathogenic gene of the siRNA. Thus, such an siRNA can be used in therapy, prevention, prognosis or the like of a disease. The siRNA used in the present invention may be in any form, as long as it is capable of inducing RNAi.

In the present invention, an antisense region in an agent causing RNAi such as an siRNA comprises a sense region having a nucleotide sequence which is complementary to a nucleotide sequence in a target nucleic acid molecule or a portion thereof and a nucleotide sequence corresponding to the target nucleic acid sequence or a portion thereof. These molecules can be assembled from two separate oligonucleotides, one being a sense strand and the other being an antisense strand. The antisense strand and sense strand in this regard are self-complementary (i.e., each strand comprises a nucleotide sequence that is complementary to the nucleotide sequence in the other strand, e.g., the antisense strand and the sense strand form a double strand or double stranded structure). A double stranded region in this regard can be, for example, about 15 to about 30 base pairs such as about 15, 16, 17, 18, 19, 20, 21, 22, 23, 24, 25, 26, 27, 28, 29 or 30 base pairs or longer. The antisense strand comprises a nucleotide sequence that is complementary to a nucleotide sequence in a target nucleic acid molecule or a portion thereof, and the sense strand comprises a nucleotide sequence corresponding to the target nucleic acid sequence or a portion thereof (e.g., about 15-25 or more nucleotides of the molecule are complementary to a target nucleic acid or a portion thereof). Alternatively, these molecules are assembled from a single oligonucleotide, and the self-complementary sense region and antisense region of these molecules are linked by a nucleic acid linker or a non-nucleic acid linker. These molecules can be polynucleotides having a double stranded, asymmetrical double stranded, hairpin, or asymmetrical hairpin secondary structure comprising a self-complementary sense region and antisense region. The antisense region in this regard comprises a separate sense region having a nucleotide sequence which is complementary to a nucleotide sequence in a target nucleic acid molecule or a portion thereof and a nucleotide sequence corresponding to the target nucleic acid sequence or a portion thereof. These molecules may be a cyclic single stranded polynucleotide having two or more loop structures and a stem comprising a self-complementary sense region and antisense region. The antisense region in this regard comprises a separate sense region having a nucleotide sequence which is complementary to a nucleotide sequence in a target nucleic acid molecule or a portion thereof and a nucleotide sequence corresponding to the target nucleic acid sequence or a portion thereof. In addition, acyclic polynucleotide can be processed in vivo or in vitro to generate an active molecule that can mediate RNAi. These agents may also comprise a single stranded polynucleotide having a nucleotide sequence, which is complementary to a nucleotide sequence in a target nucleic acid molecule or a portion thereof (for instance, for these agents, a nucleotide sequence corresponding to the target nucleic acid molecule or a portion thereof does not need to be present in these agents). A single stranded polynucleotide may further comprise a terminal phosphoric acid group such as 5' phosphoric acid (for example, see Martinez et Al., 2002, Cell., 110, 563-574 and Schwarz et al., 2002, Molecular Cell, 10, 537-568) or 5', 3'-diphosphoric acid. In a certain embodiment, the LSR suppressant of the present invention comprises separate sense and antisense sequences or regions. The sense region and antisense region in this regard are covalently attached by a nucleotide or non-nucleotide linker molecule known in the art, or non-covalently attached to each other by ionic interaction, hydrogen bond, Van der Waal's interaction, hydrophobic interaction and/or stacking interaction. In a certain embodiment, the LSR suppressant of the present invention comprises a nucleotide sequence that is complementary to a nucleotide sequence of a target gene. In another embodiment, the LSR suppressant of the present invention interacts with a nucleotide sequence of a target gene such that expression of the target gene is inhibited. The LSR suppressantis not necessarily limited herein to molecules comprising only an RNA. The LSR suppressant also encompasses chemically modified nucleotides and non-nucleotides. In a certain embodiment, when the present invention is a small interfering nucleic acid molecule, a 2' hydroxy (2'-OH) containing nucleotide may be lacking. In a certain embodiment, the present invention can be a small interfering nucleic acid, which does not require the presence of a nucleotide having a 2' hydroxyl group for mediating RNAi. Thus, when the present invention is a small interfering nucleic acid molecule, ribonucleotide (e.g., nucleotide having a 2'-OH group) does not need to be included. However, when the presence of a ribonucleotide in an LSR suppressantis not required for maintaining RNAi, it may have a bound linker, or another bound or conjugated group, moiety or strand comprising one or more nucleotides having a 2'-OH group. Optionally, an agent suppressing LSRs of the present invention may comprise a ribonucleotide in about 5, 10, 20, 30, 40 or 50% of the nucleotide positions. Herein, the LSR suppressant may be a nucleic acid molecule that can mediate sequence specific RNAi, such as small interfering RNA (siRNA), double stranded RNA (dsRNA), microRNA (miRNA), short hairpin RNA (shRNA), small interfering oligonucleotide, small interfering nucleic acid, small interfering modified oligonucleotide, chemically modified siRNA, or post-transcriptional gene silencing RNA.

Examples of agents inducing RNAi herein include, but are not limited to, RNAs comprising a double stranded moiety with a length of at least 10 nucleotides, comprising a sequence having at least about 70% homology or a sequence that hybridizes under stringent conditions to a portion of a nucleic acid sequence of a target gene and variants thereof. The agent in this regard can preferably comprise a 3' overhang, and more preferably the 3' overhang is a DNA with a length of 2 nucleotides or longer (e.g., DNA with a length of 2-4 nucleotides).

Alternatively, examples of RNAi used in the present invention include, but are not limited to, a pair of short complementary sequences in the opposite direction (e.g., 15 bp or longer such as 24 bp or the like).

Although not wishing to be bound by any theory, as one conceivable working mechanism of RNAi, when a molecule inducing RNAi such as dsRNA is introduced into cells for a relatively long (e.g., 40 base pairs or greater) RNA, an RNase III-like nuclease called a dicer having a helicase domain cuts out the molecule into about 20 base pair each from the 3' terminus in the presence of ATP to produce short dsRNA (also called siRNA). As used herein, "siRNA" is an abbreviation for short interfering RNA and refers to a short double stranded RNA with 10 base pairs or more prepared by artificial chemical synthesis or biochemical synthesis, synthesis in the body of an organism, or degradation of a double stranded RNA with about 40 bases or more in vivo. An siRNA generally has a 5'-phosphoric acid or 3'-OH structure, and the 3' terminus overhangs by about 2 bases. A specific protein binds to the siRNA to form an RISC (RNA-induced-silencing-complex). Such a complex recognizes and binds to an mRNA having the same sequence as the siRNA and cleaves the mRNA in the middle portion of the siRNA by RNase III-like enzymatic activity. The relationship of the siRNA sequence and mRNA sequence to be cleaved as a target is preferably a 100% match. However, for a mutation of a base at a position away from the middle of the siRNA, cleaving activity due to RNAi would not be completely lost, but instead partially remains. On the other hand, a mutation of a base in the middle portion of the siRNA has a significant effect, such that mRNA cleaving activity due to RNAi is dramatically reduced. For mRNAs with a mutation, such a property can be utilized to degrade only mRNAs comprising a specific mutation by synthesizing an siRNA with the mutation positioned in the middle and introducing the siRNA into cells. Thus, the present invention can use an siRNA itself as an agent inducing RNAi or an agent that would produce an siRNA (e.g., typically a dsRNA with about 40 or more bases) as such an agent.

Although not wishing to be bound by any theory, it is intended for siRNAs that, aside from the above-described pathway, an antisense strand of the siRNA binds to an mRNA and acts as a primer of an RNA-dependent RNA polymerase (RdRP), such that a dsRNA is synthesized and the dsRNA is used again as a substrate of a dicer to produce a new siRNA and amplify the action. Thus, the siRNA itself and agents producing an siRNA are also useful in the present invention. In fact, for example, 35 dsRNA molecules nearly completely degrade 1000 or more mRNA copies in cells in insects or the like. Thus, it is understood that the siRNA itself and agents producing an siRNA are also useful.

In another embodiment, the agent inducing RNAi of the present invention can be a short hairpin structure (shRNA; short hairpin RNA) having an overhang at the 3' terminus. As used herein, "shRNA" refers to a molecule with about 20 or more base pairs, which comprises a partially palindrome-like base sequence in a single stranded RNA to be in a double stranded structure in a molecule to have a hairpin-like structure. Such an shRNA is artificially made by chemical synthesis. Alternatively, such an shRNA can be produced by synthesizing a hairpin structure DNA comprising DNA sequences of sense and antisense strands linked in opposite directions in vitro into an RNA with a T7RNA polymerase. Although not wishing to be bound by any theory, it should be understood that such an shRNA, after introduction into cells, is degraded into a length of about 20 bases (typically, for example, 21 bases, 22 bases or 23 bases) in the cells and induces RNAi as in an siRNA, resulting in a treatment effect of the present invention. It should be understood that such an effect is exerted in a wide range of organisms such as insects, plants and animals (including mammals). Since an shRNA induces RNAi as in siRNAs in this manner, it can be used as an effective ingredient of the present invention. Further, an shRNA preferably can have a 3' overhang. The length of a double stranded moiety is not particularly limited, but the length can be preferably about 10 nucleotides long or longer and more preferably about 20 nucleotides long or longer. The 3' overhang in this regard can be preferably a DNA, more preferably a DNA with a length of at least two nucleotides or more, and still more preferably a DNA with a length of 2-4 nucleotides. The agent inducing RNAi used in the present invention can be artificially synthesized (e.g., chemically or biochemically) or naturally occurring. There is no fundamental difference in the effect of the present invention therebetween. A chemically synthesized agent is preferably purified by liquid chromatography or the like.

The agent inducing RNAi used in the present invention can also be synthesized in vitro. In such a synthesis system, a T7RNA polymerase and T7 promoter are used to synthesize antisense and sense RNAs from a template DNA. After annealing is performed thereon in vitro, RNAi is induced through the aforementioned mechanism when cells are introduced to achieve the effect of the present invention. In this regard, such an RNA can be introduced into cells, for example, by any suitable method such as the calcium phosphate method. Examples of the agents inducing RNAi of the present invention include agents such as a single strand that can hybridize with an mRNA or all similar nucleic acid analogs thereof. Such agents are also useful in the present invention.

One embodiment of the present invention is a therapeutic drug for LSR positive malignant tumor comprising an RNAi molecule directed to LSRs or a polynucleotide encoding the RNAi molecule. Growth of LSR positive malignant tumor cells can be suppressed when such an RNAi molecule or polynucleotide encoding the RNAi molecule is used. "Polynucleotide" in one embodiment of the present invention may be a polymeric compound having 10 or more nucleotides, comprising a nucleotide polymerized in a straight chain.

"RNAi molecule" in one embodiment of the present invention is an RNA strand having RNAi action. Examples thereof include siRNA, shRNA, miRNA, small RNA having RNAi action and the like.

"RNAi" in one embodiment of the present invention includes a phenomenon of suppressing or silencing a function of a target gene, mRNA or the like by one or more of siRNA, shRNA, miRNA, single or double stranded RNA with a short or long chain, modified products thereof and the like.

For example, siDirect 2.0 (Naito et al., BMC Bioinformatics. 2009 Nov. 30; 10: 392.) or the like can be used to design an RNAi molecule. Further, designing can be commissioned to a specialist company (e.g., Takara Bio Inc. or the like). RNAi action can be verified by quantification of the amount of RNA strand expression by real-time RT-PCR. RNAi action can also be confirmed by analysis of the amount of RNA strand expression by Northern blot or a method of analyzing the amount of protein and observing the phenotype or the like by Western blot. Further, a plasmid producing siRNAs or shRNAs for a specific gene can be purchased, for example, from a specialist company (e.g., Takara Bio Inc. or the like).

"SiRNA" in one embodiment of the present invention comprises an RNA strand capable of inducing RNAi. Two strands of an siRNA can generally be separated into a guide strand and a passenger strand, where the guide strand in incorporated into an RISC. The guide strand incorporated into the RISC is used to recognize a target RNA. Although an artificially created guide strand is mainly used in RNAi research, those endogenous in a living body are also known. The above-described guide chain may be composed of an RNA with 15 bases or more. When there are 15 bases or more, the possibility of being able to precisely bind to a target nucleotide increases. Further, the guide strand may be composed of an RNA with 40 bases or less. With 40 bases or less, the risk of a disadvantageous phenomenon such as interferon response occurring is further reduced.

"shRNA" in one embodiment of the present invention comprises a single strand of RNA strand that can induce RNAi and form a structure folded into a hairpin shape (hairpin-like structure). Typically, an shRNA is cleaved by a dicer in a cell to cut out an siRNA. It is known that a target RNA is cleaved by the siRNA. The above-described shRNA may be composed of 35 or more nucleotides. With 35 or more, the possibility of being able to precisely form a hairpin-like structure unique to shRNAs increases. Further, the above-described shRNA may be composed of an RNA with 100 bases or less. With 100 bases or less, the risk of a disadvantageous phenomenon such as interferon response occurring is reduced. However, many of the pre-miRNAs that generally have a similar structure and function as shRNAs have a length of about 100 nucleotides or more. Thus, it is conceivable that they can function as a shRNA even when the length of the shRNA is not necessarily 100 bases or less.

It is known that "miRNA" in one embodiment of the present invention comprises an RNA strand having a function similar to an siRNA and suppresses translation of, and degrades, a target RNA strand. The difference in miRNAs and siRNAs is generally in the production pathway and the detailed mechanism.

"Small RNA" in one embodiment of the present invention refers to a relatively small RNA strand. Examples thereof include siRNAs, shRNAs, miRNAs, antisense RNAs, small RNAs with one or two strands and the like.

The RNAi molecules may comprise an overhang consisting of 1-5 bases at the 5' terminus or the 3' terminus. It is understood that RNAi efficiency is enhanced in such a case. The number of bases may be, for example, 5, 4, 3, 2, or 1, or within a range of any two values described above. When the above-described RNAi molecule is double stranded, a mismatching RNAs may be present between each RNA strand. The number of mismatching RNAs may be, for example, 1, 2, 3, 4, 5, or 10 or less, or within the range of any two values described above. Further, the above-described RNAi molecule may comprise a hairpin loop. The number of bases of a hairpin loop may be, for example, 10, 8, 6, 5, 4, or 3 or within any two values described above. The base sequence may have one or a plurality of base sequence deletions, substitutions, insertions or additions, as long as the sequence has a desired effect. The left side of each base sequence is denoted as the 5' terminus and the right side as the 3' terminus.

The length of the above-described RNAi molecule may be, for example, 15, 18, 20, 25, 30, 40, 50, 60, 80, 100, 200, or 400 bases or within a range between any two values described above. The number is preferably 15 or more or 100 or less from the viewpoint of improving the therapeutic effect on LSR positive malignant tumor.

"RNA strand" in one embodiment of the present invention includes those constituted in a form in which a plurality of RNAs or equivalents thereof are bound. "DNA strand" in one embodiment of the present invention includes those constituted in a form in which a plurality of DNAs or equivalents thereof are bound. The RNA strand or DNA strand includes RNA strands or DNA strands in a single stranded or multi-stranded (e.g., double stranded) form. The RNA strand or DNA strand may be bound to a substance promoting incorporation into cells (e.g., PEG or derivative thereof), labeling tag (e.g., fluorescent labeling tag or the like), a linker (e.g., nucleotide linker or the like) or the like. The RNA strand or DNA strand can be synthesized by using a nucleic acid synthesizer or purchased from a specialist company (e.g., Invitrogen or the like). An RNA strand or DNA strand in a living body may form a salt or a solvate. Further, an RNA strand or DNA strand in a living body may be chemically modified. The term RNA strand or DNA strand includes, for example, RNA strands or DNA strands forming a salt or solvate, RNA strands or DNA strands subjected to chemical modification, and the like. Further, an RNA strand or DNA strand may be an analog of the RNA strand or an analog of the DNA strand.

Examples of "salt" in one embodiment of the present invention include anionic salts formed with any acidic (e.g., carboxyl) group and cationic salts formed with any basic (e.g., amino) group. Salts include inorganic salts and organic salts, as well as salts described in, for example, Berge et al., J. Pharm. Sci., 1977, 66, 1-19. Further examples include metal salts, ammonium salts, salts with organic base, salts with inorganic acid, salts with organic acid and the like. "Solvent" in one embodiment of the present invention is a compound formed with a solute or solvent. For example, J. Honig et al., The Van Nostrand Chemist's Dictionary P650 (1953) can be referred for solvates. When a solvent is water, a solvate formed is a hydrate. It is preferable that the solvent does not obstruct the biological activity of the solute. Examples of such a preferred solvent include, but not particularly limited to water and various buffers. Examples of "chemical modification" in one embodiment of the present invention include modification with PEG or a derivative thereof, fluorescein modification, biotin modification and the like.

The above-described RNAi molecule preferably comprises a base sequence that is complementary to a port ion of abase sequence of an LSR mRNA from the viewpoint of stably exerting RNAi action. The above-described "portion" may be, for example, 5, 10, 15, 18, 20, 22, 24, 26, 28, 30, 35, 40 or 50 bases or more or within a range of any two values described above.

The siRNA used in Example 3 described below comprises the base sequence of SEQ ID NO: 9 or 10. These base sequences are considered to be base sequences complementary to a portion of an LSR mRNA and responsible for the function as a guide strand. One embodiment of the present invention comprises an RNAi molecule comprising such the base sequence of SEQ ID NO: 9 or 10. The RNAi molecule may further comprise a base sequence complementary to the base sequence set forth in SEQ ID NO: 9 or 10 (e.g., SEQ ID NO: 11 or 12, respectively). "Complementary base sequence" in one embodiment of the present invention is abase sequence having a polynucleotide with high complementarity capable of hybridizing to another polypeptide. The full length sense strand of the siRNA used in Example 3 described below is the base sequence of SEQ ID NO: 13 or 14, and the full length antisense strand is the base sequence of SEQ ID NO: 15 or 16.

As long as an LSR siRNA has a desired effect, the base sequences listed above may be (i) an amino acid sequence with one or several base sequence deletions, substitutions, insertions or additions in the above-described base acid sequence, or (ii) abase sequence encoded by a polynucleotide that specifically hybridizes with a polynucleotide consisting of a base sequence complementary to the above-described base sequence under stringent conditions.

One embodiment of the present invention is a therapeutic drug for LSR positive malignant tumor, comprising an LSR antagonist. The LSR antagonist comprises a substance inhibiting the expression or function of an LSR. The growth of LSR positive malignant tumor cells can be suppressed by using such an LSR antagonist. The form of antagonist is not particularly limited as long as it has an action of inhibiting the expression or function of an LSR. For example, the antagonist may be in a form of an antibody, RNA strand, DNA strand, low molecular weight organic compound, or polypeptide. The above-described RNA strand may be an RNAi molecule directed to an LSR. A DNA strand encoding an RNAi molecule directed to an LSR can be used as the above-described DNA strand. For example, the DNA strand may be in a form of a vector.

Examples of "inhibit the expression of a protein" in one embodiment of the present invention include inhibiting the transcription mechanism from a gene to an mRNA or inhibiting the translation mechanism from an mRNA to a protein. Examples further include inducing degradation of a gene, mRNA or protein to ultimately decrease the amount of protein. "Inhibit a function of protein" in one embodiment of the present invention includes causing a structural change in a protein to reduce the activity of the protein. Examples thereof further include inhibiting the expression of a gene, resulting in reduction in the amount of mRNA or protein production.

"State where expression is inhibited" in one embodiment of the present invention includes a state of significantly decreased amount of expression relative to normal levels. The amount of mRNA or protein may be used as an indicator for the amount of expression. "Significantly" in one embodiment of the present invention may be, for example, a state where there is a statistically significant difference, when assessed by Student's t-test (one or two tailed), at $p<0.05$. Further, a state where a substantial difference has occurred is also included. "State where a function is inhibited" in one embodiment of the present invention includes a state with significantly decreased activity relative to normal levels.

One embodiment of the present invention is a novel method of therapy for malignant tumor. Such a therapeutic method comprises, for example, a step of administering an anti-LSR antibody to a patient. LSR positive malignant tumor can be treated by using such a therapeutic method. Further, such a therapeutic method is excellent from the viewpoint of safety, as the method uses antibodies.

There are LSR positive and LSR non-positive patients among malignant tumor patients. For this reason, the above-described therapeutic method is preferably administered to a malignant tumor patient determined to have malignant tumor that is LSR positive malignant tumor. In this manner, diagnosis for the presence or absence of an LSR positive condition in advance enables a more optimal dosing.

Thus, the above-described therapeutic method for malignant tumor preferably comprises a step of diagnosing whether a patient has an episode of LSR positive malignant tumor from the viewpoint of administering a more optimal dosing. Further, the therapeutic method may comprise a step of investigating whether malignant tumor cells derived from a patient express LSRs. An episode of LSR positive malignant tumor may be diagnosed, for example, by diagnosing mRNA expression or protein expression. The diagnosis is preferably conducted by diagnosis of protein expression from the viewpoint of accurately diagnosing LSR positive to realize a more optimal dosing. Protein expression may be diagnosed by using, for example, an anti-LSR antibody. In diagnosis of an episode, an episode of LSR positive malignant tumor may be determined to be present when a protein obtained from malignant tumor cells to be tested derived from a patient is subjected to Western blot and a band corresponding to LSRs can be confirmed by visual inspection. Further, an episode of LSR positive malignant tumor may be determined to be present when the amount of LSR expression of malignant tumor cells derived from a patient is significantly larger relative to normal cells or LSR negative malignant tumor cells. Further, an episode of LSR positive malignant tumor may be determined to be present when total protein obtained from malignant tumor cells derived from a patient and total protein obtained from normal cells or LSR negative malignant tumor cells are subjected to Western blot and the malignant tumor cells derived from the patient have a significantly stronger band intensity corresponding to LSRs relative to the normal cells or LSR negative malignant tumor cells. Further, an episode of LSR positive malignant tumor may be determined to be present when serum or plasma obtained from malignant tumor patients and serum or plasma obtained form healthy individuals or LSR negative malignant tumor patients are subjected to ELISA using anti-LSR antibodies and the amount of LSR expression is significantly more for the serum or plasma derived from malignant tumor patients relative to healthy individuals or LSR negative malignant tumor patients. The serum or plasma sample itself may be quantified, or exosomes may be isolated from the serum or plasma to subject LSRs in the exosomes to ELISA for analysis. RT-PCR may be used instead of Western blot in such diagnosis for an episode of LSR positive malignant tumor.

The therapeutic method of malignant tumor according to one embodiment of the present invention may comprise a step of administering an LSR antagonist to a patient. Further, the method may comprise a step of administering an RNAi molecule directed to an LSR or a polynucleotide encoding the RNAi molecule to the patient.

One embodiment of the present invention is a novel diagnostic drug for malignant tumor, comprising an anti-LSR antibody. The diagnostic drug may be, for example, a companion diagnostic drug for malignant tumor therapy targeting LSRs, comprising an anti-LSR antibody. Since there are LSR positive and LSR non-positive patients among malignant tumor patients, therapeutic efficacy of the malignant tumor therapy targeting LSRs can be diagnosed if the companion diagnostic drug is used to inspect in advance whether malignant tumor is LSR positive. In such diagnosis, when the result is LSR positive, malignant tumor therapy targeting LSRs can be determined to be effective. "Companion diagnosis" in one embodiment of the present invention comprises diagnosis implemented in order to assist in the optimal dosing by predicting individual differences in the effect of agent or side effects for patients by inspection. For clinical application of an antibody medicament with anti-LSR antibodies, it is understood that selective therapy for LSR expressing-malignant tumor patients would lead to individualized medicine. For this reason, a method of sorting out an LSR positive patient is needed. An approach that inspects LSRs in a biopsy tissue of cancer by an immunohistochemical staining method is considered highly useful as a method of sorting out an LSR positive patient. However, obtaining a biopsy tissue is highly invasive. Thus, a method with a low level of invasiveness is preferred. Furthermore, certain types of malignant tumor such as ovarian cancer are problematic in that biopsy tissue is difficult to obtain due to the issues related to the site of cancer. In contrast, LSRs expressed in cancer or the extracellular domain thereof may be freely present in blood. In this regard, the possibility of high level of LSR expression in ovarian cancer tissue in a patient with a high blood LSR concentration is suggested when LSRs in the blood of a malignant tumor patient can be quantified. A blood sample is more advantageous than biopsy in that the level of invasiveness is low. It is highly likely that LSR is highly expressed in patient tissue with elevated blood LSR concentration relative to healthy individuals after quantifying the blood LSR concentration by ELISA. Thus, measurement of blood LSR concentration is considered highly useful as a companion diagnostic drug.

A diagnostic drug for malignant tumor according to one embodiment of the present invention may be a diagnostic drug comprising an anti-LSR antibody for diagnosis of therapeutic efficacy of the anti-LSR antibody or LSR antagonist on malignant tumor. Since there are LSR positive and LSR non-positive patients among malignant tumor patients, it is possible to diagnose the therapeutic efficacy of an anti-LSR antibody or LSR antagonist to patients if the diagnostic agent is used in advance to inspect whether malignant tumor is LSR positive.

One embodiment of the present invention is a companion diagnostic method for malignant tumor therapy targeting an LSR, comprising inspecting whether a malignant tumor sample of a malignant tumor patient is LSR positive. Since there are LSR positive and LSR non-positive patients among malignant tumor patients, it is possible to diagnose the therapeutic efficacy of malignant tumor therapy targeting an LSR if the companion diagnosis method is used to inspect in advance whether malignant tumor is LSR positive. Such a diagnostic method may further comprise a step of isolating or extracting a malignant tumor sample of a malignant tumor patient. "Malignant tumor sample" in one embodiment of the present invention may be malignant tumor tissue or cells obtained from a malignant tumor patient.

One embodiment of the present invention is a method of diagnosing prognosis of malignant tumor using an LSR expression level as an indicator. High level of LSR expression is demonstrated to be a poor prognosis marker (FIG. 38). Thus, a high level of LSR expression can be considered a poor prognosis marker. In one embodiment, cancer subjected to prognosis is ovarian serous adenocarcinoma, but the cancer is not limited thereto. It is understood that the present invention can be applied to ovarian clear cell adenocarcinoma and the like. It is also understood that the present invention can be applied to any other LSR positive malignant tumor. A method of using such a (poor) prognosis marker may comprise, for example, a step of investigating whether LSRs are expressed in malignant tumor cells derived from a patient. The prognosis (diagnosis) of LSR positive malignant tumor may be conducted, for example, by diagnosis or detection of mRNA expression or diagnosis or detection of protein expression. Such diagnosis or detection is preferably conducted by diagnosis of protein expression from the viewpoint of accurately diagnosing LSR positive to realize a more optimal dosing. Protein expression may be diagnosed by using, for example, an anti-LSR antibody. In diagnosis of an episode, the prognosis of malignant tumor may be determined to be poor when a protein obtained from malignant tumor cells to be tested derived from a patient is subjected to Western blot and enhancement in a band corresponding to LSRs can be confirmed by visual inspection. Further, the prognosis of malignant tumor may be determined to be poor when the amount of LSR expression of malignant tumor cells derived from a patient is significantly larger relative to normal cells or LSR negative malignant tumor cells (e.g., LSR negative cell strains such as OVTOKO). Further, the prognosis of malignant tumor may be determined to be poor when total protein obtained from malignant tumor cells derived from a patient and total protein obtained from normal cells or LSR negative malignant tumor cells (e.g., LSR negative cell strains such as OVTOKO) are subjected to Western blot and the malignant tumor cells derived from the patient have a significantly stronger band intensity corresponding to LSRs relative to the normal cells or LSR negative malignant tumor cells (e.g., LSR negative cell strains such as OVTOKO). Further, the prognosis of malignant tumor may be determined to be poor when serum or plasma obtained from malignant tumor patients and serum or plasma obtained form healthy individuals or LSR negative malignant tumor patients (e.g., "patient whose LSR expression is negative in ovarian cancer tissue") are subjected to ELISA using anti-LSR antibodies and the amount of LSR expression is significantly more for the serum or plasma derived from malignant tumor patients relative to the healthy individuals or LSR negative malignant tumor patients. The serum or plasma sample itself may be quantified, or exosomes may be isolated from the serum or plasma to subject LSRs in the exosomes to ELISA for analysis. RT-PCR may be used instead of Western blot in such diagnosis of an episode of LSR positive malignant tumor.

One embodiment of the present invention is a method of inspecting therapeutic efficacy of an anti-LSR antibody or LSR antagonist on malignant tumor. The inspection method comprises, for example, inspecting whether a malignant tumor sample of a malignant tumor patient is LSR positive. The inspection method, which may comprise a step of detecting the presence of LSRs in a malignant tumor sample, may comprise a step of detecting that the amount of LSRs in the malignant tumor sample is significantly larger relative to normal cells or LSR negative malignant tumor cells. For example, RT-PCR, Westernblot, or immunohistochemical staining method may be used in detecting LSRs. The standard of assessing the presence or absence of LSRs may be the same as that in the aforementioned diagnosis of episode of LSR positive malignant tumor. A method of inspecting therapeutic efficacy includes a method of inspecting whether the method is effective for therapy.

One embodiment of the present invention is a suppressant for growth of malignant tumor cells, comprising anti-LSR antibodies. Further, it is a method of suppressing growth of malignant tumor cells, comprising contacting anti-LSR antibodies with malignant tumor cells. Further, it is a suppressant for growth of malignant tumor cells, comprising an LSR antagonist. Further, it is a method of suppressing growth of malignant tumor cells, comprising contacting an LSR antagonist with malignant tumor cells. The therapeutic drug or suppressant for growth of malignant tumor cells according to the embodiment of the present invention may be an agent that reduces the growth rate, amount of growth, or volume of malignant tumor by 10, 20, 30, 40, 50, or 70% or more relative to a case where a therapeutic drug or growth suppressant is not added. The percentage may be within the range of two numerical values listed above.

One embodiment of the present invention is an agent for suppressing cell division of malignant tumor cells, comprising an anti-LSR antibody. Further, it is a method of suppressing cell division of malignant tumor cells, comprising contacting an anti-LSR antibody with malignant tumor cells. Further it is an agent for suppressing cell division of a malignant tumor cell, comprising an LSR antagonist. Further, it is a method of suppressing cell division of malignant tumor cells, comprising contacting an LSR antagonist with malignant tumor cells. The agent for suppressing cell division of a malignant tumor cell according to the embodiment of the present invention may be an agent that reduces the rate of malignant tumor cell division by 10, 20, 30, or 50% or more relative to a case where an agent for suppressing cell division is not added. The percentage may be within the range of two numerical values listed above.

One embodiment of the present invention is a therapeutic drug for LSR-dependent malignant tumor, comprising an anti-LSR antibody. LSR-dependent malignant tumor can be treated by using such a therapeutic drug.

One embodiment of the present invention is use of an anti-LSR antibody or LSR antagonist for producing a therapeutic drug for malignant tumor. In another embodiment, it is a use of an anti-LSR antibody for manufacturing a companion diagnostic drug for malignant tumor therapy targeting an LSR.

One embodiment of the present invention is a method of producing an anti-LSR antibody, comprising: introducing a polynucleotide encoding an LSR into a cell; expressing the LSR in the cell; and immunizing a chicken with an antigen comprising a cell expressing the LSR. According to the production method, an anti-LSR antibody that is excellent for the treatment or diagnosis of LSR positive malignant tumor can be efficiently produced.

"Bond" in one embodiment of the present invention may be either a covalent bond or a non-covalent bond. For example, "bond" may be an ionic bond, hydrogen bond, hydrophobic interaction, or hydrophilic interaction.

(General Techniques)

Molecular biological approach, biochemical approach, and microbiological approach used herein are well known and conventional approaches in the art that are described in, for example, Sambrook J. et al. (1989). Molecular Cloning: A Laboratory Manual, Cold Spring Harbor and $3^{rd}$ Ed. thereof (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press, Bessatsu Jikken Igaku [*Experimental Medicine, Supplemental Volume*], Idenshi Donyu Oyobi Hatsugen Kaiseki Jikken Ho [*Experimental Methods for Transgenesis & Expression Analysis*], Yodosha, 1997, and the like, the relevant portions (which can be the entire document) of which are incorporated herein by reference.

DNA synthesis techniques and nucleic acid chemistry for making an artificially synthesized gene are described in, for example, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman&Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (1996). Bioconjugate Techniques, Academic Press and the like, the relevant portions of which are incorporated herein by reference.

For example, as used herein, the oligonucleotide of the present invention can also be synthesized by a standard method known in the art, such as by using an automated DNA synthesizer (a synthesizer commercially available from Biosearch, Applied Biosystems Or the like). For example, a phosphorothioate-oligonucleotide can also be synthesized by the method of Stein et al. (1988, Mud. Acids Res. 16: 3209), and a methyl phosphonate-oligonucleotide can also be prepared by using a control pore glass polymer support (Sarin et al., 1988, Proc. Natl. Acad. Sci. USA 85: 7448-7451).

As used herein, "or" is used when "at least one or more" of the matters listed in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

As described above, the present invention has been described while showing preferred embodiments to facilitate understanding. The present invention is described below based on Examples. The aforementioned description and the following Examples are not provided to limit the present invention, but for the sole purpose of exemplification. Thus, the scope of the present invention is not limited to the embodiments and Examples specifically described herein and is limited only by the scope of claims.

EXAMPLES

Hereinbelow, the present invention is further described by examples. However, the present invention is not limited to these.

<Example 1> LSR Expression Analysis 1.1 Quantitative Analysis of Cell Surface Membrane Protein According to iTRAQ™ Method (Creative Proteomics, Shirley, N.Y.).

Identification of an ovarian-cancer-specific cancer antigen protein was tried by searching for a cell surface membrane protein highly expressed in ovary serous adenocarcinoma cell strains (OVCAR3, OVSAHO, and JHOS4) in comparison with normal ovarian epithelial cell strains (HOSE2C and E7/TERT). First, for a cell strain cultured in a 150 mm Petri dish, the cell surface membrane proteins were biotinylated with sulfo-NHS-SS-biotin. The extracted proteins were purified by Neurto-avidin beads. At this time, in order to correct the error between the samples, sulfo-NHS-SS-biotin-labeled bovine serum albumin was added to each in an equal amount as an internal standard, and was used for correction of quantification results by a mass spectrometer. The purified proteins were digested by trypsin and labeled with an iTRAQ™ reagent. The samples were mixed into one and it was roughly fractionated into 24 fractions by ion exchange HPLC. Each of the fractions was desalinated and then measured by a mass spectrometer (nano LC-MS/MS) analysis. A data base was searched for the obtained data using proteome discoverer ver. 1.1 and thereby the proteins were identified and quantified. It should be noted that the ovarian cancer surgery tissues used in the examples were provided from patients whose agreements to informed consents were obtained in Osaka University Hospital.

As a result of analysis according to an iTRAQ™ method, it was found that LSR was specifically and highly expressed in the above-mentioned ovary serous adenocarcinoma cell strains as below.

TABLE 1

| Description | E7TERT/<br>HOSE2C | Criteria | OVCAR3 | OVSAHO | JHOS4 |
|---|---|---|---|---|---|
| LSR | 3.092 | HOSE2C | 10.939 | 11.412 | 9.073 |
|  |  | E7/TERT | 5.207 | 5.328 | 3.301 |

1.2 RT-PCR

RNAs of a normal ovarian epithelial cell strain (HOSE2C), ovary serous adenocarcinoma cell strains (OVCAR3, OVSAHO, and JHOS4), ovarian clear cell adenocarcinoma cell strains (OVTOKO, OVMANA, OVISE, and RGMI), normal endometrial cell strains (E6/E7/TERT) and endometrial cancer (HEC1, HEC1A, HEC6, HEC88nu, HEC108, HEC116, HEC251, and SNGM) were each purified by the RNeasymini® kit (QIAGEN). Further, reverse transcription into cDNA was carried out using the QuantiTect® Reverse Transcription Kit (Qiagen). RT-PCR was carried out using the TaKaRaEx® Taq DNA polymerase (Takara Bio, Shiga, Japan). Primers of the following sequences were used in the RT-PCR.

```
LSR:
forward primer
                            (SEQ ID NO: 1993)
5'-GGGAGGACCTCAGGGGTGGC-3'
and reverse primer
                            (SEQ ID NO: 1994)
5'-TGGTGGGGGTGGGGTCTTGG-3';
and β-actin:
forward primer
                            (SEQ ID NO: 1995)
5'-AGCCTCGCCTTTGCCGA-3'
and reverse primer
                            (SEQ ID NO: 1996)
5'-CTGGTGCCTGGGGCG-3'.
```

Figure 1:
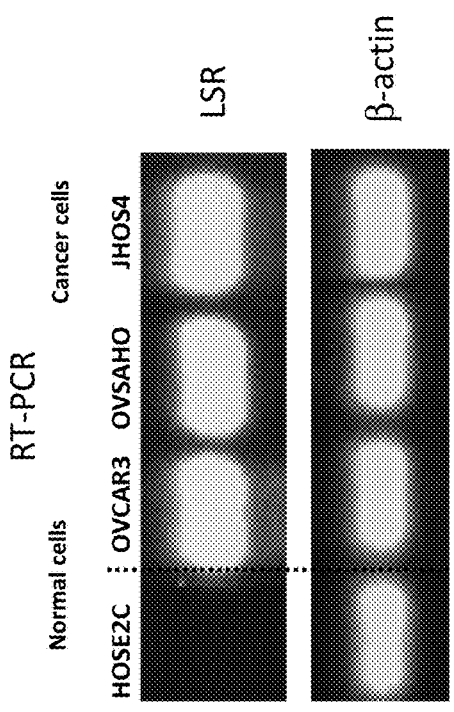
FIG. 1 is a diagram showing results of RT-PCR performed on nucleic acids obtained from ovarian serous adenocarcinoma cell strains. One on the left show normal cells (HOSE2 on the left side). Three on the right show cancer cells (from the left: OVCAR3, OVSAHO, and JHOS4). The top row shows LSRs and the bottom row shows the background β actin.

The results of the above were shown in FIGS. 1 to 3. In the ovary serous adenocarcinoma cell strains OVCAR3, OVSAHO, and JHOS4, the ovarian clear cell adenocarcinoma cell strains OVMANA, OVISE, and RGMI, and the endometrial cancer cell strains HEC1, HEC1A, HEC6, HEC88nu, HEC108, HEC116, HEC251, and SNGM, a band corresponding to LSR mRNA was detected. In the normal ovarian epithelial cell strains, for HOSE2C, it was not detected.

1.3 Western Blot

Ten μg each of proteins obtained from the normal ovarian epithelial cell strain (HOSE2C), the ovary serous adenocarcinoma cell strains (OVCAR3, OVSAHO, SKOV3, JHOS2, and JHOS4), the ovarian clear cell adenocarcinoma cell strains (OVTOKO, OVMANA, OVISE, and RGMI), the normal endometrial cell strains (E6/E7/TERT) and the endometrial cancer (HEC1, HEC1A, HEC6, HEC88nu, HEC108, HEC116, HEC251, and SNGM) were applied to SDS-PAGE (5 to 20% gradient gel (Wako Pure Chemical Industries, Ltd.)). Then, they were subjected to migration at 40 mA for 50 minutes and subsequently transferred to PVDF membranes at 120 mA for 1 hour. After the transfer, blocking was carried out in 1% BSA/TBST (TBS+0.1% Tween 20) at room temperature for 1 hour and then incubation with an anti-LSR antibody (Santa Cruz Biotechnology) was carried out at room temperature for 1 hour. After washing with TBST for 10 minutes three times for each, the PVDF membranes were incubated at room temperature for 1 hour using an HRP-labeled anti-rabbit antibody (GE healthcare) that had been diluted 5,000 times with TBST. The PVDF membranes were washed with TBST for 10 minutes three times for each and then the reacted proteins were detected by a fluorescence reaction system (Perkin Elmer, Inc.).

The results of the above are shown in FIGS. 4 to 6. In the ovary serous adenocarcinoma cell strains OVCAR3, OVSAHO, and JHOS4, ovarian clear cell adenocarcinoma cell strains OVMANA, OVISE, and RGMI, and the endometrial cancer cell strains HEC1, HEC1A, HEC6, HEC88nu, HEC108, HEC116, HEC251, and SNGM, a band corresponding to LSR was detected. Meanwhile, in the ovarian clear cell adenocarcinoma cell strain OVTOKO, a band corresponding to LSR was not detected. In the normal ovarian epithelial cell strain, a band corresponding to LSR was not detected in any of HOSE2C. From the above results, it is understood that the LSR protein is specifically expressed at the above-mentioned cancers.

Moreover, for proteins obtained from normal ovarian tissues, ovary serous adenocarcinoma surgery tissues, ovarian clear cell adenocarcinoma surgery tissues, normal endometrial tissues, and endometrial cancer surgery tissues, Western blot was carried out using an anti-LSR antibody (Santa Cruz Biotechnology). An anti-GAPDH antibody (Santa Cruz Biotechnology) was used as a loading control. The tissues used for the Western blot were obtained from healthy humans or patients suffering from respective cancers.

The results of the above are shown in FIGS. 7 and 8. The black circles in the figures mean that the expression of LSR was confirmed. In the normal ovarian tissue and the normal endometrial tissue, LSR was not expressed. In the ovary serous adenocarcinoma tissue, LSR was specifically expressed in 13/16 people (81%). In the ovarian clear cell adenocarcinoma surgery tissue, LSR was specifically expressed in 4/11 people (36%). In the endometrial cancer tissue, LSR was specifically expressed in 19/35 people (54%). From these results, it was found that while LSR positive patients were present in ovarian cancer patients and uterine cancer patients, a certain number of LSR negative patients were also present.

<Example 2> Making and Evaluation 2.1 Making of Human LSR-Expressing Chicken Cell Strain and Immunization to Chicken cDNA (SEQ ID NO: 7) of human LSR was cloned to a mammalian expression vector (pcDNA3.1-V5/His-TOPO) to make a LSR expression vector. This LSR expression vector encodes a fused protein in which a V5/His tag was fused to the C-terminal of the human LSR. Then, the LSR expression vector was transfected into a chicken lymphoblast-like cell strain according to an electroporation method and then 2 mg/ml of G418 was added to select an expression cell. Chicken was hyperimmunized with the obtained LSR-expressing cell strain. An antibody titer was measured by flow cytometry (FACS) analysis. With regard to the FACS analysis, the protocol of FACSCalibur (BD, USA) was followed.

2.2 Making of scFv Phage Antibody Library from Immunized Chicken Spleen

The spleen was extracted from the immunized chicken and then the lymphocytes were separated. The RNA was extracted from the obtained lymphocytes, a cDNA was synthesized, and a scFv phage antibody library was made. For the making of a scFv phage antibody library, a technique described in "Nakamura et al., J Vet Med Sci. 2004 July; 66(7): 807-14" was followed.

2.3 Panning Selection

The scFv phage antibody library was added to a non-LSR-expressing cell strain to carry out absorption operation of nonspecific phages, and then was reacted with a LSR-expressing cell strain. In Lot 1, a mammalian cell strain was used and in Lot 2, cell panning was carried out using the chicken lymphoblast-like cell strain used for immunization. After washing with organic solvent, phages specifically binding to the LSR-expressing cell strain were recovered and then *Escherichia coli* were infected with it. Panning was carried out four times and then the reactivity of the library was confirmed by FACS analysis using the LSR-expressing cell strain. Phages from a library of which the reactivity had most increased were cloned, positive clones were selected, and then the sequences of six types of clones were determined (SEQ ID NOs: 1 to 6 and FIG. 9). For cell panning, a method described in "Giordano et al., Nat Med. 2001 November; 7(11): 1249-53" was followed.

2.4 Recombination to Recombinant Mouse/Chicken Chimeric (IgG2a) Antibody

The VH and VL in a chicken-derived antibody gene were PCR amplified using a DNA strand encoding a scFv phage antibody as a template and then were cloned into a mouse/chicken chimeric (IgG2a) expression vector (H chain: pcDNA3.1 and L chain: pcDNA4 (Invitrogen)). The made construct of the H chain and the L chain was transfected into mammalian culture cells and then expressed antibodies (anti-LSR mouse/chicken chimeric monoclonal antibodies) were purified using Protein G Sepharose (GE). From the above, six types of clones of anti-LSR antibodies (#9-7, #16-6, No. 26-2, No. 27-6, No. 1-25, and No. 1-43) were obtained. For recombination, a technique described in "Tateishi et al., J Vet Med Sci. 2008 April; 70(4): 397-400" was followed.

2.5 Evaluation of Reactivity to Various Ovary Cancer Cell Strains

Using five types (#1-25, #9-7, #16-6, No. 26-2, and No. 27-6) from the anti-LSR antibodies obtained in 2.4 described above, the reactivity to various ovary cancer cell strains was investigated by FACS analysis. The results are shown in FIGS. 10 to 14. In ovary serous adenocarcinoma cell strains (OVSAHO and JHOS2) and ovarian clear cell adenocarcinoma cell strains (RGM-I and OVISE), a significant shift difference was observed by the presence or absence of the anti-LSR antibodies.

Immunohistochemical Staining

For tissues of ovarian cancer (84) cases, the expression of LSR was analyzed by immunohistochemical staining. A primary antibody from Cloud Clone Corp. (PAD744Hu01) was used and the Dako ChemMate™ ENVISION™ Kit/HRP (DAB)-universal kit (K5007) was used to carry out staining.

Results of the immunohistochemical staining were rated with scores. The score rating was on a five-point scale: 0+(no staining cell); 1+(pale staining in any proportion of cells); 2+(darkly staining cells (<25% of area)); 3+(darkly staining cells (25 to 49% of area); and 4+(dark staining (>50% area)). Scores 0, 1, and 2 were classified as a LSR low expression group and scores 3 and 4 were classified as a LSR high expression group. They were classified into the groups of the LSR low expression group and the LSR high expression group, a survival curve was created using the Kaplan-Meier method, and a log-rank test was carried out.

Consequently, in ovary serous adenocarcinoma, it became clear that prognosis in the LSR high-expression cases was significantly worse than that in the low-expression cases (median OS: 73.8 vs 105.5 months) (p=0.0293). Meanwhile, although a significant difference is not recognized in ovarian clear cell adenocarcinoma, it was observed that prognosis in the LSR high-expression cases tended to be worse than that in the low-expression cases (median OS: 71.4 vs 87.4 months) (p=0.1362). In each of ovary serous adenocarcinoma and ovarian clear cell adenocarcinoma, the expression of LSR was examined for surgery tissues of lymph node metastasis sites and greater omentum metastasis sites according to an immunohistochemical staining method and consequently it was confirmed that LSR is expressed at cancer tissues of the metastasis sites.

As shown in FIG. 29, previously, there was no effective therapeutic method for recurrent ovarian cancer. Conventionally, there was no effective therapeutic method for recurrent ovarian cancer. The epidemiological characteristic of ovarian cancer is that ovarian cancer readily infiltrate into the surrounding by the lymph node and peritoneal metastasis or the like and advances quickly. For instance, 40% or more of ovarian cancer in Japanese patients is considered serous, 24% clear cells, 17% endometrioid, and 13% mucinous adenocarcinoma. As a 1st line of defense, cisplatin or taxol is used, and Avastin is used for recurrent ovarian cancer. However, it was considered that improvement in survival rate was not observed. Antibody pharmaceutical products approved as a therapeutic drug for cancer include those shown in the table of FIG. 29 (Carter P J Nat. Rev. Immunol. 006, May 6(5)343-357, Review). Since there is no therapeutic method for the advanced stage and the time of recurrence, ovarian cancer is presumed to be poor prognostic tumor and the development of a novel therapeutic method is presumed urgent. For example, as shown in FIG. 29, the five year survival rate in Stage IV was 31% (Japan Society of Obstetrics and Gynecology, Fujinka shuyoui iinkai houkoku [*Gynecology tumor committee report*], 2012, vol. 64, No. 6).

In this regard, the inventors confirmed as shown in FIG. 30 whether LSR is expressed at the ovarian cancer primary site. The protocol of it is as below. It should be noted that a technique similar to the above-mentioned technique in the present example was used in immunostaining of LSR. The expression of LSR was analyzed by immunohistochemical staining. A primary antibody from Cloud Clone Corp. (PAD744Hu01) was used and the Dako ChemMate™ ENVISION™ Kit/HRP (DAB)-universal kit (K5007) was used to carry out staining.

In addition, using proteins extracted from ovarian cancer surgery tissue, the expression of LSR was examined according to the Western blot method. Consequently, it became clear that LSR is more highly expressed in ovarian clear cell adenocarcinoma and ovary serous adenocarcinoma than normal ovarian tissue. GAPDH indicated a control group.

The result is shown in FIG. 30. As shown in FIG. 30, it was confirmed that LSR was expressed at the ovarian cancer primary site.

In addition, it was confirmed whether it was expressed at metastasis sites other than the primary site. The protocol of it is shown as below. It should be noted that a technique similar to the above-mentioned technique in the present example was used in immunostaining of LSR. Specifically, the expression of LSR was analyzed by immunohistochemical staining. A primary antibody from Cloud Clone Corp. (PAD744Hu01) was used and the Dako ChemMate™ ENVISION™ Kit/HRP (DAB)-universal kit (K5007) was used to carry out staining.

The results are shown in FIGS. 31 to 32. As shown in these figures, they indicate that it is also expressed at metastasis sites other than the primary site. From these facts, it is understood for the present invention that a LSR antibody medicine can be expected to exhibit an antitumor effect on not only primary ovarian cancer but also metastasis sites.

Then, for the expression of LSR, it was confirmed whether LSR is also expressed in other cells (FIGS. 33 to 35). These include expression at early ovarian clear cell adenocarcinoma, and gastric cancer and signet-ring cell cancer of gastric cancer, which are adenocarcinoma other than ovary cancer. Immunohistochemical staining of LSR was carried out according to a similar technique to the above-mentioned. Specifically, the expression of LSR was analyzed by immunohistochemical staining. A primary antibody from Cloud Clone Corp. (PAD744Hu01) was used and the Dako ChemMate™ ENVISION™ Kit/HRP (DAB)-universal kit (K5007) was used to carry out staining.

The results are shown in FIGS. 33 to 35. As shown in FIG. 33, it indicates that LSR is also expressed at early ovarian clear cell adenocarcinoma. As shown in FIG. 34, it indicates that LSR is also expressed at gastric cancer as adenocarcinoma other than ovarian cancer. In addition, as shown in FIG. 35, it indicates that LSR is also expressed at signet-ring cell cancer of gastric cancer. From these, it is understood that it can be used in the therapy for ovarian cancer even in the early stage and it has therapeutic possibility for other adenocarcinoma such as gastric cancer and the like.

Then, poor prognosis was investigated. In order to confirm whether highly-LSR-expressing ovary serous adenocarcinoma has a poor prognosis in comparison with a low expression group, the prognosis of ovary serous adenocarcinoma patients and ovarian clear cell adenocarcinoma patients was investigated based on being high or low in the expression of LSR. For ovary serous adenocarcinoma, 21 cases of strongly-LSR-expressing patients and 12 cases of weakly-expressing patients were investigated and for ovarian clear cell adenocarcinoma, 27 cases of strongly-LSR-expressing patients and 24 cases of weakly-expressing patients were investigated. The result is shown in FIG. 38. As shown in FIG. 38, it was found that the highly-LSR-expressing ovary serous adenocarcinoma has poor prognosis in comparison with the low expression group.

(Epitope Analysis)

PepStar™ peptide microarrays were made on glass slides obtained from JPT Peptide Technologies (GmbH). Fifteen-mer overlapping peptides that overlap to the extracellular domain region of LSR by 10 amino acids were synthesized and solid-phased to glass slides. Binding of a purified recombinant antibody to a peptide was carried out according to the instructions, however, it included changes to some parts (www.jpt.com). A primary antibody was reacted at a concentration of 1.0 ng/mL and the glass slides were washed with TBST (50 mM TBS-buffer including 0.1% Tween20, pH 7.2). Then, it was reacted using Cy5-labeled goat anti-chicken IgY (Jackson Immuno Research) and washed with TBST five times and the glass slides were washed with ddH2O five times. The glass slides were dried by spraying argon gas mildly. A fluorescence signal was detected using the GenePix® 4200AL scanner (Molecular Devices) at resolution of 10 μm.

The result is shown in FIG. 39. As shown in FIG. 39, it became clear that there are two types of epitopes and amino acids 116 to 135 (to which the antibodies #9-7, 1-25, 16-6, 26-2, and 1-43 correspond) and amino acids 216 to 230 (to which the antibody #27-6 corresponds) are present.

(Cross Reaction)

In order to investigate that an anti-LSR antibody cross-reacts with mouse LSR, a mouse LSR expression vector or a control vector was transfected into COST cells and the reactivity with various clones of anti-LSR antibodies prepared in the present example was analyzed by FACS®. The result is shown in FIG. 40. Consequently, it became clear that all the clones exhibit cross reaction with mouse LSR. The fact that an anti-LSR antibody cross-reacts with mouse LSR as described above makes it possible to use mice as an animal for a safety test. Please refer to FIG. 52 and thereafter, where actual acute toxicity tests were carried out.

2.6 Expression Analysis of LSR by Immunohistochemical Staining Method

Slices of paraffin-embedded tissues of ovary serous adenocarcinoma tissue and endometrial cancer tissue were deparaffinization-treated and dehydrated with alcohol. Then, using an anti-LSR antibody (#1-25 or #9-7), immunohistochemical staining for LSR was carried out according to the ABC method. The results are shown in FIGS. 15 to 17. In the ovary serous adenocarcinoma tissue and the endometrial cancer tissue, LSR was highly expressed at the tumor sites.
Immunohistochemical Staining Using Normal Frozen Tissue Array FDA standard human tissue microarrays (T6234701-2, Biochain) were immunohistochemically stained using the anti-LSR antibody #1-25. The expression of LSR was observed at liver and testis of various normal tissues (FIGS. 36 and 37).
Calculation of Binding Constant Various concentration of various anti-LSR antibodies were reacted with RMG-I cells and they were stained using goat anti-mouse IgG-FITC (Southern Biotech, Birmingham, Ala., USA) and analyzed by a FACSCanto® II cytometer (Becton Dickinson). With regard to the fluorescence intensity of FITC, a KD value was analyzed using GraphPad Prism® Software Version 6.0 for Windows (GraphPad Software Inc., San Diego, Calif., USA). The result is shown in FIG. 37B. When the binding ability of the made LSR antibodies was analyzed by FACS®, antibodies having a high binding ability were obtained. The following analysis was carried out using two kinds of clones having the highest binding ability in them (FIG. 37B). For #9-7, $K_D$=2.52 nM; for #1-25, $K_D$=2.03 nM; for #16-6, $K_D$=2.33 nM; for #26-2, $K_D$=4.04 nM; for #27-6, $K_D$=4.29 nM; and for #1-43, $K_D$=24.62 nM.
Cell Cycle Analysis Ovarian clear cell adenocarcinoma (RMG-I) was seeded into a 6-well plate at 15,000 cells/well and incubated in a $CO_2$ incubator at 37° C. overnight. The culture supernatant was discarded and 100 µg/ml anti-LSR antibody or mouse IgG2a diluted with RPMI 1640 medium (containing 1% FBS and 1% penicillin-streptomycin) was added at 2 mL/well for each. After 96 hours, cell cycle analysis was carried out using the Cycle Test Plus® DNA Reagent kits (BD Biosciences).
Western Blot Ovarian clear cell adenocarcinoma (RMG-I) was seeded into a 6-well plate at 15,000 cells/well and incubated in a $CO_2$ incubator at 37° C. overnight. The culture supernatant was discarded and 100 µg/ml anti-LSR antibody or mouse IgG2a diluted with RPMI 1640 medium (containing 1% FBS and 1% penicillin-streptomycin) was added at 2 mL/well for each. After 96 hours, proteins were extracted using a RIPA buffer (10 mM Tris-HCl, pH 7.5, 150 mM NaCl, 1% Nonidet® P-40, 0.1% sodium deoxycholate, 0.1% SDS, 1x phosphatase inhibitor cocktail (Nacalai Tesque), and 1× protease inhibitor cocktail (Nacalai Tesque)) and the difference in protein expression was analyzed by the Western blot method. The following antibodies were used as primary antibodies: anti-LSR antibody (sc-133765) and anti-GAPDH antibody (sc-25778) (Santa Cruz Biotechnology (Santa Cruz, Calif.)); and anti-cyclin D1 antibody (#2926), anti-p27 antibody (#3686), anti-phospho-Rb (Ser780) antibody (#9307), anti-phospho-Rb antibody (Ser807/811) (#9308), anti-Rb antibody (#9313), anti-phospho-p44/42 MAPK (Erk1/2) (Thr202/Tyr204) antibody (#4370), anti-p44/42 MAPK (Erk1/2) antibody (#4695), anti-phospho-MEK1/2 (Ser217/221) antibody (#9154), and anti-MEK1/2 antibody (#9126) (Cell Signaling Technology).

<Example 3> Growth Suppression of LSR Positive Malignant Tumor 3.1 Growth Inhibition Assay with Anti-LSR Antibody Ovarian clear cell adenocarcinoma (RMG-I) was seeded into a 96-well plate at 1000 cells/well and incubated in a $CO_2$ incubator at 37° C. overnight. The cell supernatant on the 96-well plate was discarded and diluted solutions (0 µg/ml, 1 µg/ml, 10 µg/ml, and 100 µg/ml) of an anti-LSR antibody (#9-7 or #1-25) were each added at 100 µL/well. After 72 hours, cell growth assay was carried out according to the WST-8 assay method. In addition, mouse IgG2 (Biolegend, Inc., 400224, MOPC-173), which is non-anti-LSR antibody, was used as a control. The results are shown in FIGS. 18 and 19. By contacting an anti-LSR antibody, the growth of ovarian cancer cells (RMG-I) was suppressed.

Ovarian clear cell adenomatous cancer (A2780) was seeded into a 96-well plate at 1000 cells/well and incubated in a $CO_2$ incubator at 37° C. overnight. The cell supernatant on the 96-well plate was discarded and diluted solutions (1 µg/ml, 10 µg/ml, and 100 µg/ml) of an anti-LSR antibody (#9-7 or #26-2) were each added at 100 µL/well. After 72 hours, cell growth assay was carried out according to the WST-8 assay method. In addition, mouse IgG2 (Biolegend, Inc., 400224, MOPC-173), which is non-anti-LSR antibody, was used as a control. The result is shown in FIG. 20. By contacting an anti-LSR antibody, the growth of ovarian cancer cells (A2780) was suppressed.
Cell Cycle Analysis Ovarian clear cell adenomatous cancer (RMG-I) was seeded into a 6-well plate at 15,000 cells/well and incubated in a $CO_2$ incubator at 37° C. overnight. The cell supernatant on the 6-well plate was removed and an anti-LSR antibody (#1-25) that had been diluted to a concentration of 100 µg/ml with RPMI 1640 medium (containing 1% FBS and 1% penicillin-streptomycin) was added at 2 mL/well for each. In addition, mouse IgG2 (Biolegend, Inc., 400224, MOPC-173), which is a non-anti-LSR antibody, was used as a control. Ninety six hours after the addition of the antibody, intracellular DNA was stained using the Cycle Test Plus® DNA Reagent kits (BD Biosciences) and cell cycle analysis was carried out using a FACSCanto® flow cytometer.

The result is shown in FIG. 41. It was recognized that by contacting the anti-LSR antibody, the S phase and the G2/M phase in the cell cycle of ovarian cancer cells (RMG-I) were significantly decreased and the G0/G1 phase was significantly increased in comparison with the control antibody-treatment group.
Western Blot Analysis Ovarian clear cell adenomatous cancer (RMG-I) was seeded into a 6-well plate at 15,000 cells/well and incubated in a $CO_2$ incubator at 37° C. overnight. The cell supernatant on the 6-well plate was removed and an anti-LSR antibody (#1-25) that had been diluted to a concentration of 100 µg/ml with RPMI 1640 medium (containing 1% FBS and 1% penicillin-streptomycin) was added at 2 mL/well for each. In addition, mouse IgG2 (Biolegend, Inc., 400224, MOPC-173), which is a non-anti-LSR antibody, was used as a control. Seventy two hours after the addition of the antibody, proteins were extracted, the expression variation of proteins related to the cell cycle was analyzed by the Western blot method using the following various antibodies: anti-cyclin D1 (#2926), anti-p27 (#3686), anti-phospho-Rb (Ser780) (#9307), anti-phospho-Rb (Ser807/811) (#9308), anti-Rb (#9313), anti-phospho-p44/42 MAPK (Erk1/2) (Thr202/Tyr204) (#4370), anti-p44/42 MAPK (Erk1/2) (#4695), antiphospho-MEK1/2 (Ser217/221) (#9154), and anti-MEK1/2 (#9126) (Cell Signaling Technology).

The result is shown in FIG. 42. It was recognized that by contacting the anti-LSR antibody, the expression of Cyclin D1 was decreased and the expression of p27 was increased in the ovarian cancer cells (ovarian cancer cells (RMG-I)) in comparison with the control antibody. Moreover, it was recognized that the phosphorylation levels of phospho-Rb (Ser780) (#9307) and phospho-Rb (Ser807/811) were decreased. It was also recognized that the phosphorylation levels of phospho-MEK1/2 (Ser217/221) and phospho-p44/42 MAPK (Erk1/2) (Thr202/Tyr204) as kinases related to cell growth were decreased.

The above result indicates that the anti-LSR antibody directly suppressed the growth of malignant tumor cells, and it was a surprising result. As the mechanism of this, for example, it is thought that the anti-LSR antibody binds to a malignant tumor cell, thereby a cell clump of malignant tumor cells was formed, and consequently the cell division was suppressed.

3.2 Epitope Analysis

For the anti-LSR antibodies obtained in 2.4 described above, epitopes were analyzed as mentioned above and specifically identified. In addition, a growth suppressing effect on LSR positive malignant tumor is investigated for the anti-LSR antibodies for which the epitopes were identified. Consequently, it is understood that an anti-LSR antibody recognizing a specific epitope significantly suppresses the growth of LSR positive malignant tumor in comparison with anti-LSR antibodies recognizing other epitopes.

3.3 Growth Inhibition Assay with siRNA

Ovary serous adenocarcinoma cells (OVSAHO) were seeded into a 96-well plate at 1000 cells/well and incubated in a $CO_2$ incubator at 37° C. overnight. The cell supernatant on the 96-well plate was discarded and the siRNA was transfected with LIPOFECTAMINE® 2000. After 120 hours, cell growth assay was carried out according to the WST-8 assay method. LSR siRNA and negative control siRNA were obtained from QIAGEN. The LSR siRNA has a RNA sequence complementary to LSR mRNA (LSR siRNA 1: SEQ ID NO: 9 and LSR siRNA 2: SEQ ID NO: 10). The result is shown in FIG. 21. By contacting the LSR siRNA, the growth of ovarian cancer cells (OVSAHO) was suppressed.

3.4 Relation to Lipid Metabolism

It is confirmed whether the uptake of lipids (cholesterol) is elevated in stably LSR-expressing cells described in the Examples. After confirming whether the VLDL metabolism is elevated, it was confirmed whether the elevation in metabolism due to VLDL is inhibited by administration of a LSR antibody.

The protocol is shown as below.

Lipids were quantified using an empty vector strain of SKOV3 (EMP1) and a LSR-forcibly expressing strain (L45). In a low concentration, they were seeded at $5 \times 10^5$ cells per 10 cm dish and, in a high concentration, at $5 \times 10^5$ cells per 10 cm dish and were cultured for 48 hours. The mediums were not exchanged. By adding a methanol+chloroform mixture solution to cells suspended in PBS and centrifuging it, an organic layer as the lower layer was recovered to extract lipids. Lipids were quantified using LabAssay™ Triglyceride (GPO/DAOS method, Wako Pure Chemical Industries, Ltd.), LabAssay™ Cholesterol (cholesterol oxidase/DAOS method, Wako Pure Chemical Industries, Ltd.), and Phospholipid C-test WAKO™ (choline oxidase/DAOS method, Wako Pure Chemical Industries, Ltd.). The metabolism elevation due to VLDL was measured using the Extracellular Flux Analyzer XFe24™ (Primetech Corporation). Assay was carried out after glucose in the buffer was removed, glutamine was added, and the antibody amount was increased from 10 ug/ml to 100 ug/ml.

Consequently, on day 1, the high was conf: 100% and the Low was 50 to 60%. On day 2, the High was 100% and the Low was 70%.

The results are shown in FIGS. 22 to 24. As shown in FIG. 22, the uptake of lipids (cholesterol) was elevated in the stably LSR-expressing cells described in the Examples. As shown in FIG. 23, the uptake of lipids (cholesterol) in high-density culture was elevated in the stably LSR-expressing cells described in the Examples. As shown in FIG. 24, although the LSR expression described in the Examples make the VLDL metabolism elevated, the elevation of metabolism due to VLDL was inhibited by administration of a LSR antibody (#9-7). In #1-25, although the inhibition of metabolism elevation was observed in some degree, the degree was less than #9-7. While not wishing to be bound by theory, this difference is believed due to the difference in epitope recognition sites depending on the clones.

<Example 4> Analysis of Antitumor Effect in Mouse by Anti-LSR Monoclonal Antibody An ovarian clear cell adenomatous cancer cell strain RMG-I was subcutaneously implanted to Scid mice (6-week old, female) at $1 \times 10^6$ cells/100 µl (PBS:Matrigel®=1:1). On day 14 after the implantation, the mice were divided into two groups and an anti-LSR antibody (#1-25) or an isotype control antibody (Mouse IgG2a, M7769, Sigma) was intraperitoneally administered at 10 mg/kg at a frequency of twice a week and a total of 6 times (FIG. 25). The RMG-I-implanted mice were dissected on day 25 after the start of the antibody administration, and the tumor weight was also measured. The following was calculated: tumor volume=major axis×minor axis×height.

As a result of measuring a tumor volume, a significantly inhibitory effect on tumor growth in vivo was exhibited in the anti-LSR antibody administered group relative to the control IgG administered group (FIGS. 26 to 28). A significant difference in tumor weight was also recognized.

<Example 5> Analysis of Antitumor Effect in Mouse by Anti-LSR Monoclonal Antibody An ovarian clear cell adenomatous cancer cell strain RMG-I was subcutaneously implanted to NOD/Scid mice (6-week old, female) at $1 \times 10^6$ cells/100 µl (PBS:Matrigel®=1:1). On day 14 after the implantation, the mice were divided into two groups and an anti-LSR antibody (#1-25) or an isotype control antibody (Mouse IgG2a, M7769, Sigma) was intraperitoneally administered at 10 mg/kg at a frequency of twice a week and a total of 6 times (FIG. 43). The RMG-I-implanted mice were dissected on day 25 after the start of the antibody administration, and the tumor weight was also measured. The following was calculated: tumor volume=major axis×minor axis×height.

As a result of measuring a tumor volume, in the NOD/Scid mice, a significantly inhibitory effect on tumor growth in vivo was exhibited in the anti-LSR antibody administered group relative to the control IgG administered group (FIG. 44). A significant difference in tumor weight was also recognized. In addition, as a result of immunohistochemically staining a tumor tissue with an anti-Ki-67 antibody, a significant decrease in the number of Ki-67 positive cell was recognized in the anti-LSR antibody administered group in comparison with the control IgG administered group. From this, it became clear that the anti-LSR antibody exhibits activity of inducing the arrest of the cell cycle in vivo (FIG. 45).

<Example 6> Analysis of Antitumor Effect in Mouse by Anti-LSR Monoclonal Antibody SKOV3-L45 in which a LSR negative ovary serous adenocarcinoma cell strain SKOV3 was made stably express LSR, or SKOV3-E1 into which an empty vector had been gene-transferred was subcutaneously implanted to Scid mice (6-week old, female) at $5 \times 10^5$ cells/100 μl (PBS:Matrigel®=1:1). On day 14 after the implantation, the mice were divided into two groups and an anti-LSR antibody (#1-25) or an isotype control antibody (Mouse IgG2a, M7769, Sigma) was intraperitoneally administered at 10 mg/kg at a frequency of every other day and a total of 8 times (FIG. 46). The mice were dissected on day 18 after the start of the antibody administration, and the tumor weight was also measured. The following was calculated: tumor volume=major axis×minor axis×height.

As a result of measuring a tumor volume, in the SKOV3-L45-implanted Scid mice, a significantly inhibitory effect on tumor growth in vivo was exhibited in the anti-LSR antibody administered group relative to the control IgG administered group (FIG. 47). Meanwhile, in the tumor volume of the mice into which the LSR negative SKOV3-E1 had been implanted, a significant difference was not recognized (FIG. 47). A similar result was also obtained in tumor weight (FIG. 48). From this, it was suggested that in order for an anti-LSR antibody to exhibit an antitumor effect, it is necessary that LSR is expressed at tumor cells.

Tumors of the SKOV3-L45-implanted Scid mice and the SKOV3-E1-implanted Scid mice were extracted and fat droplets were observed by electronmicroscopy. Consequently, in the SKOV3-L45-implanted tissue, many accumulations of fat droplets were recognized in comparison with the SKOV3-E1-implanted tumor tissue (FIG. 49). In the stably LSR-expressing cell strain and the control-vector-expressing cell strain, when fat droplets after the VLDL administration were compared, it was recognized that fat droplets in the LSR-expressing cell strain are larger and the number thereof is greater.

In order to investigate that an anti-LSR antibody binds to LSR and exhibits activity of internalizing in a cell, an antibody labeling was prepared using CypHer® 5E mono NHS ester dye (GE Healthcare) and was used in an assay. A LSR positive cell strain SKOV3-L45 cell strain and a LSR negative cell strain SKOV3-E1 and a CypHer® 5E-labeled antibody were incubated for 3 hours and they were observed by the In cell analyzer 2000. Consequently, all the clones of #9-7, #1-25, #16-6, #26-2, and #27-6 exhibited activity of internalizing (FIGS. 50 and 52). FIG. 50 shows that if an anticancer agent is conjugated to an antibody, it is applicable as an antibody-drug conjugate (ADC). FIG. 51 shows that if an anticancer agent is conjugated to an antibody, it is applicable as an antibody-drug conjugate (ADC).

These experiments were carried out as below. Tumor tissues were extracted from subcutaneously-RMG-I-implanted NOD/SCID mice to which a control antibody or the anti-LSR antibody #1-25 has been administered. From the tumor tissues, formalin fixed paraffin embedded blocks were made and the expression of Ki67 was analyzed by immunohistochemical staining. A primary antibody from Leica Biosystems Inc. (NCL-L-Ki67-MM1) was used and staining was carried out using the Dako ChemMate™ ENVISION™ Kit/HRP (DAB)-universal kit (K5007). As a result of calculating the proportion of Ki-67 positive cells in the respective visual fields, a significant decrease in the proportion of Ki-67 positive cells was recognized in the anti-LSR antibody #1-25 administered group in comparison with the control antibody administered group. From this, it was suggested that by administering the anti-LSR antibody #1-25, the cell cycle arrest is also induced in vivo.

Example 7: Safety Test

Then, a safety test was carried out for an antibody of the present invention. Since the anti-LSR antibody #1-25 also exhibits cross reaction with mouse LSR, an acute toxicity test in the case of administration to a mouse was carried out. One mg of Mouse IgG2a (Sigma, M7769) or the anti-LSR antibody #1-25 was intraperitoneally administered to each of male and female C57BL/6J(8w) mice, the mice were dissected on day 7, the brain, heart, kidney, liver, lung, and spleen were extracted, and pathological analysis by HE staining was carried out. In addition, the blood was collected and analyzed using an automated blood cell counting device (VetScan® HMII) and a biochemical blood analyzer for animal (VetScan® VS2) (FIG. 52). Consequently, in the data of blood cell number, any significant change was not recognized in the both (FIGS. 53 and 54). Similarly, in the blood biochemical data, any significant change was not recognized in the both (FIGS. 55 and 56). From this, it is understood that the anti-LSR antibody #1-25 has low toxicity and high safety.

The above Examples 1 to 4 show the following: (i) on contacting an anti-LSR antibody with malignant tumor cells, the growth of the malignant tumor cells is suppressed; (ii) on making a LSR antagonist act on malignant tumor cells, the growth of the malignant tumor cells is suppressed; (iii) by administering an anti-LSR antibody to a malignant tumor patient, the therapy for malignant tumor can be carried out; (vi) while LSR positive patients were present in malignant tumor patients, a certain number of LSR negative patients were also present; (v) in malignant tumor therapy in which LSR is targeted, it is important to diagnose whether LSR positive is present or absent in a malignant tumor patient before the therapy; and the like.

As above, the present invention is described based on the examples. These examples are only illustrations and those skilled in the art will understand that various variations are possible and such variations also fall within the scope of the present invention.

As described above, the present invention is illustrated by preferable embodiments of the present invention. However, it will be understood that the scope of the present invention should be interpreted only by the claims. It will be understood that the contents of patents, patent applications, and literatures cited in the present specification should be incorporated by reference to the present specification as if their contents per se are specifically described in the present specification. The present application claims priority to Japanese Patent Application No. 2013-272084 (filed on Dec. 27, 2013) and it is understood that with regard to the contents of them, its contents should be incorporated by reference to the present specification as if its contents per se is specifically described in the present specification.

INDUSTRIAL APPLICABILITY

Malignant tumor markers and malignant tumor control technologies are provided and technologies applicable in industries (reagents, medicine manufacture, and the like) involved in technologies related to diagnosis, therapy, and prophylaxis of malignant tumor are provided.

SEQUENCE LISTING FREE TEXT

SEQ ID NO: 1: the anti-LSR antibody 9-7 sequence
SEQ ID NO: 2: the anti-LSR antibody 16-6 sequence
SEQ ID NO: 3: the anti-LSR antibody 26-2 sequence
SEQ ID NO: 4: the anti-LSR antibody 27-6 sequence
SEQ ID NO: 5: the anti-LSR antibody 1-25 sequence
SEQ ID NO: 6: the anti-LSR antibody 1-43 sequence
SEQ ID NO: 7: human LSR protein sequence (NP_991403.1)
SEQ ID NO: 8: human LSR nucleic acid sequence (NM_205834.3)
SEQ ID NO: 9: the core sequence (guide sequence) of LSR siRNA 1
SEQ ID NO: 10: the core sequence (guide sequence) of LSR siRNA 2
SEQ ID NO: 11: the antisense sequence of the core sequence (guide sequence) of LSR siRNA 1
SEQ ID NO: 12: the antisense sequence of the core sequence (guide sequence) of LSR siRNA 2
SEQ ID NO: 13: the sense full length sequence of LSR siRNA 1
SEQ ID NO: 14: the sense full length sequence of LSR siRNA 2
SEQ ID NO: 15: the antisense full length sequence of LSR siRNA 1
SEQ ID NO: 16: the antisense full length sequence of LSR siRNA 2
SEQ ID NO: 17: LSR forward primer sequence
SEQ ID NO: 18: LSR reverse primer sequence
SEQ ID NO: 19: β-actin forward primer sequence
SEQ ID NO: 20: β-actin forward primer sequence

The invention claimed is:

1. An anti-lipolysis stimulated lipoprotein receptor (anti-LSR) antibody or an antigen binding fragment thereof, the antibody being selected from the group consisting of:
   (a) an antibody with heavy chain CDRs 1, 2, and 3 and light chain CDRs 1, 2, and 3 comprising amino acid sequences set forth in positions 31-35, 50-66, 99-104, 153-165, 182-188 and 221-230 of SEQ ID NO: 1, respectively;
   (b) an antibody with heavy chain CDRs 1, 2, and 3 and light chain CDRs 1, 2, and 3 comprising amino acid sequences set forth in positions 31-35, 50-66, 99-103, 152-165, 182-188 and 221-230 of SEQ ID NO: 2, respectively;
   (c) an antibody with heavy chain CDRs 1, 2, and 3 and light chain CDRs 1, 2, and 3 comprising amino acid sequences set forth in positions 31-35, 50-66, 99-104, 153-165, 182-188 and 221-229 of SEQ ID NO: 3, respectively;
   (d) an antibody with heavy chain CDRs 1, 2, and 3 and light chain CDRs 1, 2, and 3 comprising amino acid sequences set forth in positions 31-35, 50-66, 99-104, 153-165, 182-188 and 221-229 of SEQ ID NO: 4, respectively;
   (e) an antibody with heavy chain CDRs 1, 2, and 3 and light chain CDRs 1, 2, and 3 comprising amino acid sequences set forth in positions 31-35, 50-66, 99-104, 153-165, 182-188 and 221-229 of SEQ ID NO: 5, respectively;
   (f) an antibody with heavy chain CDRs 1, 2, and 3 and light chain CDRs 1, 2, and 3 comprising amino acid sequences set forth in positions 31-35, 50-66, 99-104, 153-165, 182-188 and 221-229 of SEQ ID NO: 6, respectively; and
   (g) a mutant of the antibody according to any one or more of (a)-(f), which is free of a mutation in the CDRs but comprises one or several substitutions, additions, or deletions in a framework of the mutant of the antibody.

2. The anti-LSR antibody or an antigen binding fragment thereof of claim 1, which antibody is selected from a monoclonal antibody, polyclonal antibody, chimeric antibody, humanized antibody, human antibody, multifunctional antibody, bispecific or oligospecific antibody, single chain antibody, scFV, diabody, sc(Fv)$_2$ (single chain (Fv)$_2$), and scFv-Fc.

* * * * *

```
                          SEQUENCE LISTING

<160> NUMBER OF SEQ ID NOS: 22

<210> SEQ ID NO 1
<211> LENGTH: 238
<212> TYPE: PRT
<213> ORGANISM: Gallus gallus

<400> SEQUENCE: 1

Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Ser Asp Tyr
                20                  25                  30

Gln Met Asn Trp Val Arg Gln Ala Pro Ser Lys Gly Leu Glu Trp Val
            35                  40                  45

Ala Gly Ile Asn Gly Arg Ser Ser Trp Thr Asp Tyr Gly Ala Ala Val
        50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Ala Arg Gly Ser Ser Ile Asp Ala Trp Gly His Gly Thr Glu Val Ile
            100                 105                 110

Val Ser Thr Gly Gly Gly Gly Ser Gly Gly Gly Gly Ser Gly Gly Gly
        115                 120                 125

Gly Ser Asp Val Ala Leu Thr Gln Pro Ala Ser Val Ser Ala Asn Pro
    130                 135                 140

Gly Glu Thr Val Lys Ile Thr Cys Ser Gly Gly Gly Ser Tyr Tyr Gly
145                 150                 155                 160

Ser Tyr Tyr Tyr Gly Trp Tyr Gln Gln Lys Ser Pro Gly Ser Ala Pro
                165                 170                 175

Val Thr Met Ile Tyr Asn Asn Asn Arg Pro Ser Asn Ile Pro Ser
            180                 185                 190

Arg Phe Ser Gly Ser Leu Ser Gly Ser Thr Asn Thr Leu Thr Ile Thr
        195                 200                 205

Gly Val Gln Ala Asp Glu Ala Val Tyr Tyr Cys Gly Ser Ile Asp Ser
    210                 215                 220

Asn Ile Ala Gly Val Phe Gly Ala Gly Thr Thr Leu Thr Val
225                 230                 235
```

```
<210> SEQ ID NO 2
<211> LENGTH: 239
<212> TYPE: PRT
<213> ORGANISM: Gallus gallus

<400> SEQUENCE: 2

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Asn Asp Tyr
            20                  25                  30

Gly Met Asn Trp Val Arg Gln Ala Pro Ser Lys Gly Leu Glu Trp Val
        35                  40                  45

Ala Gly Ile Asn Gly Arg Ser Thr Trp Thr Asp Tyr Gly Ala Ala Val
    50                  55                  60

Lys Gly Arg Ala Thr Ile Ser Arg Asp Asn Gly Gln Ser Thr Val Arg
65                  70                  75                  80

Gln Leu Asn Asn Leu Arg Ala Glu Asp Thr Ala Thr Tyr Phe Cys Ala
                85                  90                  95

Arg Gly Ser Ser Ile Asp Ala Trp Gly His Gly Thr Glu Val Ile Val
            100                 105                 110

Ser Thr Gly Gly Gly Gly Ser Gly Gly Gly Ser Gly Gly Gly Gly
        115                 120                 125

Ser Asp Val Ala Leu Thr Gln Pro Ala Ser Val Ser Ala Asn Pro Gly
130                 135                 140

Glu Thr Val Lys Ile Thr Cys Ser Gly Gly Ser Tyr Tyr Gly Thr
145                 150                 155                 160

Tyr Tyr Phe Tyr Gly Trp Tyr Gln Gln Lys Ala Pro Gly Ser Ala Pro
                165                 170                 175

Val Thr Leu Ile Tyr Asp Asn Thr Asn Arg Pro Ser Asn Ile Pro Ser
            180                 185                 190

Arg Phe Ser Gly Ser Thr Ser Gly Ser Thr Ser Thr Leu Thr Ile Thr
        195                 200                 205

Gly Val Gln Val Asp Asp Glu Ala Val Tyr Phe Cys Gly Ser Ile Asp
    210                 215                 220

Ser Ser Tyr Ser Gly Ile Phe Gly Ala Gly Thr Thr Leu Thr Val
225                 230                 235

<210> SEQ ID NO 3
<211> LENGTH: 238
<212> TYPE: PRT
<213> ORGANISM: Gallus gallus

<400> SEQUENCE: 3

Ala Val Thr Leu Asp Glu Ser Gly Gly Gly Leu Gln Thr Pro Gly Gly
1               5                   10                  15

Gly Leu Ser Leu Val Cys Lys Gly Ser Gly Phe Thr Phe Ser Asn Tyr
            20                  25                  30

Glu Met Gln Trp Val Arg Gln Ala Pro Gly Lys Gly Leu Glu Trp Val
        35                  40                  45

Ala Gly Ile Ser Gly Ala Gly Ser Thr Thr Arg Tyr Gly Ser Ala Val
    50                  55                  60

Gln Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Arg Gly Ser Asn Ile Asp Gly Trp Gly His Gly Thr Glu Val Ile
```

```
                100             105             110
Val Ser Thr Gly Gly Gly Ser Gly Gly Gly Ser Gly Gly
            115             120             125
Gly Ser Asp Val Ala Leu Thr Gln Pro Ser Ser Val Ser Ala Asn Pro
            130             135             140
Gly Glu Thr Val Lys Ile Thr Cys Ser Gly Gly Arg Tyr Ala Glu
145             150             155             160
Ser Tyr Tyr Tyr Ser Trp Phe Gln Gln Lys Ser Pro Gly Ser Ala Pro
            165             170             175
Val Thr Val Ile Tyr Trp Asn Asp Lys Arg Pro Ser Asn Ile Pro Ser
            180             185             190
Arg Phe Ser Gly Ser Leu Ser Gly Ser Thr Asn Thr Leu Thr Ile Thr
            195             200             205
Gly Val Arg Ala Glu Asp Glu Ala Val Tyr Tyr Cys Gly Ala Tyr Glu
            210             215             220
Asp Ser Ser Ala Gly Phe Gly Ala Gly Thr Thr Leu Thr Val
225             230             235
```

<210> SEQ ID NO 4
<211> LENGTH: 238
<212> TYPE: PRT
<213> ORGANISM: Gallus gallus

<400> SEQUENCE: 4

```
Ala Val Thr Leu Asp Glu Ser Gly Gly Gly Leu Gln Met Pro Gly Gly
1               5               10              15
Ala Leu Ser Leu Val Cys Arg Ala Ser Gly Phe Asp Phe Ser Ser Tyr
            20              25              30
Glu Met Gln Trp Ile Arg Gln Ala Pro Gly Lys Gly Leu Glu Trp Val
        35              40              45
Ala Gly Ile Ser Gly Ala Gly Ser Gly Thr Arg Tyr Gly Ser Ala Val
    50              55              60
Lys Gly Arg Ala Thr Ile Ser Arg Asp Asn Gly Gln Ser Thr Val Arg
65              70              75              80
Leu Gln Leu Asn Asn Leu Arg Ala Glu Asp Thr Gly Ile Tyr Phe Cys
            85              90              95
Ala Arg Ser Ser Asn Ile Asp Ala Trp Gly His Gly Thr Glu Val Thr
            100             105             110
Val Ser Thr Gly Gly Gly Ser Gly Gly Gly Ser Gly Gly Gly
            115             120             125
Gly Ser Asp Val Ala Leu Thr Gln Pro Ala Ser Val Ser Ala Asn Leu
            130             135             140
Gly Gly Thr Val Lys Ile Thr Cys Ser Gly Gly Arg Tyr Ala Glu
145             150             155             160
Ser Tyr Tyr Tyr Gly Trp Tyr Gln Gln Lys Ser Pro Gly Ser Thr Pro
            165             170             175
Val Thr Val Ile Tyr Trp Asn Asp Lys Arg Pro Ser Asn Ile Pro Ser
            180             185             190
Arg Phe Ser Gly Ser Leu Ser Gly Ser Thr Asn Thr Leu Thr Ile Thr
            195             200             205
Gly Val Gln Val Glu Asp Glu Ala Val Tyr Phe Cys Gly Ser Tyr Glu
            210             215             220
Asp Ser Arg Ser Ala Phe Gly Ala Gly Thr Thr Leu Thr Val
225             230             235
```

<210> SEQ ID NO 5
<211> LENGTH: 238
<212> TYPE: PRT
<213> ORGANISM: Gallus gallus

<400> SEQUENCE: 5

```
Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Asp Phe Ser Ser Tyr
            20                  25                  30

Glu Met Gln Trp Val Arg Gln Ala Pro Gly Lys Gly Leu Glu Trp Val
        35                  40                  45

Thr Gly Ile Ser Gly Ser Ser Thr Arg Tyr Gly Ser Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Arg Gly Ser Thr Ile Asp Ala Trp Gly His Gly Thr Glu Val Thr
            100                 105                 110

Val Ser Thr Gly Gly Gly Gly Ser Gly Gly Gly Ser Gly Gly Gly
            115                 120                 125

Gly Ser Asp Val Ala Leu Thr Gln Pro Ala Ser Val Ser Ala Asn Pro
130                 135                 140

Gly Glu Thr Val Lys Ile Thr Cys Ser Gly Ser Ser Tyr Ala Gly
145                 150                 155                 160

Ser Tyr Tyr Tyr Gly Trp Tyr Gln Gln Lys Ser Pro Gly Ser Ala Pro
                165                 170                 175

Val Thr Val Ile Tyr Tyr Asn Asp Gln Arg Pro Ser Asp Ile Pro Ser
            180                 185                 190

Arg Phe Ser Gly Ser Thr Ser Gly Ser Thr Ala Thr Leu Thr Ile Thr
        195                 200                 205

Gly Val Gln Val Glu Asp Glu Ala Val Tyr Ile Cys Gly Thr Tyr Glu
    210                 215                 220

Asp Ser Gly Gly Val Phe Gly Ala Gly Thr Thr Leu Thr Val
225                 230                 235
```

<210> SEQ ID NO 6
<211> LENGTH: 238
<212> TYPE: PRT
<213> ORGANISM: Gallus gallus

<400> SEQUENCE: 6

```
Ala Val Thr Leu Asp Glu Ser Gly Gly Gly Leu Gln Thr Pro Gly Gly
1               5                   10                  15

Ala Leu Ser Leu Val Cys Glu Ala Ser Gly Phe Asp Phe Ser Ser His
            20                  25                  30

Glu Met Gln Trp Val Arg Gln Ala Pro Gly Lys Gly Leu Glu Trp Val
        35                  40                  45

Ala Gly Ile Ser Gly Ala Gly Ser Ser Thr Arg Tyr Gly Ser Ala Val
    50                  55                  60

Gln Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95
```

-continued

```
Ala Arg Gly Ser Leu Ile Asp Ala Trp Gly His Gly Thr Glu Val Ile
            100                 105                 110

Val Ser Thr Gly Gly Gly Gly Ser Gly Gly Gly Ser Gly Gly Gly Gly
        115                 120                 125

Gly Ser Asp Val Ala Leu Thr Gln Pro Ala Ser Val Ser Ala Asn Pro
    130                 135                 140

Gly Glu Thr Val Lys Ile Thr Cys Ser Gly Gly Ser Tyr Tyr Gly
145                 150                 155                 160

Ser Tyr Tyr Tyr Ser Trp His Gln Gln Lys Ser Pro Gly Ser Ala Pro
                165                 170                 175

Val Thr Val Ile Tyr Glu Asn Asn Gln Arg Pro Ser Asp Ile Pro Ser
            180                 185                 190

Arg Phe Ser Gly Ser Lys Ser Gly Ser Thr Ala Thr Leu Thr Ile Thr
        195                 200                 205

Gly Val Gln Ala Glu Asp Glu Ala Val Tyr Phe Cys Gly Ser Tyr Asp
    210                 215                 220

Ser Ser Ala Gly Leu Phe Gly Ala Gly Thr Thr Leu Thr Val
225                 230                 235

<210> SEQ ID NO 7
<211> LENGTH: 649
<212> TYPE: PRT
<213> ORGANISM: Homo sapiens

<400> SEQUENCE: 7

Met Gln Gln Asp Gly Leu Gly Val Gly Thr Arg Asn Gly Ser Gly Lys
1               5                   10                  15

Gly Arg Ser Val His Pro Ser Trp Pro Trp Cys Ala Pro Arg Pro Leu
            20                  25                  30

Arg Tyr Phe Gly Arg Asp Ala Arg Ala Arg Ala Gln Thr Ala Ala
        35                  40                  45

Met Ala Leu Leu Ala Gly Gly Leu Ser Arg Gly Leu Gly Ser His Pro
    50                  55                  60

Ala Ala Gly Arg Asp Ala Val Val Phe Val Trp Leu Leu Leu Ser
65                  70                  75                  80

Thr Trp Cys Thr Ala Pro Ala Arg Ala Ile Gln Val Thr Val Ser Asn
                85                  90                  95

Pro Tyr His Val Val Ile Leu Phe Gln Pro Val Thr Leu Pro Cys Thr
            100                 105                 110

Tyr Gln Met Thr Ser Thr Pro Thr Gln Pro Ile Val Ile Trp Lys Tyr
        115                 120                 125

Lys Ser Phe Cys Arg Asp Arg Ile Ala Asp Ala Phe Ser Pro Ala Ser
    130                 135                 140

Val Asp Asn Gln Leu Asn Ala Gln Leu Ala Ala Gly Asn Pro Gly Tyr
145                 150                 155                 160

Asn Pro Tyr Val Glu Cys Gln Asp Ser Val Arg Thr Val Arg Val Val
                165                 170                 175

Ala Thr Lys Gln Gly Asn Ala Val Thr Leu Gly Asp Tyr Tyr Gln Gly
            180                 185                 190

Arg Arg Ile Thr Ile Thr Gly Asn Ala Asp Leu Thr Phe Asp Gln Thr
        195                 200                 205

Ala Trp Gly Asp Ser Gly Val Tyr Tyr Cys Ser Val Val Ser Ala Gln
    210                 215                 220

Asp Leu Gln Gly Asn Asn Glu Ala Tyr Ala Glu Leu Ile Val Leu Gly
225                 230                 235                 240
```

```
Arg Thr Ser Gly Val Ala Glu Leu Leu Pro Gly Phe Gln Ala Gly Pro
            245                 250                 255

Ile Glu Asp Trp Leu Phe Val Val Val Cys Leu Ala Ala Phe Leu
        260                 265                 270

Ile Phe Leu Leu Leu Gly Ile Cys Trp Cys Gln Cys Cys Pro His Thr
            275                 280                 285

Cys Cys Cys Tyr Val Arg Cys Pro Cys Cys Pro Asp Lys Cys Cys Cys
    290                 295                 300

Pro Glu Ala Leu Tyr Ala Ala Gly Lys Ala Ala Thr Ser Gly Val Pro
305                 310                 315                 320

Ser Ile Tyr Ala Pro Ser Thr Tyr Ala His Leu Ser Pro Ala Lys Thr
                325                 330                 335

Pro Pro Pro Pro Ala Met Ile Pro Met Gly Pro Ala Tyr Asn Gly Tyr
            340                 345                 350

Pro Gly Gly Tyr Pro Gly Asp Val Asp Arg Ser Ser Ala Gly Gly
                355                 360                 365

Gln Gly Ser Tyr Val Pro Leu Leu Arg Asp Thr Asp Ser Ser Val Ala
    370                 375                 380

Ser Glu Val Arg Ser Gly Tyr Arg Ile Gln Ala Ser Gln Gln Asp Asp
385                 390                 395                 400

Ser Met Arg Val Leu Tyr Tyr Met Glu Lys Glu Leu Ala Asn Phe Asp
                405                 410                 415

Pro Ser Arg Pro Gly Pro Pro Ser Gly Arg Val Glu Arg Ala Met Ser
            420                 425                 430

Glu Val Thr Ser Leu His Glu Asp Asp Trp Arg Ser Arg Pro Ser Arg
                435                 440                 445

Gly Pro Ala Leu Thr Pro Ile Arg Asp Glu Glu Trp Gly Gly His Ser
450                 455                 460

Pro Arg Ser Pro Arg Gly Trp Asp Gln Glu Pro Ala Arg Glu Gln Ala
465                 470                 475                 480

Gly Gly Gly Trp Arg Ala Arg Arg Pro Arg Ala Arg Ser Val Asp Ala
                485                 490                 495

Leu Asp Asp Leu Thr Pro Pro Ser Thr Ala Glu Ser Gly Ser Arg Ser
            500                 505                 510

Pro Thr Ser Asn Gly Gly Arg Ser Arg Ala Tyr Met Pro Pro Arg Ser
            515                 520                 525

Arg Ser Arg Asp Asp Leu Tyr Asp Gln Asp Ser Arg Asp Phe Pro
    530                 535                 540

Arg Ser Arg Asp Pro His Tyr Asp Asp Phe Arg Ser Arg Glu Arg Pro
545                 550                 555                 560

Pro Ala Asp Pro Arg Ser His His His Arg Thr Arg Asp Pro Arg Asp
                565                 570                 575

Asn Gly Ser Arg Ser Gly Asp Leu Pro Tyr Asp Gly Arg Leu Leu Glu
            580                 585                 590

Glu Ala Val Arg Lys Lys Gly Ser Glu Glu Arg Arg Pro His Lys
                595                 600                 605

Glu Glu Glu Glu Glu Ala Tyr Tyr Pro Pro Ala Pro Pro Pro Tyr Ser
    610                 615                 620

Glu Thr Asp Ser Gln Ala Ser Arg Glu Arg Arg Leu Lys Lys Asn Leu
625                 630                 635                 640

Ala Leu Ser Arg Glu Ser Leu Val Val
                645
```

<210> SEQ ID NO 8
<211> LENGTH: 2292
<212> TYPE: DNA
<213> ORGANISM: Homo sapiens

<400> SEQUENCE: 8

```
tcagcccact tccggggagg gaggcagagg aacccctccc cgccgctcac ccctaagccc        60
agccctcggc tcccacccTt gtgtacctgg gccgaaccat tcaccggagc gcgcagcggg       120
tggagtgtgg ctcggaggac cgcggcgggt caagcacctt tctcccccat atctgaaagc       180
atgccctttg tccacgtcgt ttacgctcat taaaacttcc agaatgcaac aggacggact       240
tggagtaggg acaaggaacg gaagtgggaa ggggaggagc gtgcacccct cctggccttg       300
gtgcgcgccg cgcccctaa ggtactttgg aagggacgcg cgggccagac gcgcccagac       360
ggccgcgatg gcgctgttgg ccggcgggct ctccagaggg ctgggctccc acccggccgc       420
cgcaggccgg gacgcggtcg tcttcgtgtg gcttctgctt agcacctggt gcacagctcc       480
tgccagggcc atccaggtga ccgtgtccaa cccctaccac gtggtgatcc tcttccagcc       540
tgtgaccctg ccctgtacct accagatgac ctcgaccccc acgcaaccca tcgtcatctg       600
gaagtacaag tctttctgcc gggaccgcat cgccgatgcc ttctcccgg ccagcgtcga       660
caaccagctc aatgcccagc tggcagccgg gaacccaggc tacaaccect acgttgagtg       720
ccaggacagc gtgcgcaccg tcagggtcgt ggccaccaag cagggcaacg ctgtgaccct       780
gggagattac taccagggcc ggaggattac catcaccgga aatgctgacc tgacctttga       840
ccagacggcg tgggggaca gtggtgtgta ttactgctcc gtggtctcag cccaggacct       900
ccaggggaac aatgaggcct acgcagagct catcgtcctt gggaggacct caggggtggc       960
tgagctctta cctggttttc aggcgggcc catagaagac tggctcttcg tggttgtggt      1020
atgcctggct gccttcctca tcttcctcct cctgggcatc tgctggtgcc agtgctgccc      1080
gcacacttgc tgctgctacg tcaggtgccc ctgctgccca gacaagtgct gctgccccga      1140
ggccctgtat gccgccggca agcagccac ctcaggtgtt cccagcattt atgcccccag      1200
cacctatgcc cacctgtctc ccgccaagac ccacccccca ccagctatga ttcccatggg      1260
ccctgcctac aacgggtacc ctggaggata ccctggagac gttgacagga gtagctcagc      1320
tggtggccaa ggctcctatg taccceetget tcgggacacg gacagcagtg tggcctctga      1380
agtccgcagt ggctacagga ttcaggccag ccagcaggac gactccatgc gggtcctgta      1440
ctacatggag aaggagctgg ccaacttcga cccttctcga cctggcccc ccagtggccg      1500
tgtggagcgg gccatgagtg aagtcacctc cctccacgag gacgactggc gatctcggcc      1560
ttcccggggc cctgccctca ccccgatccg ggatgaggag tggggtggcc actcccccg      1620
gagtcccagg ggatgggacc aggagcccgc cagggagcag gcaggcgggg gctggcgggc      1680
caggcggccc cgggcccgct ccgtggacgc cctggacgac ctcacccgc cgagcaccgc      1740
cgagtcaggg agcaggtctc ccacgagtaa tggtgggaga agccgggcct acatgccccc      1800
gcggagccgc agccgggacg acctctatga ccaagacgac tcgagggact tcccacgctc      1860
ccgggacccc cactacgacg acttcaggtc tcggagcgc cctcctgccg accccaggtc      1920
ccaccaccac cgtacccggg accctcggga caacggctcc aggtccgggg acctccccta      1980
tgatgggcgc ctactggagg aggctgtgag gaagaagggg tcggaggaga ggaggagacc      2040
ccacaaggag gaggaggaag aggcctacta cccgccgcg ccgccccgt actcggagac      2100
cgactcgcag gcgtcccgag agcgcaggct caagaagaac ttggccctga gtcgggaaag      2160
```

```
tttagtcgtc tgatctgacg tttttctacgt agcttttgta ttttttttt taatttgaag    2220 gaacactgat gaagccctgc catacccctc ccgagtctaa taaaacgtat aatcacaaaa    2280
aaaaaaaaaa aa                                                        2292

<210> SEQ ID NO 9
<211> LENGTH: 19
<212> TYPE: DNA
<213> ORGANISM: Artificial Sequence
<220> FEATURE:
<223> OTHER INFORMATION: Sense Strand of LSR siRNA#1 Target Sequence

<400> SEQUENCE: 9
cgucguuuac gcucauuaa                                                 19

<210> SEQ ID NO 10
<211> LENGTH: 19
<212> TYPE: DNA
<213> ORGANISM: Artificial Sequence
<220> FEATURE:
<223> OTHER INFORMATION: Sense Strand of LSR siRNA#2 Target Sequence

<400> SEQUENCE: 10
ggauuaccau caccggaaa                                                 19

<210> SEQ ID NO 11
<211> LENGTH: 17
<212> TYPE: DNA
<213> ORGANISM: Artificial Sequence
<220> FEATURE:
<223> OTHER INFORMATION: Antisense Strand of LSR siRNA#1 Target Sequence

<400> SEQUENCE: 11
aaugagcgua aacgacg                                                   17

<210> SEQ ID NO 12
<211> LENGTH: 19
<212> TYPE: DNA
<213> ORGANISM: Artificial Sequence
<220> FEATURE:
<223> OTHER INFORMATION: Antisense Strand of LSR siRNA#2 Target Sequence

<400> SEQUENCE: 12
uccggugaug guaaucctc                                                 19

<210> SEQ ID NO 13
<211> LENGTH: 21
<212> TYPE: DNA
<213> ORGANISM: Artificial Sequence
<220> FEATURE:
<223> OTHER INFORMATION: LSR siRNA#1 Sense Sequence

<400> SEQUENCE: 13
cgucguuuac gcucauuaat t                                              21

<210> SEQ ID NO 14
<211> LENGTH: 21
<212> TYPE: DNA
<213> ORGANISM: Artificial Sequence
<220> FEATURE:
<223> OTHER INFORMATION: LSR siRNA#2 Sense Sequence

<400> SEQUENCE: 14
ggauuaccau caccggaaat t                                              21
```

<210> SEQ ID NO 15
<211> LENGTH: 19
<212> TYPE: RNA
<213> ORGANISM: Artificial Sequence
<220> FEATURE:
<223> OTHER INFORMATION: LSR siRNA#1 Antisense Sequence

<400> SEQUENCE: 15
uuaaugagcg uaaacgacg                                                    19

<210> SEQ ID NO 16
<211> LENGTH: 21
<212> TYPE: DNA
<213> ORGANISM: Artificial Sequence
<220> FEATURE:
<223> OTHER INFORMATION: LSR siRNA#2 Antisense Sequence

<400> SEQUENCE: 16
uuuccgguga ugguaaucct c                                                 21

<210> SEQ ID NO 17
<211> LENGTH: 20
<212> TYPE: DNA
<213> ORGANISM: Artificial Sequence
<220> FEATURE:
<223> OTHER INFORMATION: LSR Forward Primer

<400> SEQUENCE: 17
gggaggacct cagggtggc                                                    20

<210> SEQ ID NO 18
<211> LENGTH: 20
<212> TYPE: DNA
<213> ORGANISM: Artificial Sequence
<220> FEATURE:
<223> OTHER INFORMATION: LSR Reverse Primer

<400> SEQUENCE: 18
tggtgggggt ggggtcttgg                                                   20

<210> SEQ ID NO 19
<211> LENGTH: 17
<212> TYPE: DNA
<213> ORGANISM: Artificial Sequence
<220> FEATURE:
<223> OTHER INFORMATION: Beta-actin Forward Primer

<400> SEQUENCE: 19
agcctcgcct ttgccga                                                      17

<210> SEQ ID NO 20
<211> LENGTH: 15
<212> TYPE: DNA
<213> ORGANISM: Artificial Sequence
<220> FEATURE:
<223> OTHER INFORMATION: Beta-actin Reverse Primer

<400> SEQUENCE: 20
ctggtgcctg gggcg                                                        15

<210> SEQ ID NO 21
<211> LENGTH: 649
<212> TYPE: PRT
<213> ORGANISM: Homo sapiens

<400> SEQUENCE: 21

-continued

```
Met Gln Gln Asp Gly Leu Gly Val Gly Thr Arg Asn Gly Ser Gly Lys
 1               5                   10                  15

Gly Arg Ser Val His Pro Ser Trp Pro Trp Cys Ala Pro Arg Pro Leu
            20                  25                  30

Arg Tyr Phe Gly Arg Asp Ala Arg Ala Arg Arg Ala Gln Thr Ala Ala
        35                  40                  45

Met Ala Leu Leu Ala Gly Gly Leu Ser Arg Gly Leu Gly Ser His Pro
 50                  55                  60

Ala Ala Ala Gly Arg Asp Ala Val Val Phe Val Trp Leu Leu Leu Ser
 65              70                  75                  80

Thr Trp Cys Thr Ala Pro Ala Arg Ala Ile Gln Val Thr Val Ser Asn
                85                  90                  95

Pro Tyr His Val Val Ile Leu Phe Gln Pro Val Thr Leu Pro Cys Thr
            100                 105                 110

Tyr Gln Met Thr Ser Thr Pro Thr Gln Pro Ile Val Ile Trp Lys Tyr
        115                 120                 125

Lys Ser Phe Cys Arg Asp Arg Ile Ala Asp Ala Phe Ser Pro Ala Ser
130                 135                 140

Val Asp Asn Gln Leu Asn Ala Gln Leu Ala Ala Gly Asn Pro Gly Tyr
145                 150                 155                 160

Asn Pro Tyr Val Glu Cys Gln Asp Ser Val Arg Thr Val Arg Val Val
            165                 170                 175

Ala Thr Lys Gln Gly Asn Ala Val Thr Leu Gly Asp Tyr Tyr Gln Gly
        180                 185                 190

Arg Arg Ile Thr Ile Thr Gly Asn Ala Asp Leu Thr Phe Asp Gln Thr
    195                 200                 205

Ala Trp Gly Asp Ser Gly Val Tyr Tyr Cys Ser Val Val Ser Ala Gln
210                 215                 220

Asp Leu Gln Gly Asn Asn Glu Ala Tyr Ala Glu Leu Ile Val Leu Gly
225                 230                 235                 240

Arg Thr Ser Gly Val Ala Glu Leu Leu Pro Gly Phe Gln Ala Gly Pro
            245                 250                 255

Ile Glu Asp Trp Leu Phe Val Val Val Cys Leu Ala Ala Phe Leu
            260                 265                 270

Ile Phe Leu Leu Leu Gly Ile Cys Trp Cys Gln Cys Cys Pro His Thr
        275                 280                 285

Cys Cys Cys Tyr Val Arg Cys Pro Cys Cys Pro Asp Lys Cys Cys Cys
        290                 295                 300

Pro Glu Ala Leu Tyr Ala Ala Gly Lys Ala Ala Thr Ser Gly Val Pro
305                 310                 315                 320

Ser Ile Tyr Ala Pro Ser Thr Tyr Ala His Leu Ser Pro Ala Lys Thr
            325                 330                 335

Pro Pro Pro Pro Ala Met Ile Pro Met Gly Pro Ala Tyr Asn Gly Tyr
        340                 345                 350

Pro Gly Gly Tyr Pro Gly Asp Val Asp Arg Ser Ser Ser Ala Gly Gly
        355                 360                 365

Gln Gly Ser Tyr Val Pro Leu Leu Arg Asp Thr Asp Ser Ser Val Ala
    370                 375                 380

Ser Glu Val Arg Ser Gly Tyr Arg Ile Gln Ala Ser Gln Gln Asp Asp
385                 390                 395                 400

Ser Met Arg Val Leu Tyr Tyr Met Glu Lys Glu Leu Ala Asn Phe Asp
            405                 410                 415
```

Pro Ser Arg Pro Gly Pro Ser Gly Arg Val Glu Arg Ala Met Ser
            420             425             430

Glu Val Thr Ser Leu His Glu Asp Asp Trp Arg Ser Arg Pro Ser Arg
        435                 440             445

Gly Pro Ala Leu Thr Pro Ile Arg Asp Glu Glu Trp Gly Gly His Ser
450                 455                 460

Pro Arg Ser Pro Arg Gly Trp Asp Gln Glu Pro Ala Arg Glu Gln Ala
465                 470             475                 480

Gly Gly Gly Trp Arg Ala Arg Pro Arg Ala Arg Ser Val Asp Ala
                485             490                 495

Leu Asp Asp Leu Thr Pro Pro Ser Thr Ala Glu Ser Gly Ser Arg Ser
            500             505             510

Pro Thr Ser Asn Gly Gly Arg Ser Arg Ala Tyr Met Pro Pro Arg Ser
        515             520             525

Arg Ser Arg Asp Asp Leu Tyr Asp Gln Asp Asp Ser Arg Asp Phe Pro
        530             535             540

Arg Ser Arg Asp Pro His Tyr Asp Asp Phe Arg Ser Arg Glu Arg Pro
545             550             555             560

Pro Ala Asp Pro Arg Ser His His Arg Thr Arg Asp Pro Arg Asp
            565             570             575

Asn Gly Ser Arg Ser Gly Asp Leu Pro Tyr Asp Gly Arg Leu Leu Glu
            580             585             590

Glu Ala Val Arg Lys Lys Gly Ser Glu Arg Arg Pro His Lys
            595             600             605

Glu Glu Glu Glu Ala Tyr Tyr Pro Pro Ala Pro Pro Tyr Ser
            610             615             620

Glu Thr Asp Ser Gln Ala Ser Arg Glu Arg Arg Leu Lys Lys Asn Leu
625             630             635             640

Ala Leu Ser Arg Glu Ser Leu Val Val
            645

<210> SEQ ID NO 22
<211> LENGTH: 594
<212> TYPE: PRT
<213> ORGANISM: Mus musculus

<400> SEQUENCE: 22

Met Ala Pro Ala Ala Ser Ala Cys Ala Gly Ala Pro Gly Ser His Pro
1               5                   10                  15

Ala Thr Thr Ile Phe Val Cys Leu Phe Leu Ile Ile Tyr Cys Pro Asp
            20                  25                  30

Arg Ala Ser Ala Ile Gln Val Thr Val Pro Asp Pro Tyr His Val Val
        35                  40                  45

Ile Leu Phe Gln Pro Val Thr Leu His Cys Thr Tyr Gln Met Ser Asn
    50                  55                  60

Thr Leu Thr Ala Pro Ile Val Ile Trp Lys Tyr Lys Ser Phe Cys Arg
65                  70                  75                  80

Asp Arg Val Ala Asp Ala Phe Ser Pro Ala Ser Val Asp Asn Gln Leu
                85                  90                  95

Asn Ala Gln Leu Ala Ala Gly Asn Pro Gly Tyr Asn Pro Tyr Val Glu
            100                 105                 110

Cys Gln Asp Ser Val Arg Thr Val Arg Val Val Ala Thr Lys Gln Gly
        115                 120                 125

Asn Ala Val Thr Leu Gly Asp Tyr Tyr Gln Gly Arg Arg Ile Thr Ile
    130                 135                 140

-continued

```
Thr Gly Asn Ala Asp Leu Thr Phe Glu Gln Thr Ala Trp Gly Asp Ser
145                 150                 155                 160

Gly Val Tyr Tyr Cys Ser Val Val Ser Ala Gln Asp Leu Asp Gly Asn
                165                 170                 175

Asn Glu Ala Tyr Ala Glu Leu Ile Val Leu Gly Arg Thr Ser Glu Ala
            180                 185                 190

Pro Glu Leu Leu Pro Gly Phe Arg Ala Gly Pro Leu Glu Asp Trp Leu
        195                 200                 205

Phe Val Val Val Cys Leu Ala Ser Leu Leu Phe Phe Leu Leu Leu
210                 215                 220

Gly Ile Cys Trp Cys Gln Cys Cys Pro His Thr Cys Cys Cys Tyr Val
225                 230                 235                 240

Arg Cys Pro Cys Pro Asp Lys Cys Cys Cys Pro Glu Ala Leu Tyr
                245                 250                 255

Ala Ala Gly Lys Ala Ala Thr Ser Gly Val Pro Ser Ile Tyr Ala Pro
            260                 265                 270

Ser Ile Tyr Thr His Leu Ser Pro Ala Lys Thr Pro Pro Pro Pro
        275                 280                 285

Ala Met Ile Pro Met Arg Pro Pro Tyr Gly Tyr Pro Gly Asp Phe Asp
290                 295                 300

Arg Thr Ser Ser Val Gly Gly His Ser Ser Gln Val Pro Leu Leu Arg
305                 310                 315                 320

Glu Val Asp Gly Ser Val Ser Ser Glu Val Arg Ser Gly Tyr Arg Ile
                325                 330                 335

Gln Ala Asn Gln Gln Asp Asp Ser Met Arg Val Leu Tyr Tyr Met Glu
            340                 345                 350

Lys Glu Leu Ala Asn Phe Asp Pro Ser Arg Pro Gly Pro Pro Asn Gly
        355                 360                 365

Arg Val Glu Arg Ala Met Ser Glu Val Thr Ser Leu His Glu Asp Asp
370                 375                 380

Trp Arg Ser Arg Pro Ser Arg Ala Pro Ala Leu Thr Pro Ile Arg Asp
385                 390                 395                 400

Glu Glu Trp Asn Arg His Ser Pro Arg Ser Pro Arg Thr Trp Glu Gln
                405                 410                 415

Glu Pro Leu Gln Glu Gln Pro Arg Gly Gly Trp Gly Ser Gly Arg Pro
            420                 425                 430

Arg Ala Arg Ser Val Asp Ala Leu Asp Asp Ile Asn Arg Pro Gly Ser
        435                 440                 445

Thr Glu Ser Gly Arg Ser Pro Pro Ser Ser Gly Arg Gly Arg
450                 455                 460

Ala Tyr Ala Pro Pro Arg Ser Arg Ser Arg Asp Leu Tyr Asp Pro
465                 470                 475                 480

Asp Asp Pro Arg Asp Leu Pro His Ser Arg Asp Pro His Tyr Tyr Asp
                485                 490                 495

Asp Leu Arg Ser Arg Asp Pro Arg Ala Asp Pro Arg Ser Arg Gln Arg
            500                 505                 510

Ser His Asp Pro Arg Asp Ala Gly Phe Arg Ser Arg Asp Pro Gln Tyr
        515                 520                 525

Asp Gly Arg Leu Leu Glu Glu Ala Leu Lys Lys Lys Gly Ala Gly Glu
530                 535                 540

Arg Arg Arg Val Tyr Arg Glu Glu Glu Glu Glu Glu Glu Gly His
545                 550                 555                 560
```

```
Tyr Pro Pro Ala Pro Pro Tyr Ser Glu Thr Asp Ser Gln Ala Ser
            565             570             575

Arg Glu Arg Arg Met Lys Lys Asn Leu Ala Leu Ser Arg Glu Ser Leu
            580             585             590

Val Val
```